(12) United States Patent
Koepsell et al.

(10) Patent No.: US 9,155,778 B2
(45) Date of Patent: Oct. 13, 2015

(54) TRIPEPTIDES THAT DOWN REGULATE THE ACTIVITY OF PLASMA MEMBRANE TRANSPORTERS INCLUDING SODIUM-D-GLUCOSE COTRANSPORTER SGIT1

(75) Inventors: Hermann Koepsell, Höchberg (DE); Alexandra Vernaleken, Eiterfeld (DE)

(73) Assignee: JULIUS-MAXMILLIANS-UNIVERSITAT WURZBURG, Wurzburg (DE)

(*) Notice: Subject to any disclaimer, the term of this patent is extended or adjusted under 35 U.S.C. 154(b) by 1276 days.

(21) Appl. No.: 11/910,594

(22) PCT Filed: Mar. 31, 2006

(86) PCT No.: PCT/EP2006/002981
§ 371 (c)(1),
(2), (4) Date: Nov. 20, 2007

(87) PCT Pub. No.: WO2006/105913
PCT Pub. Date: Oct. 12, 2006

(65) Prior Publication Data
US 2009/0203621 A1 Aug. 13, 2009

Related U.S. Application Data

(60) Provisional application No. 60/715,175, filed on Sep. 9, 2005.

(30) Foreign Application Priority Data

Apr. 4, 2005 (EP) ..................................... 05007319

(51) Int. Cl.
A61K 38/06 (2006.01)
A61K 9/20 (2006.01)
G01N 33/68 (2006.01)
A61K 38/08 (2006.01)

(52) U.S. Cl.
CPC ................. *A61K 38/06* (2013.01); *A61K 38/08* (2013.01)

(58) Field of Classification Search
None
See application file for complete search history.

(56) References Cited

U.S. PATENT DOCUMENTS

2004/0010121 A1* 1/2004 Birse et al. .................... 530/350

FOREIGN PATENT DOCUMENTS

| DE | 10006887 A1 | 9/2001 | |
| EP | 1444890 A | 8/2004 | |
| WO | WO 03055912 A2 * | 7/2003 | ............. C07K 14/52 |
| WO | WO 2004/061088 * | 7/2004 | |

OTHER PUBLICATIONS

Definition of derivative from http://cancerweb.ncl.ac.uk/omd/about. html, pp. 1-5. Accessed Jul. 7, 2005.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Douek DC, "Disrupting T-cell homeostasis: how HIV-1 infection causes disease," AIDS Rev., 2003, 5: 172-177.*
Neonatal hypernatremia from Merck manual, pp. 1-2. Accessed May 26, 2010.*
Polyuria from Merck manual, pp. 1-5. Accessed May 26, 2010.*
Chronic Kidney Disease from Merck manual, pp. 1-7. Accessed May 26, 2010.*
Intro to Cancer from Merck manual, p. 1. Accessed Mar. 5, 2008.*
Clinical aspects of Cancer from Merck manual, pp. 1-4. Accesssed Mar. 5, 2008.*
Jain Rakesh K, "Barriers to Drug Delivery in Solid Tumors," Scientific American, Jul. 1994, pp. 58-65.*
Gura T "Systems for Identifying New Drugs Are Often Faulty," Science, 1997, 278: 1041-1042.*
Auerbach R, Akhtar N, Lewis RL, Shinners BL, "Angiogenesis assays: Problems and pitfalls," Cancer and Metastasis Reviews, 2000, 19: 167-172.*
HIV and Kidney Disease from aidsinfonet.org, pp. 1-3. Accessed May 26, 2010.*

(Continued)

*Primary Examiner* — James H Alstrum Acevedo
*Assistant Examiner* — Erinne Dabkowski
(74) *Attorney, Agent, or Firm* — Foley & Lardner LLP

(57) ABSTRACT

A regulatory protein RS1 fragment or a nucleic acid molecule encoding the regulatory protein RS1 fragment for the preparation of a pharmaceutical composition, food and/or food supplements for the amelioration, prevention and/or treatment of a metabolic disease or a secondary disorder caused by a (pathological) modification of homeostasis, wherein the RS1 fragment is characterized in comprising at least the amino acid sequence Q-C-P Glutamine-Cysteine-Proline) or derivatives thereof, is provided. Also provided is a method for the amelioration, prevention and/or treatment of a metabolic disease or a secondary disorder caused by a (pathological) modification of homeostasis comprising administering a pharmaceutically active amount of a regulatory protein RS1 fragment or a nucleic acid molecule encoding a regulatory protein RS1 fragment, wherein the RS1 fragment comprises at least the amino acid sequence Q-C-P or derivatives thereof.

11 Claims, 15 Drawing Sheets

(56) References Cited

OTHER PUBLICATIONS

Figure 1:
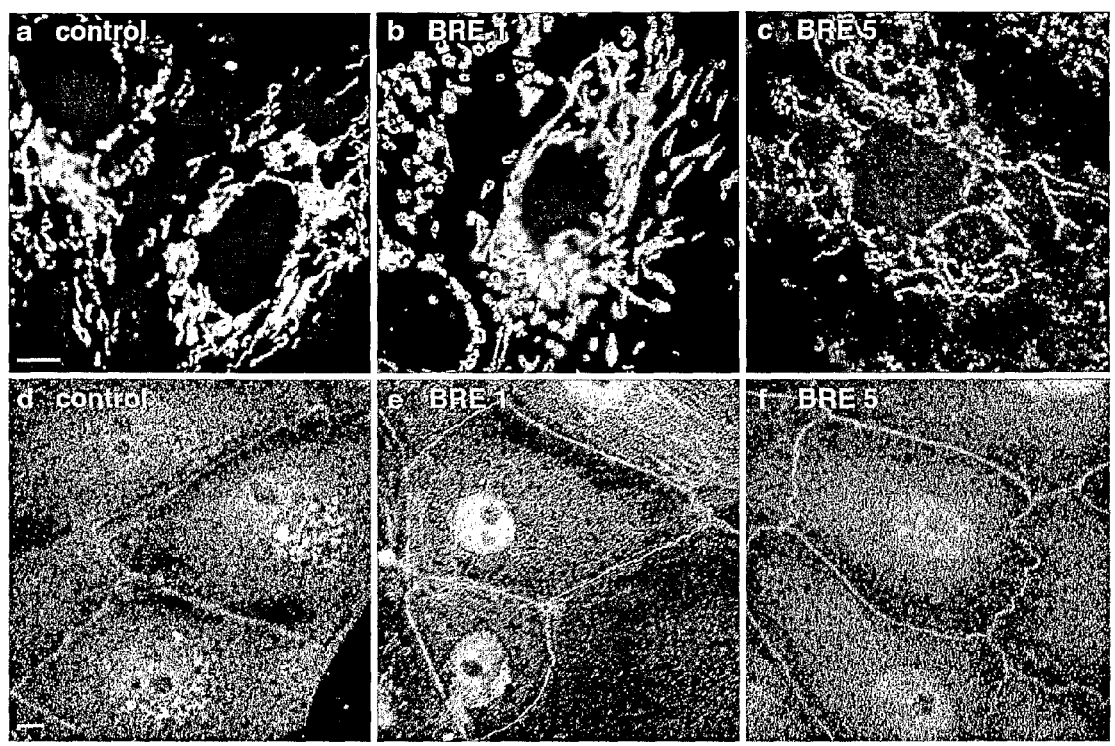

Cao X, Fang L, Gibbs S, Huang Y, Dai Z, Wen P, Zheng X, Sadee W, Sun D, "Glucose uptake inhibitor sensitizes cancer cells to daunorubicin and overcomes drug resistance in hypoxia," Cancer Chemother Pharmacol, 2007, 59(4): 495-505.*
Shakhashiri, Chemical of the week, Water, www.scifun.org, Jan. 2011.*
UniProt Protein Database, protein Accession Q92681, Regulatory solute carrier protein family 1 member 1, accessed on Oct. 14, 2014.*
International Search Report for International PCT Application No. PCT/EP2006/002981, dated Sep. 5, 2006. (4 pgs.).
Lambotte, S. et al., "The Human Gene of a Protein That Modifies Na+-D-Glucose Co-Transport", *DNA and Cell Biology*, vol. 15, No. 9, Sep. 1996, pp. 769-777. (XP000993045).
Valentin M. el al., "The Transport Modifier RS1 is Localized at the Inner Side of the Plasma Membrane and Changes Membrane Capacitance", *Biochimica et Biophysica ACTA*, vol. 1468, No. 1-2, Sep. 2000, pp. 367-380. (XP004273331).
Ahima, Rexford S., et al., "Role of leptin in the neuroendocrine response to fasting," Nature, 1996, pp. 250-252, vol. 382.
Banting et al., "TGN38 and its orthologues: roles in post-TGN vesicle formation and maintenance of TGN morphology," Biochimica et Biophysica Acta, 1997, pp. 209-217, vol. 1355.
Barsh, Gregory S., et al., "Genetics of body-weight regulation," Nature, 2000, pp. 644-651, vol. 404.
Bray, G. A., et al., "Sibutramine produces dose-related weight loss," Obesity Research, 1999, pp. 189-198, vol. 7, http//www.obesityresearch.org/cgi/content/abstract/7/2/189, abstract only.
Bruford, E. A., et al., "Linkage Mapping in 29 Bardet-Biedl Syndrome Families Confirms Loci in Chromosomal Regions 11q13, 15q22.3-q23, and 16q21," Genomics, Article No. GE974613, 1997, pp. 93-99, vol. 41.
Chen, Nian-Hang, et al., "Synaptic uptake and beyond: the sodium- and chloride-dependent neurotransmitter transporter family SLC6," Eur J Physiol, 2004, pp. 519-531, vol. 447.
Chicurel, Marina, "Whatever happened to leptin?" Nature, 2000, pp. 538-540, vol. 404.
Clément, Karine, et al., "A mutation in the human leptin receptor gene causes obesity and pituitary dysfunction," Nature, 1998, pp. 398-401, vol. 392.
Cleveland, Don W., et al., "Peptide Mapping by Limited Proteolysis in Sodium Dodecyl Sulfate and Analysis by Gel Electrophoresis," The Journal of Biological Chemistry, 1977, pp. 1102-1106, vol. 252, No. 3.
Colditz, Graham A., et al., "Weight Gain as a Risk Factor for Clinical Diabetes Mellitus in Women," Annals of Internal Medicine, 1996, pp. 481-486, vol. 122, Issue 7, http://www.annals.org/cgi/content/full/122/7/781.
Daniel et al., "The proton oligopeptide cotransporter family SLC15 in physiology and pharmacology," Eur. J. Physiol., 2004, pp. 610-618, vol. 447.
Derossi, Daniele, et al., "The Third Helix of the Antennapedia Homeodomain Translocates through Biological Membranes," The Journal of Biological Chemistry, 1994, pp. 10444-10450, vol. 269, No. 14.
Diez-Sampedro, Ana, et al., "A glucose sensor hiding in a family of transporters," PNAS, 2003, pp. 11753-11758, vol. 100, No. 20.
Dudash, Joseph, et al., "Glycosylated dihydrochalcones as potent and selective sodium glucose co-transporter 2 (SGLT2) inhibitors," Elsevier, Bioorganic & Medicinal Chemistry Letters 14, 2004, pp. 5121-5125, www.sciencedirect.com.
Elias et al., "Leptin Activates Hypothalamic Cart Neurons Projecting to the Spinal Cord," Neuron, Dec. 1998, pp. 1375-1385, vol. 21.
Elias, Carol F., et al., "Leptin Differentially Regulates NPY and POMC Neurons Projecting to the Lateral Hypothalamic Area," Neuron, 1999, pp. 775-786, vol. 23.
Erickson, Jay C., et al., "Attenuation of the Obesity Syndrome of ob/ob Mice by the Loss of Neuropeptide Y," Science, 1996, pp. 1704-1707, vol. 274, No. 5293, http://www.sciencemag.org/cgi/content/abstract/274/5293/1704.
Fan, Wei, et al., "Role of melanocortinergic neurons in feeding and the agouti obesity syndrome," Nature, 1997, pp. 165-168, vol. 385.
Farooqi, I. Sadaf, et al., "Dominant and recessive inheritance of morbid obesity associated with melanocortin 4 receptor deficiency," The Journal of Clinical Investigation, 2000, pp. 271-279, vol. 106, No. 2.
Friedman, J.M., "Obesity in the new millennium," Nature, 2000, pp. 632-634, vol. 404.
Fujioka, Ken, Management of Obesity as a Chronic Disease: Nonpharmacologic, Pharmacologic, and Surgical Options, Obesity Research, 2002, pp. 116S-123S, vol. 10, Supp. 2.
Gorboulev et al., "Selectivity of the Polyspecific Cation Transporter Roct1 Is Changed by Mutation of Aspartate 475 to Glutamate," Mol. Pharmacol., 1999, pp. 1254-1261, vol. 56.
Gupta, Prem N., et al., "Non-invasive vaccine delivery in transfersomes, niosomes and liposomes: a comparative study," Elsevier, International Journal of Pharmaceutics, 2005, pp. 73-82, vol. 293.
Helms et al., "Inhibition by brefeldin A of a Golgi membrane enzyme that catalyses exchange of guanine nucleotide bound to ARF," Nature, Nov. 1992, 2 pages, vol. 360 [retrieved on Nov. 9, 2007] Retrieved from the Internet: <URL: http://www.nature.com/nature/journal/v360/n6402/pdf/360352a0.pdf>.
Jackson et al., "Turning on ARF: the Sec7 family of guanine-nucleotide-exchange factors," Cell Biol., Feb. 2000, pp. 60-67, vol. 10.
Jiang, Wei, et al., "IRIP, a New Ischemia/Reperfusion-Inducible Protein That Participates in the Regulation of Transporter Activity," Molecular and Cellular Biology, 2005, pp. 6496-6508, vol. 25, No. 15.
Kawakami, S., et al., "Effect of cationic charge on receptor-mediated transfection using manno-sylated cationic liposome/plasmid DNA complexes following the intravenous administration in mice," Pharmazie, 2004, pp. 405-408, vol. 59.
Kayser, O., et al., "The Impact of Nanobiotechnology on the Development of New Drug Delivery Systems," (Abstract), Current Pharmaceutical Biotechnology, 2005, pp. 3-5(3), vol. 6, No. 1, abstract only.
Kipp et al., "More than apical: distribution of SGLT1 in Caco-2 cells," Am. J. Physiol. Cell. Physiol., Oct. 2003, pp. C737-C749, vol. 285.
Klausner et al., "Brefeldin A: Insights into the Control of Membrane Traffic and Organelle Structure," J. Cell Biol., 1992, pp. 1071-1080, vol. 116.
Koepsell Hermann, et al., The SLC22 drug transporter family, Eur J Physiol, 2004, pp. 666-676, vol. 447.
Koepsell, H., et al., "Topical Review—Function and Presumed Molecular Structure of $Na^+_{-D-}$ Glucose Cotransport Systems," The Journal of Membrane Biology, 1994, pp. 1-11, vol. 138.
Kolehmainen, J., et al., "Refined mapping of the Cohen syndrome gene by linkage disequilibrium," http://www.ncbi.nlm.nih.gov/sites/entrez?cmd=Retrieve&db=Pub. Accessed Nov. 20, 2007, abstract only.
Kolterman, Orville G., et al., "Mechanisms of Insulin Resistance in Human Obesity," J. Clin. Invest., The American Society for Clinical Investigation, 1980, pp. 1272-1284, vol. 65.
Kopelman, Peter G., "Obesity as a medical problem," Nature, 2000, pp. 635-643.
Korn, Thomas, et al., "The Plasma Membrane-associated Protein RS1 Decreases Transcription of the Transporter SGLT1 in Confluent LLC-$PK_1$ Cells," The Journal of Biological Chemistry, 2001, pp. 45330-45340, vol. 276, No. 48.
Krude, Heiko, et al., "Severe early-onset obesity, adrenal insufficiency and red hair pigmentation caused by POMC mutations in humans," Nature Genetics, 1999, pp. 155-157, vol. 19.
Lambotte, Stephan, et al., "The Human Gene of a Protein That Modifies $Na^+_{-D-}$ Glucose Co-Transport," DNA and Cell Biology, 1996, pp. 769-777, vol. 15, No. 9.

(56) References Cited

OTHER PUBLICATIONS

Lowell, Bradford B., et al., "Towards a molecular understanding of adaptive thermogenesis," Nature, 2000, pp. 652-660, vol. 404.

Luzio et al., "Identification, sequencing and expression of an integral membrane protein of the *trans*-Golgi network (TGN38)," Biochem. J., 1990, pp. 97-102, vol. 270.

Mahato, Ram I., "Water insoluble and soluble lipids for gene delivery," Elsevier, Advanced Drug Delivery Reviews, 2005, pp. 699-712, vol. 57.

Mathews, Katherine D., et al., "Linkage Localization of Börjeson-Forssman-Lehmann Syndrome," American Journal of Medical Genetics, 1989, pp. 470-474, vol. 34.

McLellan, Faith, "Obesity rising to alarming levels around the world," The Lancet, 2002, p. 1412, vol. 359.

Moghimi et al., "Nanomedicine: current status and future prospects, The Faseb Journal," Mar. 2005, pp. 311-330, vol. 19.

Ohta, T., et al., "Imprinting-Mutation Mechanisms in Prader-Willi Syndrome," Am J. Hum. Genet., 1999, pp. 397-413, vol. 64.

Oku, Akira, et al., "T-1095, an Inhibitor of Renal $Na^+$-Glucose Cotransporters, May Provide a Novel Approach to Treating Diabetes," Diabetes, 1999, pp. 1794-1800, vol. 48.

Osswald, Christina, et al., "Mice without the Regulatory Gene Rsc1A1 Exhibit Increased $Na^+_{D-}$ Glucose Cotransport in Small Intestine and Develop Obesity," Molecular and Cellular Biology, 2005, pp. 78-87, vol. 25, No. 1.

Owens et al., "Identification of two short internal ribosome entry sites selected from libraries of random oligonucleotides," PNAS, Feb. 13, 2001, pp. 1471-1476, vol. 98, No. 4.

Peppas et al., "Expert Opinion on Biological Therapy," Expert Opinion, Jun. 2004, 2 pages, vol. 4, No. 6 [retrieved on Nov. 21, 2007 [Retrieved from the Internet: <URL: http://www.expertopin.com/doi/abs/10.1517/14712598.4.6.881>.

Pérusse et al., "The Human Obesity Gene Map: The 1998 Update," Obesity Research, Jan. 1999, pp. 111-129, vol. 7, No. 1.

Russell-Eggitt, Isabelle M., et al., "Alström Syndrome, Report of 22 Cases and Literature Review," Ophthalmology, 1998, pp. 1274-1280, vol. 105, No. 7.

Schwartz, Michael W., et al., "Central nervous system control of food intake," Nature, 2000, pp. 661-671, vol. 404.

Snyder, Eric E., et al., "The Human Obesity Gene Map: The 2003 Update," Obesity Research, 2004, pp. 369-439, vol. 12, No. 3.

Spengler, Bernhard, et al., "Peptide Sequencing by Matrix-assisted Laser-desorption Mass Spectrometry," Rapid Communications in Mass Spectrometry, 1992, pp. 105-108, vol. 6.

Strobel, Andreas, et al., "A leptin missense mutation associated with hypogonadism and morbid obesity," Nature Genetics, 1998, vol. 18.

Torchilin, Vladimir P., "Recent Advances With Liposomes As Pharmaceutical Carriers," Nature Reviews, 2005, pp. 145-160, vol. 4.

Vaisse, Christian, et al., "A frameshift mutation in human MC4R is associated with a dominant form of obesity," Nature Genetics, 1998, pp. 113-114, vol. 20.

Valentin, Marc, et al., "The transport modifier RS1 is localized at the inner side of the plasma membrane and changes membrane capacitance," Elsevier, Biochimica Et Biophysica Acta, 2000, pp. 367-380, vol. 1468.

Veyhl, Maike, et al., "Cloning of a Membrane-associated Protein Which Modifies Activity and Properties of the $Na^+_{D-}$ Glucose Cotransporter," The Journal of Biological Chemistry, 1993, pp. 25041-25053, vol. 268, No. 33.

Wadden, T.A., et al., "Valvular heart disease in fenfluramine—phentermine-treated patients: a comparison with control patients," NCBI, Obesity Reearch, 1999, pp. 309-310, vol. 7, No. 3, http://www.ncbi.nlm.nih.gov/sites/entrez?cmd=Retrieve&db=Pub.

Wright et al., "The sodium/glucose cotransport family SLC5," Eur. J. Physiol., 2004, pp. 510-518, vol. 447.

Zhang, Yiying, et al., "Positional cloning of the mouse obese gene and its human homologue," Nature, 1994, pp. 425-432, vol. 372.

\* cited by examiner

Figure 9

TRIPEPTIDES THAT DOWN REGULATE THE ACTIVITY OF PLASMA MEMBRANE TRANSPORTERS INCLUDING SODIUM-D-GLUCOSE COTRANSPORTER SGlT1

SEQUENCE LISTING

The instant application contains a Sequence Listing which has been submitted via EFS-Web and is hereby incorporated by reference in its entirety. Said ASCII copy, created on Mar. 3, 2010, is named 02862202.txt, and is 60,473bytes in size The present invention relates to the use of a regulatory protein RS1 fragment or a nucleic acid molecule encoding said regulatory protein RS1 fragment for the preparation of a pharmaceutical composition for the amelioration, prevention and/or treatment of a metabolic disease or a secondary disorder caused by a (pathological) modification of homeostasis, wherein said RS1 fragment is characterized in comprising at least the amino acid sequence Q-C-P (Glutamine-Cysteine-Proline) or derivatives thereof. Furthermore, the present invention relates to a method for the amelioration, prevention and/or treatment of a metabolic disease or a secondary disorder caused by a (pathological) modification of homeostasis, said method comprising administering to a patient in need of such amelioration, prevention and/or treatment a pharmaceutically active amount of a regulatory protein RS1 fragment or a nucleic acid molecule encoding a regulatory protein RS1 fragment, wherein said RS1 fragment is characterized in comprising at least the amino acid sequence Q-C-P (Glutamine-Cysteine-Proline) or derivatives thereof. Moreover, the present invention relates to the use of a regulatory protein RS1 fragment or a nucleic acid molecule encoding said regulatory protein RS1 fragment for the preparation of food, feeds and/or food supplements.

In the affluent industrial nations, the increased occurrence of nutrition-dependent diseases (e.g. obesity/adipositas, hypercholesterolemia, diabetes, hyperglycaemia, diarrhoea, various bile disorders, various renal disorders like hypertension and various disorders related to the deposition of sodium urate crystals like gout) is a serious problem. In many cases, such nutrition-dependent diseases are secondary diseases and pathological consequences caused by obesity as a consequence of overnutrition. For instance, pathological consequences of increased glucose concentrations in the blood due to diabetes are retinopathia and renal failures. Further, overweight and diabetes are risk factors for diseases such as hypertension, heart attack, biliary stones, e.g. bile disorders and gout etc.

Especially obesity has risen to alarming levels world-wide (McLellan (2002), Lancet 359, 1412). For Example, the average weight of German conscripts now increases by almost 400 g/year. Similar data were obtained in Austria, Norway and the UK.

Obesity or "adipositas" is a complex disorder of appetite regulation and/or energy metabolism controlled by specific biological factors. Besides severe risks of illness such as diabetes, hypertension and heart disease, individuals suffering from obesity are often isolated socially.

Human obesity is strongly influenced by environmental and genetic factors, whereby the environmental influence is often a hurdle for the identification of (human) obesity genes.

Obesity is defined as a Body Mass Index (BMI) of 30 kg/m$^2$ or more. BMI is calculated by dividing the weight in kg by the height in metres squared. "Overweight" is defined as a BMI between 25 and 30 kg/m$^2$. A person is considered obese if he or she has 20 percent (or more) extra body fat for his/her age, height, sex, and bone structure.

Obesity has, a major impact on a person's physical, social and emotional well-being. Besides this, obesity can lead to an increased risk of illness including type 2 diabetes and high blood pressure (hypertension) that can lead to other cardiovascular diseases and stroke. Obesity can also play a role in cancer, problems with sexual-function, muscle and bone disorders and dyslipidaemia.

Major advances have recently been made in identifying components of the homeostatic system(s) that regulate body weight/mass. Several candidate genes have been associated with mammalian/human obesity or its metabolic complications (Kopelman, Nature 404 (2000), 634-643). For instance, one key element of the homeostatic system regulating body weight/mass is the hormone leptin (Friedman (1998), Nature 395, 763-770; Friedman (2000), Nature 404, 632-634; Chicurel (2000), Nature 404, 538-540). Leptin is produced by fat tissue and reports nutritional information to key regulatory centers in the hypothalamus. A decrease in body fat leads to a decreased level of leptin, which in turn stimulates food intake. Furthermore, decreased leptin levels activate a hormonal response that is characteristic of a starvation state (Ahima (1996), Nature 382, 250-252). Leptin acts on nerve cells in the brain and modulates this function. Several neuropeptides are implicated in the control of energy homeostasis, inter alia, neuropeptide Y (NPY) and agouti-related protein (AGRP), α-melanocyte-stimulating hormone (α-MSH) and cocaine— and amphetamine—regulated transcript (CART); see Friedman (2000), loc. cit.; Schwartz (2000), Nature 404, 661-671; Erickson (1996), Science 274, 1704-1707; Fan (1997), Nature 385, 165-168. Neuronal circuits furthermore regulate further effector molecules which have recently been identified (for review see Lowell (2000), Nature 404, 652-660). These effector molecules comprise uncoupling proteins (UCP1, UCP2 and/or UCP3; Lowell (2000), loc. cit.) and peroxisome proliferator-activated receptor-γ (PPAR-γ) co-activator (PGC-I), a key regulator of the genes that regulate thermogenesis (Puigserver (1998), Cell 92, 829-839).

Furthermore, energy balance and thereby body weight/ mass is modulated by the above mentioned neuropeptides and further (neurogenic) factors, like pro-opiomelanocortin (POMC), the precursor of α-MSH (Elias (1999), Neuron 23, 775-786). Mutations in POMC are implicated in obesity (Krude (1998), Nature Genetics 19, 155).

Additional mutations are described which cause modified and/or altered leptin responses. For example, in 3-5% of extreme obese individuals, mutations in the MSH receptor (MC4R), leading to leptin resistance, have been described (Friedman (2000), loc. cit.; Vaisse (1998), Nature Gen. 20, 113-114). Mutations in the leptin receptor itself are also associated with extreme obesity (Clement (1998), Nature 392, 398-401).

Accordingly, obesity is not to be considered as a single disorder but a heterogeneous group of conditions with (potential) multiple causes. Therefore, obesity is also characterized by elevated fasting plasma insulin and an exaggerated insulin response to oral glucose intake (Kolterman (1980), J. Clin. Invest 65, 1272-1284) and a clear involvement of obesity in type 2 diabetes mellitus can be confirmed (Kopelman (2000), loc. cit.; Colditz (1995), Arch. Int. Med. 122, 481-486).

As with other complex diseases, rare obesity mutations have been described which have been identified by mendelian pattern of inheritance and position mapping (see Barsh (2000), Nature 404, 644-650). With one or two notable exceptions, the map positions of obesity loci identified by quantitative studies do not correspond to defined (mouse) obesity mutations such as ob (leptin), fat (carboxypeptidase E) or tubby (tubby protein). Map positions have been determined for some clinical syndromes, like Prader-Willi, Cohen, Alstrom, Bardet-Biedl or Borjeson-Forssman-Lehman, but the causative genes have not yet been isolated (see Barsh (2000), loc. cit.; Ohta (1999), Am. J. Hum. Gen. 64, 397-413; Kolehmainen (1997), Eur. J. Hum. Gen. 5, 206-213; Russell-Eggitt (1998), Ophtalmology 105, 1274-1280; Mathews (1989), Am. J. Med. Gen. 34, 470-474; Bruford (1997), Genomics 41, 93-99). The "human obesity gene map" contains entries for more than 40 genes and 15 chromosomal regions in which published studies indicate a possible relationship to adiposity or a related phenotype (Barsh (2000), loc. cit., Perusse (1999), Obes. Res. 7, 111-129). Said "obesity gene map" comprises, however, mainly large chromosomal areas and does not provide for distinct genes involved in obesity. Lately (2003), Snyder has published an extended version of the "obesity gene map" and more than 430 genes, markers, chromosomal regions have been associated or linked with human obesity phenotypes; Snyder (2004), Obes. Res. 12, 369-439.

Much effort has been spent to understand the pathophysiology of obesity. Apart from the rare monogenic causes for severe disturbances of the eating regulation—genetic alterations of the ob gene (leptin) (Zhang (1996), Nature 372, 425-32; Strobel (1998), Nat. Tenet. 18, 213-215), the leptin receptor (Clement (1998), Nature 392, 398-401), a mutation of the melanocortin 4 receptor (MC4R) gene (Farooqi (2000), J. Clin. Invest. 106, 271-279), and mutations in the pro-opiomelanocortin (POMC) gene (Krude (1998), Nat. Genet. 19, 155-157)—obesity appears to show a multifactorial etiopathogenesis.

Known therapies for obese patients comprise in particular physical activity, diet as well as drug therapy.

Many drugs tested as an appetite suppressant interfere with monoamine-neurotransmitters (serotonin, noradrenalin, dopamine, histamine). 5-HT (5-hydroxytryptamine) is released in various sites of the hypothalamus, a brain region believed to be involved in the regulation of food intake. D-fenfluramine is a 5-HT releaser and reuptake inhibitor mostly used in combination with Phentermine (Fen-Phen) to treat obesity. Fen-Phen was withdrawn from the market due to potential heart valve defects (Wadden (1999), Obes. Res. 7, 309-310). Also sibutramine, a 5-HT and noradrenalin reuptake inhibitor (Knoll Pharma; Bray (1999), Obes. Res 7, 189-198) was shown to support weight loss when used to support a low calorie diet.

Orlistat (XENICAL®) prevents the absorption of some fat in the intestine. Just under a third of the fat that would otherwise have been absorbed passes straight through the bowel and is excreted in the faeces.

Also in the treatment of obesity, appetite depressants and/or appetite suppressants have been proposed. These comprise sympathomimetic drugs, canthine hydrochloride, phenylpropanolamine hydrochloride, ampfepramone hydrochloride, as well as serotonin-norepinephrine reuptake-inhibitor, like simbutramine hydrochloride. All of these substances modify appetite, but as they do not specifically target nucleus arcuate neurones and solely modify their function e.g., via NMDA receptors, antiobesity drugs also effect other than arcuate nucleus structures. This might explain the variety of (side) effects of these substances, apart from just modulating satiety.

The popular appetite suppressant drug fenfluramine and dexfenfluramine have been withdrawn from the market. The FDA stated that these two drugs are linked to heart valve disease and Primary Pulmonary Hypertension (PPH). PPH is a rare disease which causes the progressive narrowing of the blood vessels of the lungs and mostly results in death.

Also topiramate has recently been proposed in the treatment of obesity. Topiramate demonstrated appetite suppressant properties. Topiramate belongs to a class of medications called anticonvulsants. Usually it is used with other medications to treat certain types of seizures in patients with epilepsy or Lennox-Gastaut syndrome (a disorder that causes seizures and developmental delays). Accordingly, topiramate, marketed as an anti-epileptic drug, is now being evaluated for other indications like obesity, neuropathic pain and management of bipolar mania (The Pharmaceutical Journal (1999), Vol. 263, No 7064, page 475).

As stated in Fujioka (2002), Obes. Res. Suppl. 2, 116S-123S topiramate is a structurally and pharmacologically novel anticonvulsant agent that was approved in 1996 for treatment of epilepsy. Unlike most antiepileptic agents, topiramate seems to lead to appetite suppression. Yet, it has several other actions, including as an antagonist of voltage-gated sodium channels and modulation of alpha-aminobutyric acid-A activity.

However, topiramate is known to provide for side effects in brain regions. Kaminski (2004) showed that topiramate selectively inhibits postsynaptic responses mediated by GluR5 kinate receptors.

Also in the treatment of obesity, diabetes and/or the corresponding secondary disorders, therapeutical forms like various special diets (having extreme ratios of nutrients), psychopharmacological drugs and an α-glucosidase inhibitor (acarbose, Glucobay®, Bayer-Vital, Leverkusen) that inhibits the degradation of disaccharides in small intestine, have been proposed. All known therapeutical forms exhibit the major disadvantage to have severe side effects.

As further means for the treatment of nutrition-related diseases, the development of inhibitors of the sodium-D-glucose cotransporters SGLT1 and SGLT2 are proposed. SGLT1 and SGLT2 mediate the first step in the absorption of D-glucose in small intestine and in reabsorption of D-glucose in renal proximal tubules. These attempts been the treatment of nutrition related diseases are based on the development of non-transported substrate analogues that act as competitive inhibitors (Oku (1999), Diabetes 48, 1794-1800; Dudash (2004), Bioorg. Med. Chem. Lett. 14, 5121-5125). The inhibition of glucose transport by such compounds requires their continuous presence at the binding site at high concentrations. This permanent presence can cause side effects in organs which are not desired to be affected (e.g. severe detrimental effects in brain or heart).

Beside the problem of side effects of pharmacological options for the treatment of nutrition related diseases, diets comprising a sharp reduction of food uptake over a long period of time are often not accepted by the patients and a change in nutrient habits is often refused.

Attempts were also made to provide therapies for the treatment of nutrition-related diseases, like diabetes and hyperglycaemia, by the provision of antagonists (for example antibodies, anti-sense molecules, ribozymes and the like) of the regulatory protein RS1 (see DE-A1 10006887). In DE-A1 10006887, it is thought that the in vivo level of RS1 is to be reduced in order to treat, e.g. diabetes. RS1 is a regulatory protein well known in the art (see, e.g. Veyhl (1993), J. Biol. Chem. 268, 25041-25053.; Koepsell (1994), J. Membrane Biol. 138, 1-11.; Lambotte (1996), DNA and Cell Biology 15, 9, 769-777.; Valentin (2000), Biochimica et Biophysica 1468, 367-380.; Korn (2001), J. of Biological Chemistry 276, 48, 45330-45340; Veyhl (2003), J. Membrane Biol. 196, 71-81.; Osswald (2005), Mol Cell Biol. 25, 78-87.). The human RS1

(Acc. No. NM_006511, X82877; Lambotte (1996), DNA and Cell Biology 15, 9, 769-777.) consists of 617 amino acids with 74% amino acid identity to RS1 from pig (Acc. No. NM_213793, X64315, Veyhl (1993), J. Biol. Chem. 268, 25041-25053.). Other homolog RS1 proteins are from rabbit (Acc. No. X82876) or mouse (Acc. No. Y11917).

Since RS1, inter alia, inhibits the uptake of glucose within the small intestine and its reabsorption within the renal proximal tubules (see, e.g. Veyhl (2003), J. Membrane Biol. 196, 71-81; Osswald (2005), Mol Cell Biol. 25, 78-87), the provision of antagonists of this regulatory protein can not be considered for the treatment, amelioration and/or prevention of high glucose peaks in the blood, for example of glucose peaks in diabetic patients.

The RSC1A1 gene codes for RS1. RS1 (i) inhibits the human sodium-D-glucose cotransporter hSGLT1 and some other plasma membrane transporters posttranscriptionally (Veyhl (2003), J. Membrane Biol. 196, 71-81), (ii) is located within the cytosol as well as within nuclei (Osswald (2005), Mol Cell Biol. 25, 78-87), and (ii) inhibits transcription of SGLT1 (Korn (2001), J. Biol. Chem. 276, 45330-45340). Recently, RS1 was also identified as a protein interacting with the ischemia/reperfusion-inducible protein (IRIP) and it was proposed that RS1 may be involved in an IRIP-dependent regulation of ion transporters, like the organic cation transporter 2 (OCT2; Jiang (2005), Mol Cell Biol. 25 (15), 6496-508).

In an animal model it was previously shown that the removal of RS1 leads to a post-transcriptional upregulation of SGLT1, to an increase of serum cholesterol and to obesity. Regulation of RSC1A1 gene (expression and/or activity) can be used to influence obesity and the concentration of cholesterol in the blood. RS1, as a molecule or as an RS1 encoding gene, was proposed to be used in the treatment of adipositas or hypercholesterolemia; see EP-A1 444 890. An RS1-knock-out animal model, the alternation of the activity of RS1 in influencing body weight and the possibility to diagnose obesity via testing the expression or activity of RS1 has been described in EP-A1 444890 and in U.S. Ser. No. 10/771,151.

Unfortunately, until now, no useful concept for changing/modifying the situation of overweight, fat/sugar-related malnutrition and even obesity has been provided. Merely insufficient therapeutic options for nutrition-related diseases with severe side-effects have been proposed in the prior art.

Even if several candidate genes have been associated with human obesity or its metabolic complications and even the provision that down-regulation of RS1 may lead to increased body weight, the identification of additional and/or concise factors that influence obesity and/or adiposity is necessary. Strategies to treat and/or prevent pathological body-weight/body mass regulations are desired.

Therefore, the technical problem underlying this invention was to provide for simple means and methods for modulating (pathological) homeostatic conditions, in particular adipositas/obesity and/or energy homeostatic circuits. The solution to said technical problem is achieved by providing the embodiments characterized in the claims, whereby said solution is not only applicable to pathological conditions, but may also be useful in non-pathological situations, like in non-obese individuals.

Accordingly, the present invention relates to the use of (a) regulatory protein RS1 fragment(s) or a nucleic acid molecule encoding such (a) regulatory protein RS1 fragment(s) for the preparation of a pharmaceutical composition for the amelioration, prevention and/or treatment of a metabolic disease or a secondary disorder caused by a (pathological) modification of homeostasis. E. g., said RS1 fragment is characterized in comprising at least the amino acid sequence Q-C-P (Glutamine-Cysteine-Proline) or derivatives of said tripeptide.

Furthermore, the present invention relates to a method for the amelioration, prevention and/or treatment of a metabolic disease or a secondary disorder caused by a (pathological) modification of homeostasis, said method comprising administering to a patient in need of such amelioration, prevention and/or treatment a pharmaceutically active amount of a regulatory protein RS1 fragment or a nucleic acid molecule encoding a regulatory protein RS1 fragment, wherein said RS1 fragment is characterized in comprising at least the amino acid sequence Q-C-P (Glutamine-Cysteine-Proline) or derivatives thereof.

Moreover, the present invention relates to the use of a regulatory protein RS1 fragment or a nucleic acid molecule encoding said regulatory protein RS1 fragment for the preparation of food, feed and/or food supplements, wherein said RS1 fragment is characterized in comprising at least the amino acid sequence Q-C-P (Glutamine-Cysteine-Proline) or derivatives thereof.

In the experimental part, also a further peptide to be employed in context of the present invention is described, said peptide comprising at least three amino acid residues as comprised in the amino acid sequence S-D-S-D-R-I-E-P (Serine-Aspartic acid-Serine-Aspartic acid-Arginine-Isoleucine-Glutamic acid-Proline) (SEQ ID NO: 9). This peptide or a peptide/protein comprising said amino acid sequence (or comprising at least 3consecutive amino acid residues of the same) or comprising the amino acid sequences of smaller or larger peptides (e. g. I-K-P -S-D-S-D-R-I-E-P (Isoleucine-Lysine-Proline-Serine-Aspartic acid-Serine-Aspartic acid-Arginine-Isoleucine-Glutamic acid-Proline) (SEQ ID NO: 10)) may also be employed in accordance with this invention.

In context of the present invention, said derivatives of Q-C-P may be, e.g., Q-S-P (Glutamine-Serine-Proline), Q-P-P (Glutamine-Proline-Proline) or Q-T-P (Glutamine-Threonine Proline). The effectiveness of such derivatives in context of the present invention is also demonstrated in the appended examples.

It is also envisaged for the uses, means and methods provided herein that combinations of the herein described RS1 fragments (or derivatives thereof) are employed in context of the present invention. E. g. it is envisaged that all possible combinations of peptides/proteins consisting of or comprising the amino acid sequences Q-C-P, Q-S-P , Q-T-P, Q-P-P, Q-T-P and/or S-D-S-D-R-I-E-P (SEQ ID NO: 9) (or consisting of or comprising at least 3consecutive amino acid residues of S-D-S-D-R-I-E-P (SEQ ID NO: 9)) are employed. Corresponding "combination experiments" are also provided in the appended, non-limiting examples. However, it is also envisaged in context of the present invention that only one particular RS 1fragment or derivative thereof is employed alone and not in combination with any other RS 1fragment or derivative thereof.

It is of note that also nucleic acid molecules encoding the herein described RS1 fragments may be employed in context of the present invention.

As documented herein below and in the appended examples, it was, in accordance with this invention, surprisingly found that specific fragments of the regulatory protein RS1 or nucleic acid molecules encoding the same, negatively influence the glucose uptake in vivo. This RS1 fragment to be employed in accordance with the herein defined "Q-C-P" fragment, also referred to as "RS1 fragment". However, in context of the present invention, the term "RS1 fragment" also comprises (I-K-P-) S-D-S-D-R-I-E-P (SEQ ID NO: 10) (or at least 3 consecutive amino acid residues thereof) and derivatives thereof (defined herein).

It was further surprisingly found that there are distinct differences between the effect of total RS1 protein on the one hand and of the RS1 fragments described herein, e.g. the tripeptide QCP (or the derivatives thereof) or the peptide SDSDRIEP (SEQ ID NO: 9) (or at least 3 consecutive amino acid residues thereof) (or the derivatives thereof), on the other hand.

Apparently both, total RS1 protein and the smaller fragments derived therefrom and described herein are thought (without being bound by theory) to inhibit the exocytotic pathway within a short time period of less than 30 min. Inhibition of the exocytotic pathway was shown by demonstrating that the inhibitory effect on expression of hSGLT1 in oocytes by total RS1 protein, by the peptide QCP or SDSDRIEP (SEQ ID NO: 9) could be prevented if the exocytotic pathway was blocked by botulinum toxin B or by brefeldin A.

However, the following differences between total hRS1 protein and the said peptides were observed and, inter alia, documented in the appended examples: Whereas the inhibition of hSGLT1 expressed AMG uptake in oocytes by injection of total hRS1 protein was increased after stimulation of protein kinase C (PKC) using sn-1,2-dioctanoyl-glycerol (DOG) or phorbol-12-myristate-13-acetate (PMA), the inhibition of hSGLT1 expressed AMG uptake in oocytes by injection of the peptide QCP or SDSDRIEP (SEQ ID NO: 9) was not changed. Therefore, and not being bound by theory, the effect of the herein described peptides does not depend on PKC. This is in sharp contrast to the effect of total hRS1.

In addition, whereas the inhibition of hSGLT1 expressed AMG uptake in oocytes by injection of total hRS1 protein was reduced when a dominant negative mutant of dynamin I was coexpressed, the inhibition of hSGLT1 expressed AMG uptake in oocytes by injection of the peptide QCP or SDSDRIEP (SEQ ID NO: 9) was not changed after coexpression of dominant negative mutant of dynamin I. Therefore, the effect of the peptides as described herein may not dependent on the function of dynamin I. Unexpectedly, this is a further distinct difference to the effects observed with total hRS1.

Furthermore, whereas the expression of the uptake of radioactively labeled tetraethylammonium [$^{14}$C]TEA in oocytes by the human organic cation transporter 1 (hOCT1) appears to be inhibited after injection of total hRS1 protein in the presence of an intracellular AMG concentration of 0.1 mM), hOCT2 expressed [$^{14}$C]TEA uptake in oocytes appears not to be inhibited after injection of QCP. Corresponding measurements were performed in the presence of intracellular AMG concentrations of 0.1 mM, <0.01 mM or 10 mM.

Without being bound by theory, these data indicate a different specificity of the target transporter for total hRS1 compared to the RS1 fragments described herein, in particular QCP (or derivatives thereof).

In context of the present invention, the term "total RS1" refers to a polypeptide that has the function of the naturally occurring RS1. For instance, such "total RS1" may be the full length hRS1, e.g. as characterized by a polypeptide comprising the amino acid sequence of SEQ ID NO: 2 or a fragment of said amino acid sequence having the function of the naturally occurring hRS1.

Due to the simplicity of the herein defined minimal peptide structures, pharmaceutical composition for the treatment of a metabolic disease or a secondary disorder caused by a pathological modification of homeostasis may be prepared. Said pharmaceutical compositions comprise the herein defined minimal peptide (RS1 fragment) or a nucleic molecule encoding the same or even a (gene-expression) vector comprising said nucleic acid molecule. Also provided are, accordingly, means and methods for the medical intervention in pathological disorders relating to homeostasis, in particular over-weight, obesity/adipositas and secondary disorders provided herein and detailed below. Also provided are means and methods for the preparation of food, feed and/or food additives, said method(s) comprising the addition of the herein defined specific functional "Q-C-P" fragments (or derivatives thereof) of RS1 to food, feed and/or food precursors.

Accordingly, the invention also relates to food, feed, food precursors and/or food additives prepared in accordance with the herein defined methods, namely the addition of the RS1 fragments; in particular the Q-C-P-fragment (alone or in combination with the at least three consecutive amino acid residues of the above described SDSDRIEP (SEQ ID NO: 9) peptide and/or other QCP derivatives as described herein), as provided herein.

The present application, inter alia, provides for a compound that inhibits the expressed activity of SGLTs and other nutrient transporters and thereby exhibit a more prolonged inhibition of transport of glucose or other nutrients, compared to e.g. the competitive inhibitors (Oku (1999), Diabetes 48, 1794-1800.; Dudash (2004), Bioorg. Med. Chem. Lett. 14, 5121-5125). Side effects, as caused by the continuous presence of such competitive inhibitors or medicaments described above, can not occur.

Accordingly, the technical problem of the current invention was solved by the development of medicaments and/or "functional food" that employ mechanism for posttranscriptional inhibition of nutrient-transporters by specific RS1 fragments. The mechanism by which RS1-specific fragments of the invention down-regulate transporters posttranscriptionally is provided below and in the experimental part. Accordingly, specific functionally active domains of RS1 are identified and specific peptides from these RS1-domains as defined herein are provided. In addition, methods to introduce these inventive peptides, e.g. tripeptides, into selected groups of cells are described.

In the experimental part it is shown that RS1 is not only localized at the plasma membrane and within the nucleus as previously described (Korn (2001), J. Biol. Chem. 276, 45330-45340; Osswald (2005), Mol. Cell. Biol. 25, 78-87) but also at the trans-Glogi network (TGN). Evidence is provided that RS1 at the TGN is released after treatment of cells with brefeldin A which classifies RS1 as a TGN coat-protein and suggests that RS1 is involved in sorting at the TGN. In addition, the posttranscriptional inhibition of SGLT1 expression by RS1 is due to an inhibition of the exocytotic pathway of plasma membrane transporters, as documented below.

Most importantly, specific peptides, in particular peptides being or comprising Q-C-P residues (or derivatives thereof) are described, which influence negatively specific nutrient transporters/receptors in vivo. In particular, the tripeptide QCP (Glutamine-Cysteine-Proline) or derivatives thereof are provided in accordance with this invention. As shown in the appended examples, QCP or derivatives thereof (and also (IKP)SDSDRIEP (SEQ ID NO: 10)) leads to posttranscriptional downregulatation of (nutrient) transporters. QCP inhibits the exocytotic pathway of plasma membrane transporters from the Golgi apparatus to the plasma membrane. It was also demonstrated that QCP is translocated by the proton-peptide co-transporter PEPT1. This allows even the extra cellular application of QCP or a derivative thereof and to direct its effects to cells that express proton-peptide co-transporters. Such an extra cellular application is particularly useful in the medical and/or nutritional methods provided herein.

Accordingly, the present invention provides for the use of a regulatory protein RS1 fragment/RS1 minimal peptide or a nucleic acid molecule encoding said regulatory protein RS1 fragment/RS1 minimal peptide for the preparation of a pharmaceutical composition for the amelioration, prevention and/or treatment of a metabolic disease or a secondary disorder caused by a (pathological) modification of homeostasis, wherein said RS1 fragment to be employed in the herein defined uses and methods is characterized in comprising at least the amino acid sequence Q-C-P (Glutamine-Cysteine-Proline) or derivatives thereof.

Within the present application, the term "regulatory protein RS1 fragment", RS1 minimal peptide" or "RS1 fragment" relates to an amino acid stretch of an RS1 protein as defined herein and as illustratively shown in any of SEQ ID Nos 2, 4, 6 or 8 or as encoded by a nucleic acid molecule as shown in SEQ ID Nos. 1, 3, 5 or 7. The "amino acid stretch" to be employed in accordance with this invention is the stretch Q-C-P, QSP, QPP or QTP (one letter code) and the corresponding "RS1 fragment(s)" comprise(s) these three amino acid residues in this consecutive order. As shown in the appended examples, it was surprisingly found that the reciprocal amino acid stretch, i.e. P—C-Q, is not functional and, accordingly, that the herein defined amino acid stretch (in N- to C-terminal order) in the format of "Q-C-P" is to be employed.

The amino acid stretch/fragment of the present invention comprises (or is) at least 3 amino acid residues. However even long and longer fragments/amino acid stretches may be employed and used in accordance with this invention. The "Q-C-P" comprising fragments may comprise, one additional amino acid residue, two additional amino acid residues, three additional amino acid residues, four additional amino acid residues, five additional amino acid residues, six additional amino acid residues, seven additional amino acid residues, eight additional amino acid residues, nine additional amino acid residues or ten additional amino acid residues. However, also longer amino acid stretches, comprising the herein defined "RS1 fragment", namely the Q-C-P motive/peptide", are envisaged. Accordingly, said "RS1 fragment" may comprise at least 3, 5, 7, 9, 11, 13, 14, 15, 16, 17, 18, 19, at least 20, at least 30, at least 40, at least 50, at least 60, at least 70, at least 80, at least 90 or at least 100 amino acid residues. Most preferably, the additional amino acid residues are residues as also comprised in the herein defined RS1 proteins. Preferably, said "RS1 fragment" or "Q-C-P motive/peptide" as defined herein comprises at the most 150 amino acid residues, more preferably at the most 120 amino acid residues. However, in accordance with this invention, smaller peptides of 3 to 12 amino acid residues are preferred, whereby more preferred are 3 to 10 amino acid residues. Most preferably, said amino acid stretch/fragment has a length of three amino acids, namely the amino acid stretch/fragment "Q-C-P" or derivatives thereof, like Q-S-P , Q-P-P or Q-T-P. It is envisaged that the above-described fragments are consecutive stretches of the herein defined RS1 protein. Said "fragments" of RS1 protein may, in accordance with the present invention, also be comprised in fusion constructs, like fusion proteins. These "fusion proteins" and corresponding embodiments are disclosed and exemplified below. In accordance with this invention, it is also envisaged that peptides are employed which comprise the Q-C-P motive (or derivatives thereof) in form of repeats/tandems and the like. Accordingly, also (synthetic or recombinant) peptides are envisaged which are or which comprise motives like "Q-C-P-Q-C-P" (SEQ ID NO: 11) and/or "Q-C-P-Q-C-P-Q-C-P" (SEQ ID NO: 12). Accordingly, said "Q-C-P motive" may be repeated in one fragment/amino acid stretch. Said repetitions may comprise 2, 3, 4, 5, 6, 7, 8, 9 or more repeated Q-C-P stretches. Said repeated stretches may be interrupted by spacers/linkers of other amino acid residues. Accordingly, the repeated sequences may be of the format "Q-C-P-X-Q-C-P" (SEQ ID NO: 13) or "X-Q-C-P-X-Q-C-P-X" (SEQ ID NO: 14), wherein "X" represents any amino acid residue and any number of amino acid residues. However, preferably "X" is selected from the group consisting of the amino acid residues A (Alanine), K (Lysine) or R (Arginine) and the number of linker/spacer amino acid residues is preferably at least one. More preferably, the number of linker/spacer amino acid residues is 3.

Further more, the "X" of the peptides as described above may be a site, cleavable by hydrolysis (e.g. catalyzed by hydrolases). In particular, "X" may be S-S. Furthermore, "X" may be an ester bond which, for instance, may be cleavable by esterases. It is envisaged, that the peptides consisting of or comprising repeats/tandems of the RS1 fragments as defined herein may also comprise more than 150 amino acids.

Moreover, in accordance with the present invention, it is envisaged that the RS1 fragments as defined herein or repeats/tandems thereof may be attached to further amino acids, heterologous peptides and/or heterologous proteins. Said further or additional amino acids may also comprise the above described "further minimal RS1 fragment", namely the peptide comprising at least 3 consecutive amino acid residues comprised in the amino acid stretch S-D-S-D-R-I-E-P (SEQ ID NO:9). Said further or additional amino acids may also comprise the above described derivatives of QCP, e.g. QSP, QPP or QTP as well as all possible combinations of the herein described RS1 fragments. Furthermore, said further amino acids, heterologous peptides and/or heterologous proteins may comprise, derived from and/or consisting of domains having additional functionalities, like, e.g. domains providing further pharmacological effects or specific tags for facilitating protein purification, like, e.g., His-tags. Accordingly the RS1 fragments as defined herein may also be part of fusion polypeptides or fusion proteins. In accordance with the present invention, said fusion polypeptides or fusion proteins comprising the RS1 fragments as defined herein may also comprise more than 150 amino acids.

As documented in the appended examples, besides the herein identified and claimed minimal peptide Q-C-P, also a further minimal peptide was identified which comprises the amino acid residues S-D-S-D-R-I-E-P (Serine-Aspartic acid-Serine-Aspartic acid-Arginine-Isoleucine-Glutamic acid-Proline) (SEQ ID NO: 9). Also this peptide may comprise additional amino acid residues, preferably as comprised in the herein defined RS1 protein, as documented in the appended examples, e.g. the amino acid residues "I-K-P" (as non-limiting example).

Accordingly, also provided is, in accordance with this invention, a further amino acid stretch which may be equally employed in the means, uses and methods of this invention, whereby this amino acid stretch is characterized in comprising at least 3 amino acid residues as comprised in the amino acid sequence S-D-S-D-R-I-E-P (Serine-Aspartic acid-Serine-Aspartic acid-Arginine-Isoleucine-Glutamic acid-Proline) (SEQ ID NO: 9) or derivatives thereof. The embodiments provided for the herein defined "Q-C-P" minimal stretch apply, mutatis mutandis, for the additional amino acid "RS1 fragment" provided herein and comprising at least 3 amino acid residues as comprised in the amino acid sequence S-D-S-D-R-I-E-P (SEQ ID NO: 9). Again said S-D-S-D-R-I-E-P (SEQ ID NO: 9) is provided in the orientation "N-terminus" to "C-terminus" and the reciprocal amino acid stretch ("P-E-I-R-D-S-D-S") (SEQ ID NO: 15) may not be employed in accordance with this invention. However, the "minimal 3amino acid fragment "S-D -S" and/or "DSD" is/are also envisaged in accordance with this invention.

It is of note that the uses and methods provided herein, relate mainly to the herein defined RS1fragment "Q-C-P" and its also defined derivatives. However, in the herein provided uses, means and methods it is also envisaged that the inventive RS1fragment, being characterized in comprising at least the amino acid sequence Q-C-P (Glutamine-Cysteine-Proline) or derivatives thereof, may be employed/used in (a) combination(s) with the above described further "minimal RS1fragment", namely the peptide comprising at least 3consecutive amino acid residues comprised in the amino acid stretch S-D-S-D-R-I-E-P (SEQ ID NO: 9), and/or in (a) combination(s) with the above described QCP derivatives, e. g. QSP, QTP and/or QPP. However, it is also envisaged that (a) combination(s) of said further "minimal RS1fragment" and/or said QCP derivatives lacking particularly QCP are employed in context of the present invention.

Within the present application, the term "Q-C-P or derivatives thereof" relates preferably to tripeptides with one ore two amino acid substitutions in said three-amino-acid stretch "Q-C-P". Accordingly, a corresponding and exemplified "Q-C-P" derivative may be of the format of QSP, QTP, QPP, QAP, QGP, NCP, DCP, ECP, NSP, DSP or ESP. However, in accordance with this invention, it is preferred that the useful amino acid stretch comprises or is "Q-C-P", "Q-S-P ", "Q-T-P" or "Q-P-P". As pointed out above, "S" corresponds to "serine", "D" corresponds to "aspartic acid", "T" corresponds to "threonine", "P" corresponds to "proline", "N" corresponds to "asparagine", "A" corresponds to "alanine", "G" corresponds to "glycine" and "E" corresponds to "glutamate".

It is to be understood, that the embodiments characterized herein for the "Q-C-P" peptide are also applicable for the herein defined "Q-C-P derivatives", in particular the exemplified "Q-C-P derivatives" in the format of QSP, QTP, QPP, QAP, QGP, NCP, DCP, ECP, NSP, DSP or ESP, like, in particular "Q-S-P", "Q-T-P" or "Q-P-P". In this context, it is also referred to the appended examples providing experimental data not only for the "Q-C-P" tripeptide, but also for "Q-C-P derivatives", e.g. for "Q-C-P derivatives" where the cysteine residue (C) is replaced by other amino acids, e.g. for Q-S-P, Q-T-P and Q-P-P. It is of note that the human RS1 sequence also contains the Q-S-P motive and the Q-P-P motive (e.g., see SEQ ID NO: 2).

Moreover, the term "Q-C-P or derivatives thereof" or "RS1 fragments" also relates to Q-C-P (or QSP or Q-T-P or Q-P-P, etc; see above) derivatives having the peptide bond substituted by a covalent bond which is not proteolytically cleavable. Such covalent bound may be, for instance, selected from the group consisting of —CH2-CH2-, —CH(OH)—CH2-, —CH2-CH(OH)—, —CH(OH)—CH(OH)—, —C═O—CH2-, —CH2—C═0—, —CH(OH)—C═O—, —CH═CH—, —C(OH)═CH2-, —CH═C(OH)—, C(OH)═C(OH)—, —N═CH—, —N═C(OH)—. Preferably, such covalent bound may be, for instance, selected from the group consisting of —CH2—C═0—, —CH(OH)—C═O—, CH═CH—, —CH═C(OH)—, C(OH)═C(OH)—, —N═C(OH)—. Having such bonds, the tripeptides as defined herein are inert against further proteolytic digestion and therefore keep their functionality within the gastrointestinal tract. As pointed out above, the inventive "QCP" fragment may also be a fragment wherein several "QCP" motives are comprised and wherein said "QCP" motives are directly linked to each other (e.g. in the format "(. . .)Q-C-P-Q-C-P(. . .)" (SEQ ID NO: 11) or wherein said "QCP motives" are separated by linker structures and/or additional amino acid residues, e.g. in the format "(. . .)Q-C-P-X-Q-C-P(. . .)" (SEQ ID NO: 13), wherein "X" denotes at least one additional amino acid residue. Preferably, the above mentioned and defined "proteolytically inert" peptide bonds are comprised between "Q" and "C" and between "C" and "P" of the herein defined "three amino acid motive Q-C-P". Preferably, the bond between "Q" and "X" and/or between "P" and "X" is a peptide bond which is proteolytically cleavable. Accordingly, and in a most preferred embodiment of the present invention, the longer RS1fragments defined herein and comprising the "QCP motive" are in vivo proteolytically cleaved (for example after administration in the stomach by gastric juices, in the intestines or in the blood stream), whereby the "proteolytically inert" bonds defined above comprised between "Q" and "C" and between "C" and "P" is not cleaved in vivo, leading to a "proteolytically inert" "Q-C-P " tripeptide which is particularly useful in context of the means, methods and uses of the present invention. As mentioned above, the embodiments described herein are not restricted to the distinct "Q-C-P" tripeptide, but also to "Q-C-P derivatives", as defined above, e.g. QSP, QTP, QPP and the like.

In longer peptides (which, for example, cannot be taken up by PEPT1 and/or PEPT2), "Q-C-P peptides" or derivatives thereof having such "inert bonds" are not proteolytically cleavable. Without being bound by theory, these "inert QCP peptides" remain intact, whereas the remaining amino acids flanking said tripeptide(s) are proteolytically cleaved in vivo. This may lead to Q-C-P or derivatives thereof consisting only of 3 amino acids within the gastrointestinal tract. This kind of Q-C-P tripeptide or derivatives thereof can be transported, e.g. by PEPT1 and/or PEPT2 into those cells in which they are desired to be active.

The term "Q-C-P or derivatives thereof" or "RS1 fragment" relates also to secondary forms of the RS1 fragments described herein, e.g. to D- and L-isoforms, natural and unnatural salts and secondary forms with modifications like acetylation, methylation, glycosylation and/or phosphorylation and to substances with similar or the same mass-spectrometrical characteristics. It was found out that, e.g. the acetylated forms of the RS1 fragments described herein have the same effects in context of the present invention, e.g. the same effects on sugar uptake, as the non-acetylated forms. Accordingly, also secondary modifications/forms of the herein defined peptides are part of this invention.

Moreover, the term "Q-C-P or derivatives thereof" or "RS1 fragment" relates to all tripeptides or other substances that can function as substrates for (human) peptide-proton symporters, e.g. PEPT1 and/or PEPT2. The molecular features of said tripeptides or other substances are well known in the art and are described in e.g. Daniel (2004), Pflugers Arch. 447, 610-618. Corresponding screening assays for the function of these tripeptides as substrates for PEPT1 and/or PEPT2 can easily be deduced by the skilled artesian from Daniel (2004), loc cit.

In context of the present invention, it is also possibly that the "Q-C-P tripeptide" or "RS1 fragment" as defined herein or a peptide comprising the same is made hydrophobic. Such a hydrophobic peptide is envisaged to be able to cross (biological) membranes. For instance, Q-C-P may be coupled with antennapedia proteins (or fragments thereof) in order to obtain hydrophobic derivatives of QCP; see also Derossi (1994), J. Biol. Chem. 269, 10444-10450.

A "Q-C-P derivative" as defined herein is characterized in comprising and/or having the same tertiary structure as the original "Q-C-P" amino acid stretch alone or as comprised in a fragment with more amino acid residues. Accordingly, and most preferably, the "QCP derivatives" have, compared to the original Q-C-P motive an unchanged tertiary structure. The same applies, mutatis mutandis, to the further defined minimal peptide as described herein and being derived from the S-D-S-D-R-I-E-P (SEQ ID NO: 9) motive disclosed herein. The person skilled in the art is readily in a position to deduce corresponding three-dimensional structures and/or tertiary structures.

Accordingly, in order to further identify and/or verify useful Q-C-P derivatives or derivatives derived from the S-D-S-D-R-I-E-P (SEQ ID NO: 9) motive, several techniques which are known in the art may be employed. These techniques comprise, but are not limited to, in-gel digestions, electroelution procedures, microsequencing, amino acid analysis, Edman-sequencing or mass spectroscopy. Also crystalographic methods known in the art may be employed. For example, some techniques start directly from gel(s), others need a transfer to membranes by blotting. To the first group belong, inter alia, coelectrophoresis, internet comparison of position, peptide mapping by SDS-PAGE (Cleveland (1977), J. Biol. Chem. 252, 1102), protein elution and MALDI-MS or N-terminal sequencing by Edman degradation (Edman (1950), Acta Chem. Scand. 4, 283), enzymatic in-gel digestion, analysis of peptides directly in the mixture by mass spectrometry, peptide mass fingerprinting (Pappin (1993), Curr. Biol. 3, 327), ESI-MS (electrospray-ionization-MS), MALDI PMF and/or MALDI PDS (like, e.g. PSD-MALDI-MS (Spengler (1992), Rapid Commun. Mass Spectrom. 6, 105)).

In context of the present invention it is intended that the herein defined RS1 fragment, e.g. the Q-C-P peptide, can be taken up into those cells in which it is desired to be active/effective. The cells in which the peptides are desired to be effective are most preferably the small intestine epithelial cells, the renal proximal tubular epithelial cells, endothelial cells of blood vessels, epithelial cells of the rectum or colon, and/or epithelial cells of the skin. Accordingly, the Q-C-P peptide and the other RS1 fragments as described herein are capable to entry those cells in which it is desired to be effective. This entry may be mediated, without being bound by theory, via active transport, passive transport, endocytosis and/or via passive diffusion. Also envisaged is the translocation in said cells via a transport protein like a peptide carrier. Preferably, said carriers are the proton peptide co-transporters PEPT1 or PEPT2, most preferably PEPT1, as described herein.

In a further embodiment of the present invention a method for the amelioration, prevention and/or treatment of a metabolic disease or a secondary disorder caused by a (pathological) modification of homeostasis is provided. Said method comprises administering to a patient in need of such amelioration, prevention and/or treatment a pharmaceutically active amount of a regulatory protein RS1 fragment or a nucleic acid molecule encoding a regulatory protein RS1 fragment, wherein said RS1 fragment is characterized in comprising at least the amino acid sequence Q-C-P (Glutamine-Cysteine-Proline) or derivatives thereof. The embodiments provided above for the inventive use of the herein defined RS1 peptide(s)/fragment(s) apply, mutatis mutandis, for this inventive method for the amelioration, prevention and/or treatment of a metabolic disease or a secondary disorder caused by a (pathological) modification of homeostasis.

The metabolic disease or secondary disorder to be treated, ameliorated and/or prevented by the inventive use and methods provided herein is preferably selected from the group consisting of obesity (adipositas), hypercholesterolemia, diabetes, hyperglycaemia, diarrhoea, a bile disorder, a renal disorder. Also envisaged, and not limiting are the amelioration, prevention and/or treatment of gout, hypertension, cancer and/or a disorder related to the deposition of urate crystals in joints, soft tissue and/or the urinary tract.

The most common disorder of metabolism to be treated, prevented and/or ameliorated in accordance with this invention is obesity and/or a disorder which involves higher levels of triglycerides and/or cholesterol in the blood of a patient to be treated. The recommended level of triglycerides (in a normal range) are in males 40-160 mg/dL and in females 35 to 135 mg/dL. The recommended level of cholesterol (in a normal range) are 150-220 mg/100 ml.

Inter alia, the present invention provides for means and methods for the medical intervention in overweight subject, in particular human patients.

An "overweight" patient is often defined as having a body mass index (BMI) above 25 kg/m$^2$. Accordingly, the patients to be treated in accordance with this invention have a body mass index between 25 to 30 kg/m$^2$. However, it is also envisaged that patients are to be treated who have a BMI above 30 kg/m$^2$. In certain medically indicated cases, it is also envisaged that patients with a BMI below 25 kg/m$^2$ are to be treated with the peptides and/or nucleic acid molecules encoding the name as defined herein (or a pharmaceutically acceptable salt thereof) in order to reduce their body weight.

Accordingly, the present invention provides for the use of the peptides as defined herein (or a pharmaceutically acceptable salt thereof) for preventing or treating obesity, adipositas, eating disorders leading to increased body weight/body mass. Also envisaged are disorders related to higher or pathologically high body weight due to the use of drugs (like corticosteroids, antipsychotic drugs, antidepressants, particularly tricyclic antidepressants, oral contraceptives, etc.)

Disorders of the metabolism linked to higher body weight/body mass and to be treated (or prevented) by the administration of the peptides as defined herein (or a pharmaceutically acceptable salt thereof) may also comprise, but are not limited to, glycogen storage diseases, lipid storage diseases (like, e.g., Gaucher, Niemann Pieck), endocrine disorders (like, e.g., Cushings, hypothyroidism, insulinomas, lack of growth hormone, diabetes, adrenogenital syndrome, diseases of the adrenal cortex), tumors and metastases (such as craniophryngeomas), Prader-Willi syndrome, Down syndrome and genetic diseases and syndromes (like, e.g., hyperlipoproteinemias) or hypothalmic disorders.

Therefore, the invention also relates to the use of the peptides as defined herein (or a pharmaceutically acceptable salt thereof) in the amelioration, prevention and/or treatment of diseases/disorders related to, caused by or leading to higher or pathologically high body weight.

In accordance with this invention it is also envisaged that the peptides as defined herein (or a pharmaceutically acceptable salt thereof) are employed in the medical intervention of secondary disorders related to a (pathological) increase of body weight. These "secondary disorders" may comprise, but are not limited to diabetes type 2, high blood pressure (hypertension), cardiovascular diseases, stroke, cancer, problems with sexual function and disorder of the muscular or bone system. Said cardio-vascular disorder may comprise infarcts and/or stroke.

Accordingly, the peptides as defined herein (or pharmaceutically acceptable salts thereof) may be used, especially when administered to the small intestine, to influence the absorption of nutrients, absorption of bile acids, level of cholesterol in the blood, absorption of nucleosides, gout, secretion and/or motor function. Without being bound to theory, this influence may be due to:

(a) Inhibition of the sodium-serotonin cotransporter SERT (see, e.g. Chen (2004), Pflugers Arch. 447, 519-531.; Acc. No.: NM 001045) which is expressed in enteric ganglia cells and causes the termination of the serotonin induced activation of the enteric system (Chen (2001), The Journal of Neurosciences 21, 6348-6361.);

(b) Inhibition of organic cation transporters which are also expressed in enteric ganglia cells and which support the function of SERT (Chen (2001), The Journal of Neurosciences 21, 6348-6361);

(c) Inhibition of SGLT3 which controls secretion in the gut and motor function of the gut (Dies-Sampedro (2003), Proc. Natl. Acad. Sci. USA 100, 11753-11758.); and (d) Influencing organic cation transporters (e.g. SLC22A1/hOCT1, Acc. No X98332, U77086; SLC22A2/hOCT2, Acc. No X98333; SLC22A3/hOCT3/hEMZ, Acc. No. AJ001417; Koepsell (2004), Pflugers Arch. 447, 666-676.)

Furthermore, the peptides as defined herein (or pharmaceutically acceptable salts thereof) may be used, especially when administered to the colon, to influence absorption of water (for example, a laxative effect is induced) and/or motor function of the gut. This influence may be related to the modifications of the corresponding transporters (e.g. solute transporters, aquaporins, SERT and organic cation transporters).

Moreover, the peptides as defined herein (or pharmaceutically acceptable salts thereof) may be used, especially when administered to the kidney, in particular the proximal tubules (where, e.g. PEPT1 and PEPT2 are expressed), to inhibit reabsorption of D-glucose in diabetic patients, by, e.g. inhibition of SGLT1. As a consequence, there is an increased excretion of D-glucose, especially when high concentrations of D-glucose occur in the blood. Accordingly, the peptides as defined herein (or pharmaceutically acceptable salts thereof) may be used to decrease high peaks of glucose within the serum of diabetic patients, in particularly diabetic patients being adjusted insufficiently.

Additionally, the peptides as defined herein (or pharmaceutically acceptable salts thereof) may be used to inhibit function of transporters of endothelial cells.

It is envisaged that the herein defined RS1 fragment, e.g. the Q-C-P peptide described herein, interacts, in vivo, with peptide receptors, transporters and/or channels for peptides; receptors, transporters and/or channels for nucleosides or nucleotides; receptors, transporters and/or channels for sugars or sugar phosphates; receptors, transporters and/or channels for amino acids or taurine; receptors, transporters and/or channels for neurotransmitters or monoamines; receptors, transporters and/or channels for vitamins or cofactors; receptors, transporters and/or channels for urea, creatinine or ammonium; receptors, transporters and/or channels for organic ions or zwitterions; receptors, transporters and/or channels for anorganic ions, metal ions or protons; receptors, transporters and/or channels for drugs; receptors, transporters and/or channels for bile acids or fatty acids; and water channels. Said receptors, transporters and/or channels are well known in the art and, e.g. may comprise PAT1 (SLC36A1, acc. No. AF516142) PAT2 (SLC36A2 acc. no. AY162214) (Boll (2004), Pflugers Arch. 447, 776-779); EAAC1 (SLC1A1, acc. no. NM_004170, ASCT2 (SLC1A5, acc. No. U53347 or NM_005628) (Kanai (2004), Pflugers Arch. 447, 469-479); rBAT (SLC3A1 acc. No. L11696), 4F2hc (SLC3A2 acc. no. NM_002394) Palacin (2004), Pflugers Arch. 447, 490-494); AE3 (SLC4A3 acc. No. NM_005070), NBCe1 (SLC4A4 acc. no. NM_003759), NBCn1 (SLC4A7 acc. no. NM_003615) (Rmero (2004), Pflugers Arch. 447, 495-509); SGLT1 (SLC5A1 acc. no. NM_000343), SGLT2 (SLC5A2 acc. no. NM_003041), SGLT3 (SLC5A4 acc. no. NM_14227), NIS (SLC5A5 acc. no. NM_000453), SGLT4 (SLC5A8 acc. no. HCT1951464) (Wright (2004), Pflugers Arch. 447, 510-518); GAT1 (SLC6A1 acc. no. NM_003042), NET (SLC6A2 acc. no. NM_001043), DAT (SLC6A3 acc. no. NM_001044), SERT (SLC6A4 acc. no. NM_001045), GLYT2 (SLC6A5 acc. no. AF085412 and NM_004211), TAUT (SLC6A6 acc. no. NM_003043) (Chen (2004), Pflugers Arch. 447, 519-531); CAT-1 (SLC7AI acc. no. NM_004513 or NM_003045), y+LAT2 (SLC7A6 acc. no. D87432 or NM_003983), y+LAT1 (SLC7A7 acc. no. AF092032 or NM_003982), LAT2 (SLC7A8 acc. no. Y18483 or NM_012244), b0, +AT (SLC7A9 acc. no. AF141289 or NM_014270), Asc-1 (SLC7A10 acc. no. AB037670 or NM_019849) (Verrey (2004), Pflugers Arch. 447, 532-542); NHE2 (SLC9A2 acc. no. NM_003048), NHE3 (SLC9A3 acc. no. NM_004174), NHE4 (SLC9A4 acc. no. XM_087199) (Orlowski (2004), Pflugers Arch. 447, 549-565); ASBT (SLC10A2 acc. no. NM_000452) (Hagenbuch (2004), Pflugers Arch. 447, 566-570); NKCC2 (SLC12A1 acc. no. NM_000338), NCC (SLC12A3 acc. no. NM_000339) (Hebert (2004), Pflugers Arch. 447, 580-593); NaS1 (SLC13A1 acc. no. AF260824), NaC1 (SLC13A2 acc. no. U26209), NaC2 (SLC13A3 acc. no. AF154121) (Markovich (2004), Pflugers Arch. 447, 594-602); UT-B1 (SLC14A1 acc. no. NM_015865), UT-A1 (SLC14A2 acc. no. AF349446), UT-A2 (SLC14A2 acc. no. NM_007163) (Shayakul (2004), Pflugers Arch. 447, 603-609); MCT5 (SLC16A4 acc. no. NM_004696), MCT2 (SLC16A7 acc. no. NM_004731), TAT1 (SL16A10 acc. no. NM_018593) (Halestrap (2004), Pflugers Arch. 447, 619-628); NPT1 (SLC17A1 acc. no. NM_005074), NPT3 (SLC17A2 acc. no. U90544), NPT4 (SLC17A3 acc. no. NM_006632), AST (SLC17A5 acc. no. AJ387747) (Reimer (2004), Pflugers Arch. 447, 629-635); OATP4C1 (SLC21A20 acc. no. AY273896) (Hagenbuch (2004), Pflugers Arch. 447, 653-665); hOCT1 (SLC22A1 acc. no. X98332 and U77086), hOCT2 (SLC22A2 acc. no. X98333), hOCT3 (SLC22A3 acc. no. AJ001417), hOCTN1 (SLC22A4 acc. no. AB007448), hOCTN2 (SLC22A5 acc. no. AF057164), hOAT1 (SLC22A6 acc. no. AF057039), hOAT2 (SLC22A7 acc. no. AF210455 and AF097518 and AY050498), hOAT3 (SLC22A8 acc. no. AF097491), hOAT4 (SLC22A11 acc. no. AB026116) (Koepsell (2004), Pflugers Arch. 447, 666-676); Sat-1 (SLC26A1 acc. no. AF297659), DRA (SLC26A3 acc. no. NM_000111), Pendrin (SLC26A4 acc. no. NM_000441), SLC26A7 acc. no. AF331521 (Mount (2004), Pflugers Arch. 447, 710-721); FATP2 (SLC27A2 acc. no. NM_003041), FATP3 (SLC27A3 acc. no. NM_024330), FATP4 (SLC27A4 acc. no. NM_005094), FATP5 (SLC27A5 acc. no. NM_012254) (Stahl (2004), Pflugers Arch. 447, 722-727); CNT1 (SLC28A1 acc. no. NM_004213), CNT2 (SLC28A2 acc. no. NM_004212), CTN3 (SLC28A3 acc. no. NM_022127) (Gray (2004), Pflugers Arch. 447, 728-734); ENT1 (SLC29A1 acc. no. NM_004955), ENT2 (SLC29A2 acc. no. NM_001532) (Baldwin (2004), Pflugers Arch. 447, 735-743); NaPi-IIa (SLC34A1 acc. no. NM_003052), NaPi-IIb (SLC34A2 acc. no. NM_006424), NaPi-IIc (SLC34A3 acc. no. NM_080877) (Murer (2004), Pflugers Arch. 447, 763-767); SNAT2 (SLC38A2 acc. no. NM_018976), SNAT3 (SLC38A3 acc. no. NM_006841), SNAT4 (SLC38A4 acc. no. NM_018018), SNAT5 (SLC38A5 acc. no. NM_033518) (Mackenzie (2004), Pflugers Arch. 447, 784-795); hZIP4 (SLC39A4 acc. no. NM_017767), SLC39A5 acc. no, NM_173596 (Eide (2004) Pflugers Arch., 447:796-800); IREG1 (SLC40 acc. no. NM_000342) (McKie (2004), Pflugers Arch. 447, 801-806); RhBG (SLC42A2 acc. no. AF193807), RhCG (SLC42A3 acc. no. AF193809) (Nakhoul (2004), Pflugers Arch. 447, 807-812); hENaC α-subunit (acc. no. AH007622 or L29007), McDonald (1994), Am. J. Physiol. 266, L728-L734) or hENaC β-subunit (acc. no. L36593), hENaC γ-subunit (acc. no. L36592) (McDonald (1995), Am. J. Physiol. 268, 1157-1163).

Moreover, the RS1 fragment as used within the present invention may interact with a receptor, transporter and/or channel in the kidney, for example the $Na^+$-D-glucose cotransporter SGLT1, and/or in the skin, for example the organic cation transporter hOCT3.

In accordance with the present invention, it is also envisaged that the peptides as defined herein (or pharmaceutically acceptable salts thereof) may be used to prevent, ameliorate and/or treat pathophysiological conditions such as stroke, myocardial infarction, acute renal failure and/or ischemia/reperfusion injury (which may or may not caused by pathophysiological conditions such as stroke, myocardial infarction and/or acute renal failure). Thereby, and by other uses, the peptides as defined herein (or pharmaceutically acceptable salts thereof may interact with receptors, transporters and/or channels of one or more regulatory pathways. E. g. these receptors, transporters and/or channels are the receptors, transporters and/or channels as defined herein, e.g. the afore mentioned receptors, transporters and/or channels for neurotransmitters, monoamines, anorganic ions or organic zwitterions, cations and anions, like, e.g. receptors, transporters and/or channels for glutamate. An interaction of different regulatory pathways, all or less than all of which are intended to be influenced by the peptides as defined herein (or pharmaceutically acceptable salts thereof), may also be given.

Without being bound by theory, one of the regulatory pathways to be influenced by the peptides as defined herein (or pharmaceutically acceptable salts thereof may be a pathway that regulates the appetite sensation and/or the feeding/eating behaviour of a subject. E. g. this pathway involves the function of RS1, the associated protein IRIP (Jiang (2005), Mol. Cell Biol. 25 (15), 6496-508), includes or is modulated by protein kinase C and requires intact dynamin (Veyhl (2003), J. Membr. Biol. 196, 71-81).

Again, without being bound by theory, it is also envisaged that the peptides as defined herein (or pharmaceutically acceptable salts thereof) may also be used for modulating appetite of a subject. Without bound to theory, appetite of a subject may also arise with decreasing glucose concentration in the blood. Therefore, the peptides as defined herein (or pharmaceutically acceptable salts thereof) may also be used as appetite enhancers, e.g. for the amelioration, prevention and/or treatment of bulimia, anorexia nervosa and the like.

However, the use of the peptides as defined herein (or pharmaceutically acceptable salts thereof) as appetite suppressors is also envisaged.

It is also envisaged that the peptides as defined herein (or pharmaceutically acceptable salts thereof) also interact with further factors. Such factors are well known in the art and comprise factors like the factors described in Jiang (2005) Mol Cell Biol. 25 (15), 6496-508, Veyhl (2004) J Membr Biol 196, 71-81 and Osswald (2005) Mol Cell Biol 78-87. The interaction with such factors may facilitate or inhibit the interaction of the peptides as defined herein (or pharmaceutically acceptable salts thereof) with the receptors, transporters and/or channels defined herein, and may also not influence said interaction. For instance, the peptides as defined herein (or pharmaceutically acceptable salts thereof) may interact with the ischemia/reperfusion-inducible protein IRIP (Jiang, 2005, Mol Cell Biol., 25(15): 6496-508; AY286019/ AY286020). This interaction may increase the inhibitory influence of the peptides as defined herein (or pharmaceutically acceptable salts thereof) on receptors, transporters and/or channels as defined herein. For example, said receptors, transporters and/or channels are receptors, transporters and/or channels for organic cations or anions, like, e.g. hOCT1 (SLC22 µl acc. no. X98332 and U77086), hOCT2 (SLC22A2 acc. no. X98333), hOCT3 (SLC22A3 acc. no. AJ001417) or hOAT1 (SLC22A6 acc. no. AF057039), hOAT2 (SLC22A7 acc. no. AF210455 and AF097518 and AY050498) and hOAT3 (SLC22A8 acc. no. AF097491), hOAT4 (SLC22A 11 acc. no. AB026116) (Koepsell (2004), Pflugers Arch. 447, 666-676).

As used herein, the term "receptor(s), transporter(s) and/or channel(s)" relates to all kind of proteins that are capable to interact with RS1 and/or a RS1 fragment or a derivative thereof as defined herein above. Further, this term relates to proteins that interact with a substrate to be transported or to be recognized. Those proteins are well known in the art (see, e.g. Wright (2004) Pflugers Arch., 447:510-518).

These receptor, transporter and/or channel proteins are preferably membrane proteins that are known in the art (see e.g. Stryer, Biochemistry, Ed. 4th, 1995, chapter 11). However, they may also contain peripheral subunits or components (see e.g. Stryer, Biochemistry, Ed. 4th, 1995, page 275).

It is also envisaged that the peripheral components of receptors, transporters and channels may be cytosolic or extra cellular proteins and that receptors may cytosolic in total.

The transporters may comprise active cotransporters like sym- or antiporters, passive transporters (e.g. like some transporters of pharmaceutical compositions or some ion-channels) or channels (e.g. like aquaporins).

The derivatives of the peptides as defined herein (or also pharmaceutically acceptable salts of such derivatives) that can permeate through biological membranes may be used to inhibit function of transporters within the skin. Accordingly, these peptides can be used to treat proliferative disorders of the skin as e.g. tumors/cancer.

The most common pharmaceutical salt employed in patients, in particular human patients is the hydrochloride form, i.e. hydrochloride of the peptides as defined herein (or derivatives thereof). Hydrochloride of the peptides as defined herein is also a preferred salt in context of this invention. Yet, also other salts are known and envisaged. These comprise, but are not limited to acid addition salts, like acetate, adipate, alginate, ascorbate, aspartate, benzoate, benzenesulfonate, bisulphate, butyrate, citrate, cyclopentanepropionate, digluconate, dodecyl sulphate, ethane sulfonate, fumarate, glucoheptanoate, glycerophosphate, heptanoate, hexanoate, hydrochloride, 2-hydroxyethane sulfonate, lactate, maleate, methane sulfonate, nicotinate, nitrate, oxalate, pamoate, pectinate, persulphate, 3-phenyl sulfonate, 3-phenylpropionate, phosphate, propionate, salicylate, succinate, sulphate, sulfonate, tartrate, undecanoate, or the like.

The pharmaceutical compositions described herein can be administered to the subject at a suitable dose. Administration of the suitable compositions may be effected by different ways, e.g., by intravenous, intraperitoneal, intravesical subcutaneous, by inhalation as well as transdermal administration. Preferred are oral administrations (also in form of food, feed and/or food additives as described herein). However, in patients and in particular medical uses, another preferred administration route is (are) blood infusion(s) (like intravenous ionfusion(s)) and/or rectal administration (e.g. in form of enemas or suppositories).

The peptides as defined herein may, accordingly, be administered orally, parenterally, such as subcutaneously, intravenously, intramuscularly, intraperitoneally, intrathecally, transdermally, transmucosally, transpulmonally subdurally, locally or topically via iontopheresis, sublingually, by inhalation spray, aerosol or rectally and the like in dosage unit formulations optionally comprising conventional pharmaceutically acceptable excipients.

Pharmaceutical compositions comprising a peptide/RS1 fragment according to the present invention for oral use can be obtained by combining the active compound(s) with solid excipient, optionally grinding the resulting mixture, and processing the mixture of granules, after adding suitable auxiliaries, if desired, to obtain tablets or dragée cores, preferably with a gastric juice resistant coating such as derivatives of cellulose, polymer of methacrylic acid and methacrylic acid esters or derivatives of polyvinyl.

In accordance with this invention, the peptides described herein (or their derivatives) to be administered in particular in form of a pharmaceutical composition (or also in form of a food supplement) may be comprised in tablets/pills and the like. In a preferred embodiment, said peptides are comprised in coated, e.g. film-coated tablets/pills. Such a coating is particularly preferred for time- and/or location-controlled release of the peptides (or nucleic acid molecules encoding the same). Corresponding coatings are known in the art, and, inter alia, described in EP-A1 0 109 320, WO 94/06416, EP-A1 0 630 646 or EP-A1 0 548 448.

It is envisaged within the present invention, that the pharmaceutically acceptable carrier as employed herein warrants the release of the peptides as defined herein within the small intestine, the renal proximal tubules, the colon, the rectum, or the bladder and/or the blood vessels. Preferred are the small intestine, the renal proximal tubules and/or the colon, most preferred is the small intestine.

Particularly preferred coatings in this respect are coatings which lead to a resistance to gastric juices and, accordingly, the peptide as provided herein is liberated in the gut/intestine, preferably in the small intestine and/or the colon. Accordingly, gastric juice resistant coatings may preferably be employed. Such coatings are known in the art and comprise, as non-limiting examples: cellulose derivatives, like carboxymethylene ethylcellulose (Aquateric®), cellulose acetatephthalate (HP50®) or hydroxypropylene cellulose methylphthalate (HP55®); polymeric compounds derived from methacrylic acid and methacrylic acid esters, like Eutragit® L and Eutragit® S (for retard forms Eutragit® RL und Eutragit® RS).

Also polyvinyl derivatives may be used. These comprise, inter alia, polyvinylpyrrolidone (e.g. Kollidon®) polyvidone acetate or polyvinyl acetate phthalate (e.g. Opadry®).

The peptides according to the present invention (or salts thereof) or medicaments comprising them, intended to be administered intracellulary may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered near the cell surface.

Delivery systems involving transfersomes, niosomes and liposomes in pharmaceutical uses are well established, and the person skilled in the art is readily in a position to prepare corresponding transfersomes, niosomes and liposomes comprising the herein defined peptides, nucleic acid molecules encoding the same or vectors comprising said nucleic acid molecules. Methods are, inter alia, provided in Müller/Hildebrand "Pharmazeutische Technologie: Moderne Arznei", WVG. Wiss Verlag, Stuttgart (1998); Gupta (2005), Int. J. Pharm. 293, 73-82; Torchilin (2005), Nat. Rev. Drug Discov. 4, 145-160.

Nucleic acid molecules may also be administered to patients in need of treatment via transferosomes, liposomes and/or niosomes. Corresponding preparation methods are known in the art, see, inter alia, Mahoto (2005), Adv. Drug Deliv. Rev. 57, 699-712 or Kawakami (2004), Pharmazie. 59, 405-408.

Also nanoparticles may be used as delivery systems for the peptides as defined herein and/or nucleic acid molecules encoding the same. Nanoparticles have been developed as an important strategy to deliver peptides and more recently nucleotides. Nanoparticles and other colloidal drug delivery systems modify the kinetics, body distribution and drug release of an associated drug. Corresponding technologies are, inter alia, described and referenced in Kayser (2005), Curr. Pharm. Biotechnol. 6(1), 3-5 or Moghimi (2005), FASEB J. 19, 311-330.

Furthermore, in particular when peptides or protein stretches are to be administered in accordance with this invention, hydrogels may be employed. Corresponding methods are provided and summarized in Pappas (2004), Expert Opin. Biol. Ther. 4, 881-887. Hydrogels are particularly useful in the transmucosal (mostly oral) administration/delivery of therapeutic proteins or peptides, as provided herein.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, the pharmaceutical composition described herein may comprise further agents depending on the intended use of the pharmaceutical composition.

It will be appreciated by the person of ordinary skill in the art that the peptides/RS1 fragments described herein and the additional therapeutic agent may be formulated in one single dosage form, or may be present in separate dosage forms and may be either administered concomitantly (i.e. at the same time) or sequentially.

The pharmaceutical compositions comprising the peptides as defined herein may be in any form suitable for the intended method of administration.

Pharmaceutically useful excipients that may be used in the formulation of the pharmaceutical compositions comprising the peptides as defined herein (or a salt thereof) may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintergrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins. Other suitable pharmaceutically acceptable excipients are described in Remington's Pharmaceutical Sciences, 15$^{th}$ Ed., Mack Publishing Co., New Jersey (1991).

The dosage regimen of the pharmaceutical compositions as defined herein will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Dosage forms for oral administration include tablets, capsules, lozenges, pills, wafers, granules, oral liquids such as syrups, suspensions, solutions, emulsions, powder for reconstitution. Dosage forms for parentral administration include aqueous or olegeous solutions or emulsions for infusion, aqueous or olegeous solutions, suspensions or emulsions for injection pre-filled syringes, and/or powders for reconstitution. Dosage forms for local/topical administration comprise rectal suppositories, insufflations, aerosols, metered aerosols, transdermal therapeutic systems and/or medicated patches.

The amount of peptides as defined herein (or a pharmaceutically acceptable salt thereof) that may be combined with the excipients to formulate a single dosage form will vary upon the host treated and the particular mode of administration.

The pharmaceutical compositions of the invention can be produced in a manner known per se to the skilled person as described, for example, in Remington's Pharmaceutical Sciences, 15$^{th}$ Ed., Mack Publishing Co., New Jersey (1991).

For the purpose of the present invention, a (therapeutically) effective dosage of the peptides/RS1 fragments as defined herein (or a pharmaceutically acceptable salt thereof may be a concentration of said peptides of between $2 \times 10^{-9}$ M to 5 M, preferably between $2 \times 10^{-7}$ M to 3 M, more preferably between $2 \times 10^{-6}$ M to 1 M, more preferably between $2 \times 10^{-6}$ M to 0.5 M, more preferably between $2 \times 10^{-5}$ M to 0.1 M, more preferably between 20-30 mM, even more preferably between 2-10 mM and most preferably between 5-10 mM. However, also concentrations between 2-3 mM are envisaged in context of the present invention. E.g., in the small intestine, the (therapeutically) effective dosage of the peptides as defined herein (or a pharmaceutically acceptable salt thereof is a concentration of said peptides between 5-10 mM, but also the afore-mentioned other concentrations can occur in the small intestine. The person skilled in the art is readily in a position to deduce such concentrations, e.g. in vivo or ex vivo. Samples may be from the small intestine by a duodenal probe and the peptide(s) as described herein may be detected and their corresponding concentrations may be determined in said given sample, for example by HPLC.

The determination of the peptide concentration may be obtained in human patients, healthy (human) individuals as well as in animals, like laboratory animals, non-human transgenic animals (e.g. transgenic mice, rats, pigs, and the like). It is envisaged that the determination of "peptide concentrations" in the gastro-intestinal tract, e.g., the gut duodenum, may for example be deduced in healthy volunteers and corresponding administration schemes for human patients/healthy humans may be established. For example, the gut passage time, the passage of the peptide in the gastro-intestinal tract, the dosage dependencies (e.g. oral dosage given versus dosage detected in various regions of the gastro-intestinal tract) may be determined by standard methods known in the art. Further methods comprise, but are not limited to, the detection of labelled peptides in vivo (e.g. by corresponding labelling techniques, like radioactive labelling, fluorescent labelling, etc.) or physiological/biochemical assays. Accordingly, the dosage of peptides to be given orally in order to obtain a desired concentration of the herein described peptides in any part of the gastro-intestinal tract, like the gut duodenum, may be deduced. These and other methods to deduce such concentrations are well known in the art.

It is envisaged that, for example, the extra cellular concentrations of the peptides as defined herein (or a pharmaceutically acceptable salt thereof) may rise up to 0, 5, 1, 2, 3, 4 or 5 M. Especially in the gut (where, e.g. very high concentration of sugars (for example after consumption of sweets) may occur), said concentrations may reach those high levels. Without bond to theory, the transport capacity of the herein defined peptide-transporters is saturated at a concentration of the peptides as defined herein (or a pharmaceutically acceptable salt thereof) of about 100 mM. Accordingly, it is envisaged that the extra cellular concentration of said peptides is, e.g., at about 100 mM. However, as documented in the appended examples, physiological effects of the peptides defined herein could be deduced at concentrations of about 5 mM in the extracellular medium. Accordingly, corresponding compositions, e.g. compositions comprised in foods and beverages, food supplements, pharmaceutical compositions, and the like should comprise the peptides as defined herein in concentrations that in vivo an extracellular concentration of the peptides (e.g. in humans) be in the range of at least 0.5 mM, 1 mM, 2 mM, 3 mM, 4 mM and in particular at least 5 mM. E. g., said concentration in said corresponding compositions, e.g. compositions comprised in foods and beverages, food supplements, pharmaceutical compositions (e.g. in form of tablets), and the like, may be in the range of 0.1 to 3 M.

It will be appreciated, however, that specific dose level of the "Q-C-P peptide"/"RS1 fragment" as defined herein for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgement of the ordinary clinician or physician. For example, a certain (relatively high) amount of peptide (e.g. 5 g) could be applied to a subject, the (relatively lowered) corresponding peptide concentration (e.g. 5-10 mM) occurring in the subject (e.g. in the blood or mucosa of the small intestine) could be measured and, optionally, said corresponding peptide concentration could be compared with a detected effect (e.g. glucose uptake into mucosal cells (detected, e.g., by tracing radioactively marked glucose)).

As pointed out above, in a further aspect and in another embodiment of the present invention, the preparation of food, feed, "functional food", "food supplements" as well as "food additives" is provided. Therefore, the present invention is not limited to medical and/or pharmaceutical uses. The invention also relates to the use of a regulatory protein RS1 fragment as defined herein or a nucleic acid molecule encoding said regulatory protein RS1 fragment for the preparation of food and/or food supplements, wherein said RS1 fragment is characterized in comprising at least the amino acid sequence Q-C-P (Glutamine-Cysteine-Proline) or derivatives thereof (e.g. like QSP, QPP or QTP) and/or 3consecutive amino acids as comprised in the amino acid stretch SDSDRIEP (SEQ ID NO: 9) or derivatives thereof. Again, the description of the Q-C-P peptides and/or derivatives provided in context of the above recited methods and uses apply here mutatis mutandis.

In accordance with this embodiment of the invention, the preparation of food "functional food", "food supplements" as well as "food additives" is provided. The food "functional food", "food supplements" as well as "food additives" may be carbohydrate- and/or fat-rich and/or may have a high glycemic index. It is also envisaged that the food "functional food", "food supplements" as well as "food additives" is carbohydrate- and/or fat-low and/or has a low glycemic index. Accordingly, the invention provides for "functional food" and/or "functional food supplements/additives" comprising the herein defined RS1 minimal peptides (or (a) combination(s) thereof). These "functional food" and/or "functional food supplements/additives" are particularly useful since the sugar and/or fat intake/uptake is inhibited or at least downregulated due to the use of the herein defined "Q-C-P peptides"/"RS1 fragments".

As documented in the appended examples, the present invention, i.e. the use of the "Q-C-P peptides"/"RS1 fragments" as defined herein, is particularly useful in the prevention of sugar-in/uptake (for example in/uptake of monosaccharides, like glucose, fructose) in cells. As is shown in the appended examples, the RS1 fragments as described herein, e.g. the "Q-C-P-tripeptide" and derivatives thereof, like Q-S-P, Q-T-P, Q-P-P, can be employed in the physiological (in vivo) inhibition of cellular uptake of monosaccharides (e.g. glucose, fructose). It was, inter alia, found that the corresponding biological/physiological effect is particular striking in cells with either low (e.g less than 50 µM) or high (e.g more than 5 mM) intra-cellular concentration of sugar, e.g. glucose or fructose.

Accordingly, as mentioned herein, the present invention is particular useful in food, feed and/or food supplements being carbohydrate-rich or -low and/or fat-rich or -low and/or having a high or low glycemic index, as well as useful for the prevention/inhibition of sugar-in/uptake during diets using said food, feed and/or food supplements. Therefore, the present invention is, inter alia, useful in food, feed and/or food supplements being carbohydrate-low and/or fat-low and/or having a low glycemic index or in diets comprising said food, feed and/or food supplements. As also demonstrated in the appended examples, the RS1 fragments as described herein are also to be employed in food, feed and/or food supplements being carbohydrate-rich and/or fat-rich and/or having a high glycemic index or in diets comprising said food, feed and/or food supplements.

However, it is of note that the present invention may also be useful for normal food, feed and/or food supplements as well as for normal diets.

It is envisaged, but not limited that the following "foods" or "food supplements/additives" being prepared in accordance with this invention are:

Bakery products such as cake, cookies, biscuits, doughnuts;
Meat products such as sausages, meat balls, Hamburgers, meat pies;
Cereal products such as cake mixtures, muffin mixtures;
Milk products such as yogurts, curd cheese mixtures, junkets, ice creams, cheeses, milkshakes;
Cacao-und chocolate products such as chocolate bars, chocolate coatings;
Alcoholic beverage such as liqueur, non-alcoholic beverage such as soft drinks;
Fruit products such as jams, jellies;
Confectionery such as jelly bears, marzipan, chewing gum, sugar syrup, sugar mass used for stuffing, candies, dessert powders;
potato products such as French fries, chips; or
fat und oil containing products such as mayonnaise, oleomargarine.

Also envisaged is the use of the herein defined "RS1 fragments" in fast food such as frozen foods, canned products or fried products.

Accordingly, the present invention also provides for dietetics, "novel food", "functional food" (foods with components whose positive effects can be regarded as physiological or even healthy), dietary supplements and/or wellness products (products with beneficial effects) comprising the herein defined "Q-C-P peptides"/"RS1 fragments" and/or peptides derived from the additional minimal RS1 stretch defined herein (SDSDRIEP (SEQ ID NO: 9) peptide). E.g., such "novel food", "functional food", dietary supplements and/or wellness products are in form of shakes, like, e.g. protein shakes. In accordance with the present invention, such shakes, but also the other "novel food", "functional food", dietary supplements and/or wellness products, may be carbohydrate-rich or -low and/or fat-rich or low and/or may have a high or low glycemic index. It is, for example, envisaged that the herein defined "Q-C-P peptides"/"RS1 fragments" are comprised in "functional food", food products, food supplements and/or wellness products with low carbohydrate and low fat content or in corresponding products with low glycemic index. However, it is also envisaged that the herein defined "Q-C-P peptides"/"RS1 fragments" are comprised in "functional food", food products, food supplements and/or wellness products with high carbohydrate and high fat content or in corresponding products with high glycemic index.

Corresponding "foods" or "food supplements/additives" are well known in the art (e.g. Belitz, Grosch, Scheiberle, Lehrbuch der Lebensmittelchemie, 5. Auflage, Springer.)

Therefore, the invention also provides for a method of preparation of food and/or food supplements/additives, comprising the step of admixing an RS1 fragment/"Q-C-P peptide" as defined herein above, a nucleic acid molecule as defined herein below and encoding for a RS1 fragment of the invention (comprising the Q-C-P motive or a herein defined derivative) and/or a vector comprising such a nucleic acid molecule with food basics and/or foodstuff. "Food basics" and "foodstuff" are known in the art.

In accordance with the present invention, the terms "feed", "foods", "foodstuff" and/or "food basics" encompasses all eatable and drinkable food and drinks. Accordingly, the herein defined "Q-C-P-peptide" may be included in a food or drink. These may, for example be, gum, spray, beverage, candies, infant formula, ice cream, frozen dessert, sweet salad dressing, milk preparations, cheese, quark, lactose-free yogurt, acidified milk, coffee cream or whipped cream and the like.

Milk-based products are envisaged within the framework of the invention. Milk is however understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

The food, drink or feed comprising the RS1 fragments as defined herein can be produced by a general method for producing foods and drinks or feeds, including adding the active ingredient to a raw or cooked material of the food, drink or feed. The food, drink or feed in accordance with the present invention can be molded and granulated in the same manner as generally used for foods, drinks or feeds. The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

The food, drink or feed according to the present invention includes foods, drinks or feeds comprising the active ingredient, namely the RS1 fragments as provided and described herein. The food, drink or feed to be used in the present invention includes any food, drink or feed. The concentration of the active ingredient, namely the RS1 peptide fragment as defined herein is preferably 0.001 to 100% by weight, more preferably 0.01 to 50% by weight, even more preferably 0.1 to 25% by weight and most preferably 1 to 25% by weight of the food, drink or feed comprising such active ingredient. The concentration of the active ingredient, namely the RS1 peptide fragment as defined herein may also be 5% by weight of the food, drink or feed comprising such active ingredient. For example, a drink containing 100 ml with 5 g of the active ingredient, namely the RS1 fragments as provided and described herein, is employed in accordance with the present invention.

Specific foods or drinks, to which the active ingredient is added, include, for example, juices, refreshing drinks, shakes, like e.g. protein shakes, soups, teas, sour milk beverages, dairy products such as fermented milks, ices, butter, cheese, processed milk and skim milk, meat products such as ham, sausage, and hamburger, fish meat, cake products, egg products such as seasoned egg rolls and egg curd, confectioneries such as cookie, jelly, snacks, and chewing gum, breads, noodles, pickles, smoked products, dried fishes and seasonings. The form of the food or drink includes, for example, powder foods, sheet-like foods, bottled foods, canned foods, retort foods, capsule foods, tablet foods and fluid foods.

The food or drink with the RS1 fragments as provided and described herein may be also a food or drink, comprising e.g milk, chocolate, beer, vine, butter, cheese and the like.

The food or drink with the RS1 fragments as provided and described herein may be also ingested by infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion.

The nutritious composition in accordance with the present invention is principally composed of protein, lipid, saccharide, vitamins and/or minerals. In the nutritious composition, the active ingredient is blended with these components.

The protein includes milk proteins such as skim milk, casein, cheese whey, whey protein concentrate and whey protein isolates and their fractions such as alpha s-casein, beta-casein, alpha-lactoalbumin and beta-lactoglobulin. Further, egg protein such as egg yolk protein, egg white protein, and ovalbumin, or soybean protein such as defatted soybean protein, separated soybean protein, and concentrated soybean protein can be used. Other than these, proteins such as wheat gluten, fish meat protein. cattle meat protein and collagen may also be used satisfactorily. Further, fractions of these proteins, peptides from the acid or enzyme treatment thereof, or free no acids maybe used satisfactorily as well. The free amino acids can serve as nitrogen sources and can additionally be used to give specific physiological actions. Such free amino acids include, for example, taurine, arginine, cysteine, cysteine and glutamine. The lipid includes animal fats and oils such as milk, fat, lard, beef fat and fish oil, vegetable oils such as soybean oil. rapeseed oil, corn oil, coconut oil, palm oil, palm kernel oil, safflower oil, perilla oil, linseed oil, evening primrose oil, medium chain fatty acid triglyceride, and cotton seed oil, bacterially generated fats and oils, and fractionated oils thereof, hydrogenated oils thereof, and ester exchange oils thereof. The amount of lipid to be blended varies depending on the use.

The saccharide/sugars includes, for example, one or more of starch, soluble polysaccharides, dextrin, monosaccharides such as sucrose, lactose as described herein, maltose, glucose, and fructose and other oligosaccharides. The total amount of such saccharide may be 10 to 80% by weight to the total solid in the nutritious composition. Further, artificial sweeteners such as aspartame may be used satisfactorily. The amount of an artificial sweetener is appropriately 0.05 to 1.0% by weight per the total solid in the nutritious composition.

The vitamins include, but are not limited to, lycopene as an essential component and additionally include, for example, vitamins such as vitamin A, vitamin B group, vitamins C, D, and E and vitamin K group, folic acid, pantothenic acid, nicotinamide, carnitine, choline, inositol and biotin as long as such vitamins can be administered to infants. Such vitamins are preferably from 10 mg to 5 g by weight per the total solid in the nutritious composition.

Further, the minerals include calcium, magnesium, potassium, sodium, iron, copper, zinc, phosphorus, chlorine, manganese, selenium and iodine. Such minerals are preferably from 1 mg to 5 g by weight per the total solid in the nutritious composition. Other than those components described above, the foods, drinks, nutritious composition for of the present invention may be blended with any component desirably blended in nutritious compositions, for example, dietary fiber, nucleotides, nucleic acids, flavors, and colorants.

The food or drink of the present invention can be used as a health food or drink or a functional food or drink to prevent and/or treat caries.

When the food or drink according to the present invention is ingested, the amount to be ingested is not specifically limited. The amount to be ingested is generally 0.1 to 50 g, preferably 0.5 g to 20 g daily, based on the total amount of active ingredient. The food or drink is continuously ingested at this amount for a period from a single day up to 5 years, preferably from 2 weeks to one year. Herein, the amount ingested can be adjusted to an appropriate range depending on the severity of the symptom of the individual ingesting the food or drink, the age and body weight thereof, and the like.

The feed of the present invention maybe any feed comprising the active ingredient. The feed includes, for example, pet feed for dogs, cats and rats, cattle feed for cows and pigs, chicken feed for chicken and turkeys, and fish cultivation feed for porgy and yellowtail.

The food, feed and nutrients can be produced by appropriately blending the active ingredient of the present invention in a raw feed material including, for example, cereals, brans, oil-seed meals, animal-derived raw feed materials, other raw feed materials and purified products.

The cereals include, for example, mile, wheat, barley, oats, rye, brown rice, buckwheat, fox-tail millet, Chinese millet, Deccan grass, corn, and soybean.

The brans include, far example, rice bran, defatted rice bran, bran, lowest-grade flour, wheat germ, barley bran, screening pellet, corn bran, and corn germ.

The oil-seed meals include, for example, soybean meal, soybean powder, linseed meal, cottonseed meal, peanut meal, safflower meal, coconut meal, palm meal, sesame meal, sunflower meal, rapeseed meal, kapok seed meal and mustard meal.

The animal-derived raw feed materials include, for example, fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill.

Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chlorella.

The purified products include, for example, proteins such as casein and albumin, amino acids, starch, cellulose, saccharides such as sucrose and glucose, minerals and vitamins, Furthermore, the present invention relates to an additive for food, drinks and feed, which, due to the presence of the RS1 fragment as defined herein, inter alia, capable of specifically modifying, inter alia, glucose and/or amino acid transport. The additive for food can be produced by a general method for producing additives for food, drinks or feed. If necessary, additives for general use in food, drinks or feed, for example, additives described in Food Additive Handbook (The Japan Food Additives Association; issued on Jan. 6, 1997) may be added satisfactorily, including sweeteners, colorants, preservatives, thickeners and stabilizers, anti-oxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers mentioned previously for pharmaceutical tablets may be added satisfactorily.

The additives include the following additives.

The sweeteners include aspartame, licorice, stevia, xylose and rakanka (Momordica grosvenori fruit). The colorants include carotenoid and turmeric oleoresin, flavonold, caramel color, spirulina color, chlorophyll, purple sweet potato color, purple yam color, perilla color, and blueberry color.

The preservatives include, for example, sodium sulfite, benzoates, benzoin extract, sorbates, and propionates. The thickeners and stabilizers include, for example, gums such as gum arable and xanthan gum, alginates, chitin, chitosan, aloe extract, guar gum, hydroxypropyl cellulose, sodium casein, corn starch. carboxymethyl cellulose, gelatin, agar, dextrin, methyl cellulose, polyvinyl alcohol, microfiber cellulose, microcrystalline cellulose, seaweed cellulose, sodium polyacrylate, sodium polyphosphate, carrageenan or yeast cell wall.

The anti-oxidants include, for example, vitamin C group, sodium ethylenediaminetetraacetate, calcium ethylenediaminetetraacetate, erythorbic acid, oryzanol, catechin, quercetin, clove extract, enzyme-treated rutin, apple extract, sesame seed extract, dibutylhydroxytoluene, fennel extract, horseradish extract, water celery extract, tea extract, tocopherols, rapeseed extract, coffee bean extract, sunflower seed extract, ferulio acid, butylhydroxyanisole, blueberry leaf extract. propolis extract, pepper extract, garden balsam extract, gallic acid, eucalyptus extract, and rosemary extract.

The color fixing agents include, for example, sodium nitrite. The bleaches include, for example, sodium sulfite.

The antiseptics include, for example, o-phenyl phenol. The gum base includes, for example, acetylricinoleate methyl, urushi wax, ester gum, elemi resin, urucury wax, kaurigum, carnaubawax, glycerin fatty acid ester, spermaceti wax, copaibabalsam, copal resin, rubber, rice bran wax, cane wax, shellac, jelutong, sucrose fatty acid ester, depolymerized natural rubber, paraffin wax, fir balsam, propylene glycol fatty acid ester, powdered pulp, powdered rice hulls, jojoba oil, polyisobutylene, polybutene, microcrystalline wax, mastic gum, bees wax and calcium phosphate.

The bitters include, for example, iso-alpha-bitter acid, caffeine, kawaratake (Coriolus versieolor) extract, redbark cinchona extract, Phellodendron bark extract, gentian root extract, spice extracts, enzymatically modified naringin, Jamaica cassia extract, theabromine, naringin, cassia extract, absinth extract, isodonis extract, olive tea, bitter orange (Citrus aurantium) extract, hop extract and wormwood extract.

The seasonings include, for example, amino acids such as asparagine, aspartic acid, glutamic acid, glutamine, alanine, isoleucine, glycine, serine, cystine, tyrosine, leucine, and praline, nucleic acids such as sodium inosinate, sodium uridinate, sodium guanylate, sodium cytidylate, calcium ribonucleotide and sodium ribonucleotide, organic acids such as citric acid and succinic acid, potassium chloride, sodium chloride-decreased brine, crude potassium chloride, whey salt, tripotassium phosphate, dipotassium hydrogen phosphate, potassium dihydrogen phosphate, disodium hydrogen phosphate, sodium dihydrogen phosphate, trisodium phosphate and chlorella extract.

As discussed herein, it is also envisaged that microorganism express the "RS1 peptide(s) fragments" described herein and that these microorganism are employed in functional food and/or as pharmaceutical composition. Namely, in addition to the probiotic effect, the probiotic microorganism expressing the RS1 fragment described herein is useful for treating and/or preventing metabolic disorders and/or secondary disorders mentioned herein. The amount of said probiotic microorganism is high enough to significantly positively modify the condition to be treated, preferably obesity, diabetes and the like, but low enough to avoid serious side effects (at a reasonable benefit/risk ratio), within the scope of sound medical judgment. An effective amount of said probiotic microorganism will vary with the particular goal to be achieved, the age and physical condition of the patient being treated, the severity of the underlying disease, the duration of treatment, the nature of concurrent therapy and the specific microorganism employed. A decided practical advantage is that the probiotic organism may be administered in a convenient manner such as by the oral route. Depending on the route of administration, the active ingredients which comprise said probiotic organisms may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface. Dispersions can also be prepared, for example, in glycerol, liquid polyethylene glycols, and mixtures thereof, and in oils. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food, drink or a diet, e.g. a diet described herein. For oral therapeutic administration, the probiotic organisms may be incorporated with excipients and used in the form of ingestible tablets, buccal tablets, troches, capsules, elixirs, suspensions, syrups, wafers, and the like. The probiotic organism is compounded for convenient and effective administration in effective amounts with a suitable pharmaceutically or food acceptable carrier in dosage unit form as disclosed herein.

In accordance with the present invention, it is also envisaged, that other organisms express the "RS1 peptide(s) fragments"/"RS1 fragments" described herein and that these organisms or parts thereof are employed as or for the preparation of food, feed, "functional food", "food supplements" as well as "food additives" and/or as or for the preparation of pharmaceutical compositions. E. g., organisms to express the "RS1 peptide(s) fragments"/"RS1 fragments" described herein are plants, animals, algae or fungi.

For example, it is envisaged that said food, feed and/or food supplement as employed according to the present invention is carbohydrate-rich and/or fat-rich and/or has a high glycemic index. Yet, it is also envisaged that the food, feed and/or food supplement as employed according to the present invention is carbohydrate-low and/or fat-low and/or has a low glycemic index, as discussed above.

In one embodiment of the present Invention, the herein defined RS1 fragments, food, feed and/or food supplements comprising said fragments, e.g. the dietetics, "novel food", "functional food" and dietary supplements, are employed during/as (special) diets, e.g. diets for patients in need of an amelioration, prevention and/or treatment of obesity. The diets include, for example, carbohydrate-low diets, like sugar-low diets and/or starch-low diets, and/or fat-low diets and/or diets with a low glycemic index.

For instance, it is envisaged that herein defined RS1 fragments, food, feed and/or food supplements comprising said fragments are employed in, to support and/or accompany (special) diets. E. g., the herein defined RS1 fragments, food, feed and/or food supplements comprising said fragments are employed in a diet-supporting and/or diet-accompanying therapy/diet. Said therapy/diet may be, for example, a therapy/diet supporting and/or accompanying specific diets of patients in need of said specific diets. Said patients include, for example patients suffering from obesity, hypercholesterolemia, diabetes (like diabetes 2), hyperglycaemia, diarrhoea, a bile disorder, a renal disorder and/or a disorder related to the deposition of urate crystals in joints, soft tissue and/or the urinary tract.

For instance, it is envisaged that the herein defined RS1 fragments, food, feed and/or food supplements comprising said fragments are employed during carbohydrate-low diets and/or diets having a low glycemic index of diabetes 2 patients as a therapy/diet accompanying said carbohydrate-low diets and/or diets having a low glycemic index for the amelioration, prevention and/or treatment of obesity (Brand-Miller (2002) Am J Nutrition 76(suppl):281S-285S; Parillo and Riccardi (2004) British Journal of Nutrition 92:7-19; Björck and Elmståhl (2003) Proceedings of Nutrition Society 62, 201-206).

In accordance with the present invention it is envisaged that the sugars to be lowered or increased in the diets and food, feed and/or food supplement to be employed within the present invention are, e.g., glucose, galactose saccharose, lactose and/or maltose.

The compositions (e.g. the content of monosaccharides, disaccharides, digestable polysaccharides, protein and fat) of carbohydrate-rich or -low, sugar-rich or -low, starch-rich or -low and fat-rich or -low diets and food, feed and/or food supplements, as well as diets and food, feed and/or food supplements having a high or low glycemic index, are well known in the art. E. g., such compositions are described in Björck and Elmståhl (2003) Proceedings of Nutrition Society 62, 201-206 and Kennedy (2001) J. Am. Diet. Assoc. 101(4): 411-420. An example of a carbohydrate-low diet/diet with low glycemic index is also shown in the experimental part.

"Carbohydrate-low", for example, means that less than 30% energy within the diet and food, feed and/or food supplement are due to carbohydrates. "Fat-low", for example, means that less than 15% of energy within the diet and food, feed and/or food supplement is due to fat. "Sugar-low", for example, means that the diet and food, feed and/or food supplement contains less than 2% by weight monosaccharides plus disaccharides. With respect to the present invention, a low glycemic index, for example, is a glycemic index of less than 70.

The glycemic index is a ranking of carbohydrates based on their immediate effect on blood glucose (blood sugar) levels. It compares foods gram for gram of carbohydrate. Carbohydrates that breakdown quickly during digestion have the highest glycemic indexes. The blood glucose response is fast and high. Carbohydrates that break down slowly, releasing glucose gradually into the blood stream, have low glycemic indexes.

The glycemic index (GI) is a ranking of carbohydrates on a scale from 0 to 100 according to the extent to which they raise blood sugar levels after eating. Foods with a high GI are those which are rapidly digested and absorbed and result in marked fluctuations in blood sugar levels. Low-GI foods, by virtue of their slow digestion and absorption, produce gradual rises in blood sugar and insulin levels, and have proven benefits for health. Low GI diets have been shown to improve both glucose and lipid levels in people with diabetes (type 1 and type 2). They have benefits for weight control because they help control appetite and delay hunger. Low GI diets also reduce insulin levels and insulin resistance.

Recent studies from Harvard School of Public Health indicate that the risks of diseases such as type 2 diabetes and coronary heart disease are strongly related to the GI of the overall diet. In 1999, the World Health Organisation (WHO) and Food and Agriculture Organisation (FAO) recommended that people in industrialised countries base their diets on low-GI foods in order to prevent the most common diseases of affluence, such as coronary heart disease, diabetes and obesity.

To determine a food's GI rating, measured portions of the food containing 10-50 grams of carbohydrate are fed to for example 10 healthy people after an overnight fast. Finger-prick blood samples are taken at 15-30 minute intervals over the next two hours. These blood samples are used to construct a blood sugar response curve for the two hour period. The area under the curve (AUC) is calculated to reflect the total rise in blood glucose levels after eating the test food. The GI rating (%) is calculated by dividing the AUC for the test food by the AUC for the reference food (same amount of glucose) and multiplying by 100. The use of a standard food is essential for reducing the confounding influence of differences in the physical characteristics of the subjects. The average of the GI ratings from all ten subjects is published as the GI of that food.

Accordingly, the glycemic index can be easily determined by the person skilled in the art for any given food, feed and/or food supplements and the like. Also available are lists and tables with the values of glycemic indices, for example in Brand-Miller, "The new glucose revolution" or in Brand-Miller, "The Glucose Revolution Top 100 Low Glycemic Foods", both published in 2003, Marlow and Company, New York, US.

"Carbohydrate-rich", for example, means that more than 55% of the energy within the diet and food, feed and/or food supplement is due to carbohydrates. "Fat-rich" means, for example, that more than 35% of the energy within the diet and food, feed and/or food supplement is due to fat. "Sugar-rich", for example, means that the diet and the food, feed and/or food supplement contains more than 5% by weight monosaccharides plus disaccharides. With respect to the present invention, a high glycemic index, for example, is a glycemic index of more than 90.

In accordance with the present invention, "sugar", for example, means all nutrition-relevant sugars and sugar derivatives. These sugars and sugar derivatives are well known in the art. As mentioned before, it is exemplarily envisaged that glucose, galactose, saccharose, lactose and/or maltose are to be employed in accordance with the present invention. Fructose and/or mannose may also be employed.

In the uses, means, methods provided herein, as well as in the preparation of the food, feed, "functional food", "food supplements" as well as "food additives" of the present invention, the RS1 fragment as defined herein (Q-C-P or derivatives thereof, e.g. QSP, QPP, QTP) is preferably a fragment derived from a polypeptide selected from the group consisting of:

(a) a polypeptide encoded by a nucleic acid molecule as shown in SEQ ID NO: 1, 3, 5, 7;
(b) a polypeptide encoded by a nucleic acid molecule being at least 55% homologous to a nucleic acid molecule as shown in SEQ ID NO: 1, 3, 5, 7 and encoding at least the amino acid stretch Q-C-P, Q-S-P, Q-P-P or Q-T-P; and
(c) a polypeptide as shown in any one of SEQ ID NO: 2, 4, 6, 8.

Most preferably, said peptide is an RS1 fragment, preferably comprising the Q-C-P motive, is derived from a polypeptide selected from the group consisting of the human RS1 (hRS1), Acc. No. NM_006511 or X8287; the porcine RS1, Acc. No. NM_213793 or X64315; the mouse RS1, Acc. No. Y11917 and the rabbit RS1, Acc. No. X82876. Within the human RS1 said QCP motive is from amino acid position 410 to 412, the SDSDRIEP (SEQ ID NO: 9) motive as mentioned herein is from amino acid position 43 to 50, the QSP motive as mentioned herein is apparent in the hRS1 two times, namely from amino acid positions 19-21 and 91-93, and the QPP motive as mentioned herein is from amino acid position 311-313 (e. g., see, SEQ ID No. 2). The inventive "Q-C-P peptide" to be employed in accordance with this invention comprises the Q-C-P motive and additional (e.g. neighbouring) amino acid residues as comprised in the herein defined natural RS1 polypeptides. As pointed out above, the maximal length of an "Q-C—P peptide" as defined herein is about 150, preferably of at most 120 amino acids. Most preferred are, however, short peptides, comprising 13, 12, 11, 10, 9, 8, 6 and most preferably 3 amino acid residues. As already mentioned before, it is also envisaged, that the RS1 fragments as defined herein may be attached to further amino acids, heterologous peptides and/or heterologous proteins. Said further amino acids, heterologous peptides and/or heterologous proteins may comprise, derived from and/or consisting of domains having additional functionalities, like, e. g. further pharmacological effects or specific tags for facilitating purification. Accordingly the RS1 fragments as defined herein may also be part of fusion polypeptides or fusion proteins. In accordance with the present invention, said fusion polypeptides or fusion proteins comprising the RS1 fragments as defined herein may also comprise more than 150 amino acids.

Accordingly, particular preferred RS1 minimal fragments to be employed in accordance with this invention are Q-N-E-Q-C-P-Q-V-S-F (SEQ ID NO: 16k, preferably Q-N-E-Q-C-P-Q-V-SS(EQ ID NO: 17), more preferably Q-N-E-Q-C-P (SEQ ID NO: 18) or Q-C-P-Q-V-S (SEQ ID NO: 19) and most preferably Q-C-P. However, also envisaged to be employed in context of the present invention are the RS1 fragments Q-S-P, S-S-G-Q-S-P (SEQ ID NO: 20), Q-S-P-D-V-GS(EQ ID NO: 21), S-S-G-Q-S-P-D-V-G (SEQ ID NO: 22), P-T-D-Q-S-P (SEQ ID NO: 23), Q-S-P-A-M-P (SEQ ID NO: 24), P-T-D-Q-S-P-A-M-P (SEQ ID NO: 25), Q-P-P, Q-D-L-Q-P-P (SEQ ID NO: 26), Q-P-P-E-T-N (SEQ ID NO: 27), Q-D-L-Q-P-P-E-T-N (SEQ ID NO: 28) and/or Q-T-P.

The nucleic acid molecule encoding the herein defined "Q-C-P peptide"/"RS1 fragments" may be any type of nucleic acid, e.g. DNA, RNA or PNA (peptide nucleic acid).

For the purposes of the present invention, a peptide nucleic acid (PNA) is a polyamide type of DNA analog and the monomeric units for adenine, guanine, thymine and cytosine are available commercially (Perceptive Biosystems).

The DNA may, for example, be cDNA. In a preferred embodiment it is a fragment of genomic DNA encoding the herein defined RS1 fragment. The RNA may be, e.g., mRNA. The nucleic acid molecule may be natural, synthetic or semi-synthetic or it may be a derivative, such as peptide nucleic acid (Nielsen (1991), Science 254, 1497-1500) or phospho-rothioates. Furthermore, the nucleic acid molecule may be a recombinantly produced chimeric nucleic acid molecule comprising any of the aforementioned nucleic acid molecules either alone or in combination.

Preferably, the nucleic acid molecule(s) encoding the "RS1 fragment" as defined herein is part of a vector. Therefore, the present invention relates in another embodiment of the use, method and means to a vector comprising the nucleic acid molecule encoding the "RS1 fragment" as defined herein. Such a vector may be, e.g., a plasmid, cosmid, virus, bacteriophage or another vector used, e.g. conventionally in genetic engineering, and may comprise further genes such as marker genes which allow for the selection of said vector in a suitable host cell and under suitable conditions.

The nucleic acid molecules encoding the "RS1 fragment" as defined herein may be inserted into several commercially available vectors. Nonlimiting examples include plasmid vectors compatible with mammalian cells, such as pUC, pBluescript (Stratagene), pET (Novagen), pREP (Invitrogen), pCRTopo (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMT-neo, pRSVgpt, pRSVneo, pSV2-dhfr, pUCTag, pIZD35, pLXIN and pSIR (Clontech) and pIRES-EGFP (Clontech). Baculovirus vectors such as pBlueBac, BacPacz Baculovirus Expression System (CLONTECH), and MaxBac™ Baculovirus Expression System, insect cells and protocols (invitrogen) are available commercially and may also be used to produce high yields of biologically active protein. (see also, Miller (1993), Curr. Op. Genet. Dev. 3, 9; O'Reilly, Baculovirus Expression Vectors: A Laboratory Manual, p. 127). In addition, prokaryotic vectors such as pcDNA2; and yeast vectors such as pYes2 are nonlimiting examples of other vectors suitable for use with the present invention. For vector modification techniques, see Sambrook and Russel (2001), loc. cit. Vectors can contain one or more replication and inheritance systems for cloning or expression, one or more markers for selection in the host, e.g., antibiotic resistance, and one or more expression cassettes.

The coding sequences inserted in the vector can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods.

Furthermore, the vectors may, in addition to the nucleic acid sequences encoding for the "RS1 fragment" defined herein, comprise expression control elements, allowing proper expression of the coding regions in suitable hosts. Such control elements are known to the artisan and may include a promoter, translation initiation codon, translation and insertion site or internal ribosomal entry sites (IRES) (Owens (2001), Proc. Natl. Acad. Sci. USA 98, 1471-1476) for introducing an insert into the vector. Preferably, the nucleic acid molecule encoding for the "Q-C-P peptide" defined herein is operatively linked to said expression control sequences allowing expression in eukaryotic or prokaryotic cells.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcome virus), human elongation factor 1$\alpha$-promoter, CMV enhancer, CaM-kinase promoter or SV40-enhancer.

For the expression in prokaryotic cells, a multitude of promoters including, for example, the tac-lac-promoter, the lacUV5 or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11. An expression vector according to this invention is at least capable of directing the replication, and preferably the expression, of the nucleic acids and protein of this invention. Suitable origins of replication include, for example, the Col E1, the SV40 viral and the M 13 origins of replication. Suitable promoters include, for example, the cytomegalovirus (CMV) promoter, the lacZ promoter, the gal10 promoter and the Autographa *californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Specifically-designed vectors allow the shuttling of DNA between different host cells, such as bacteria-yeast, or bacteria-animal cells, or bacteria-fungal cells, or bacteria or invertebrate cells. The expression of the herein defined "Q-C-P peptide" in prokaryotic cells may be particularly useful in the preparation of pharmaceutical compositions or food additives defined herein. It is, e.g. envisaged that bacterial hosts are employed which are capable of expressing a "Q-C-P peptide" as defined herein. It is also envisaged that these bacteria are administered and/or given to humans in form of pharmaceutical compositions and/or food-additives; e.g. as "probiotic food-additives".

Beside the nucleic acid molecules encoding the "Q-C-P peptide"/"RS1 fragment" as defined herein, the vector may further comprise nucleic acid sequences encoding secretion signals. Such sequences are well known to the person skilled in the art. Furthermore, depending on the expression system used leader sequences capable of directing the expressed polypeptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof, into, inter alia, the extracellular membrane. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

The invention also provides for a method of preparation of a pharmaceutical composition for the amelioration, prevention and/or treatment of a metabolic disease or a secondary disorder caused by a pathological modification of homeostasis, comprising the step of admixing an RS1 fragment/"Q-C-P peptide" as described herein, a nucleic acid molecule encoding the same and/or a vector comprising said nucleic acid molecule with a pharmaceutically acceptable carrier. Corresponding carrier are illustratively mentioned above.

The metabolic disease or secondary disorder to be treated and/or ameliorated or even prevented within this embodiment is preferably obesity, hypercholesterolemia, diabetes, hyperglycaemia, diarrhoea, a bile disorder, a renal disorder and/or a disorder related to the deposition of sodium urate crystals in joints, soft tissue and/or the urinary tract.

The definitions of metabolic diseases or secondary disorders, as given in the corresponding embodiments herein above, apply here, mutatis mutandis.

Also provided in context of this invention is a method of screening for a receptor, transporter and/or channel that (specifically) interacts with an RS1 fragment as defined herein, comprising the steps of:
(a) introducing said RS1 fragment into a system allowing for a candidate receptor, transporter and/or channel to be active, under conditions which allow said RS1 fragment to be active/interact with said candidate receptor, transporter and/or channel, and
(b) evaluating changes in activity of said candidate receptor, transporter and/or channel in said system.

As illustrated in the appended examples, the RS1 fragment as defined herein may be introduced into a system in which the candidate receptor, transporter and/or channel is expressed or overexpressed. Also envisaged is the introduction of the RS1 fragment into a system where the expression of endogeneous RS1 protein is suppressed. It is furthermore envisaged that the RS1 fragment ("Q-C-P peptide" or derivatives thereof as described herein) is introduced into a system in which the candidate receptor, transporter and/or channel is overexpressed together with a transporter that mediates uptake of said RS1 fragment. As illustrated in the appended examples, said candidate receptor, transporter and/or channel may be a peptide transporter (e.g. PEPT1 or PEPT2). Accordingly, in a preferred embodiment of said method of screening for a receptor, transporter and/or channel, said system allows additionally for a peptide transporter (preferably PEPT1 or PEPT2), to be active within said system.

Also envisaged, in accordance with this invention, is a method of screening for a target and/or an interacting partner of an RS1 fragment as defined in the present invention, comprising the steps of:
(a) contacting said RS1 fragment with a candidate target and/or a candidate interacting partner under conditions allowing for interaction of said candidate target and/or said candidate interacting partner with said RS1 fragment; and
(b) evaluating the degree of affinity between said candidate target and/or said candidate interacting partner and said RS1 fragment.

Also provided is a method of screening for RS1 fragments (or derivatives thereof) that can act as substrates for proton-peptide cotransporters, preferably human PEPT1 and/or human PEPT2, comprising the steps of:
(a) contacting candidate RS1 fragments (or derivatives thereof) with a system allowing for said proton-peptide cotransporters to be active; and
(b) evaluating the uptake of said candidate RS1 fragments or derivatives into said system.

The RS1 fragments (or derivatives thereof) to be tested in this embodiment may also be able to inhibit the expressed activity of all the receptors, transporters and/or channels mentioned herein above, preferably of SGLT1.

As an example, the system to be employed in the above recited screening system may be a human cell line, e.g. a cell line derived of kidney or gut, which expresses one or more of said proton-peptide cotransporters, optionally together with one or more of the above discussed receptors, transporters and/or channels. In such a system, the affinity of the candidate RS1 fragments or derivatives to be screened to the proton-peptide cotransporters can be evaluated, optionally together with the impact, said candidate RS1 fragments or derivatives may have on the coexpressed receptors, transporters and/or channels.

In a preferred embodiment or the screening method provided herein, human cell lines from kidney or gut are used as screening systems. Said cell lines may coexpress the human PEPT1 and PEPT2 together with the human SGLT1. In these systems, the uptake and impact of candidate RS1 fragments or derivatives, added outside to the system, may evaluated by measuring the sodium-dependent transport of glucose via an uptake of radioactively labelled α-methyl-D-glucoside (AMG).

Said SGLT1 may be a SGLT1 variant that can be easily localised in the plasma membrane and can be detected by a cell-sorting apparatus. For example, such SGLT1 variant may be a SGLT1 protein coupled with a fluorescent dye.

As shown in the appended examples, also other cells are, however, useful in the screening methods provided herein. These cells comprise, but are not limited to, oocytes (in particularly *Xenopus* oocytes). Preferably, said oocytes are capable of heterologously expressing proteins, in particularly receptors, transporters and/or channels as defined herein. Corresponding embodiments can easily be deduced from the following experimental part The herein provided screening methods are in particular useful to deduce and/or characterize specific receptors, transporters and/or channels for the RS1 minimal peptides described herein. Accordingly, specific interaction and/or functional partners may be deduced, validated and/or characterized. It is, e.g. envisaged to express a potential candidate "interaction partner" in a homologous or heterologous system (like in the oocyte system described and used in the experimental part, or in human test cells, like cells derived from gut or kidneys) and to contact said interaction partner with a "Q-C-P- peptide" as described herein. Activity of the potential interaction partner may be measured and evaluated by methods provided in the appended examples, e.g. the transport rate of the peptide itself or e.g. glucose or amino acid residue uptake can be measured. It is also envisaged that the expression rate of the potential candidate molecule be assessed. Again, experimental and exemplifying details are given herein below.

Furthermore, conditions which allow said RS1 fragment to be active/interact with said candidate receptor, transporter and/or channel, conditions allowing for interaction of said candidate target and/or said candidate interacting partner with said RS1 fragment as well as systems allowing for said proton-peptide cotransporters to be active are exemplified in the appended examples and are well known in the art.

The present invention is further described by reference to the following non-limiting figures and examples.

The Figures show:

FIG. 1 Brefeldin A induces disappearance of RS1 from the TGN in LLC-PK$_1$ cells.

Subconfluent LLC-PK1 cells grown on cover slips. Cells were incubated for 1 min (b, e) or for 5 min (c, f) with 2 μg/ml Brefeldin A (BRE). Cell metabolism was stopped by transfer of the cells on ice and superfusion with cold washing buffer. After paraformaldehyde fixation and permeabilization, control cells (a, d) or cells incubated with Brefeldin A (b,c,e,f) were immunostained with an affinity purified antibody against SGLT1 (a-c) or with an affinity purified antibody against RS1 (d-f). Immunstaining was visualized using secondary antibody directed against rabbit IgG that was coupled to AlexaFluor 555. Bar 1 μm.

Figure 2:
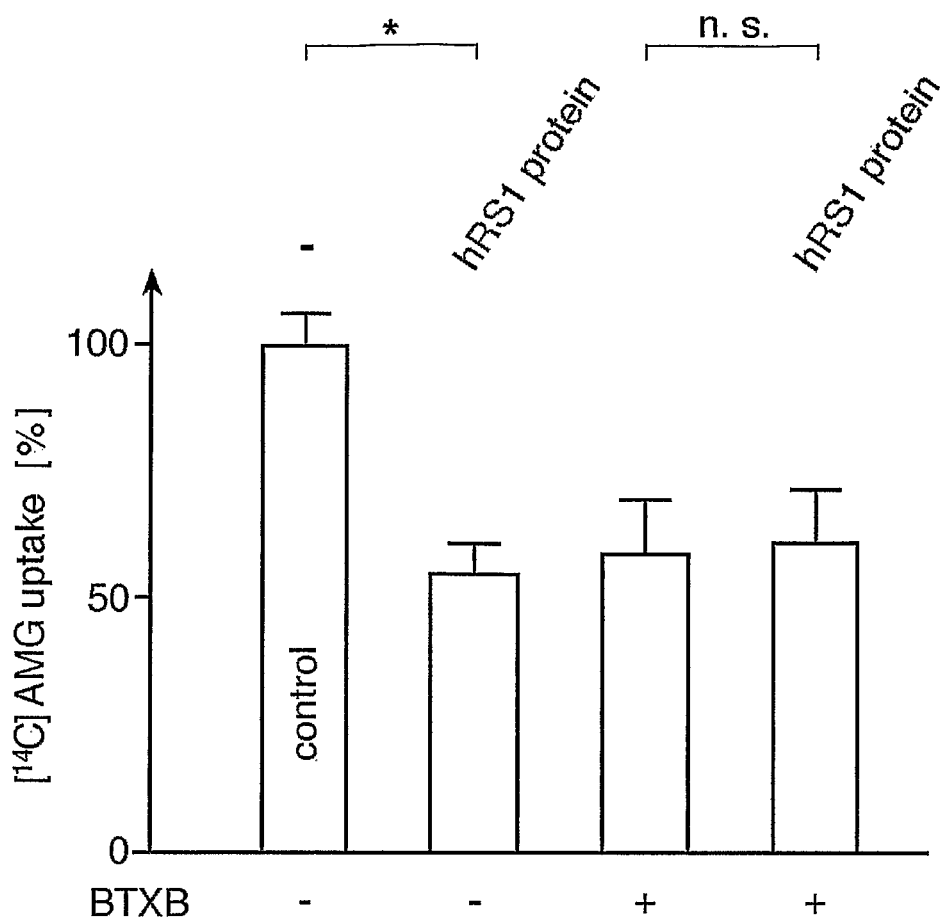

FIG. 2 Inhibition of hSGLT1 expressed [$^{14}$C]AMG uptake by injection of purified hRS1 protein in the absence and presence of botulinustoxin B.

Oocytes were injected with 2.5 ng SGLT1-cRNA and incubated for 3 days. 50 nl of KOri buffer, KOri buffer plus 5 ng of purified hRS1, KOri buffer containing 1.7 ng botulinum toxin B (BTXB), or KOri buffer plus 5 ng of purified hRS1 and 1.7 ng BTXB were injected. After 30 min incubation at room temperature, uptake of 50 μM [$^{14}$C]AMG was measured. Mean values of 7-10 oocytes±standard deviations of the mean are shown. *P<0.05 for effect of hRS1 protein on AMG uptake. One typical experiment out of 3 independent experiments is shown.

Figure 3:
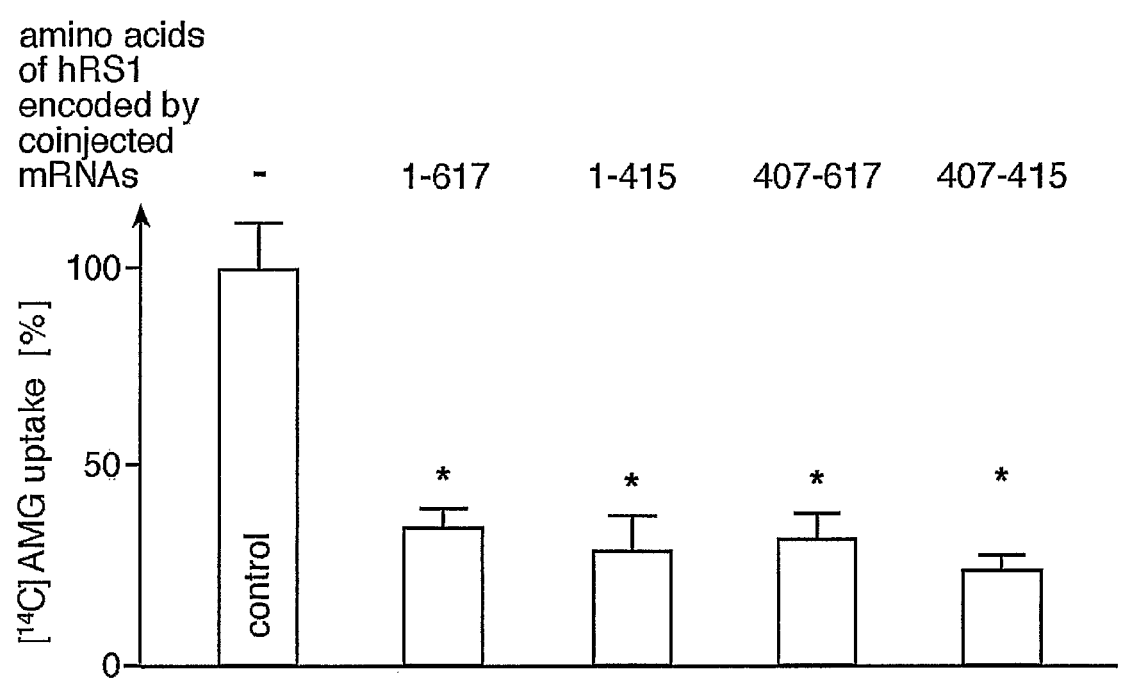

FIG. 3 Identification of a domain in the middle part of hRS1 that inhibits glucose uptake expressed by hSGLT1.

Oocytes were injected with 2.5 ng SGLT1-cRNA alone (amino acids 1 to 617, control), with 2.5 ng SGLT1-cRNA plus 7.5 ng hRS1-cRNA, or with 2.5 ng SGLT1-cRNA plus 7.5 ng cRNAs encoding the indicated fragments of hRS1 (numbering see Lambotte (1996), DNA Cell Biol., 15, 769-777.). After three days incubation of oocytes, uptake of 50 μM [$^{14}$C]AMG was measured. [$^{14}$C]AMG uptake in non-injected oocytes was always less than 5% compared to the uptake observed after injection of SGLT1-cRNA. In the presence of 100 μM phlorizin, an inhibitor of SGLT transporters, [$^{14}$C]AMG uptake in hSGLT1 expressing oocytes was inhibited by at least 90%. A representative experiments out of four experiments is shown. Mean of 7-10 oocytes and standard deviations of the means are shown. *P<0.05 for difference to control.

Figure 4:
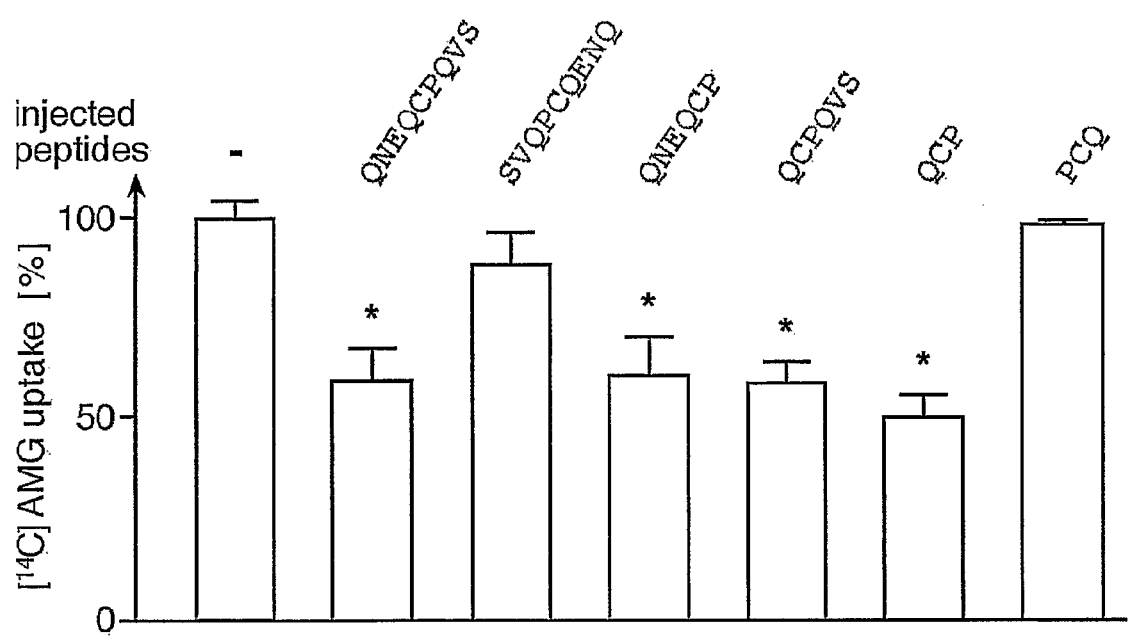

FIG. 4 Inhibition of hSGLT1 expressed glucose transport activity in oocytes by injection of tripeptide QCP derived from hRS1.

Oocytes were injected with 2.5ng SGLT1-cRNA, incubated for 3days, and the uptake of 50μM [$^{14}$C]AMG was measured (control). In some experiments 50nl KOri buffer per oocyte containing 1.5mM of the indicated peptides were injected 30min before the uptake measurements were started. A representative experiment out of four experiments is shown. Mean of 7-10oocytes and standard deviations of the means are shown. *P<0.05for difference to control. FIG. 4 discloses SEQ ID NOS 17, 29, 18and 19, respectively, in order of appearance.

Figure 5:
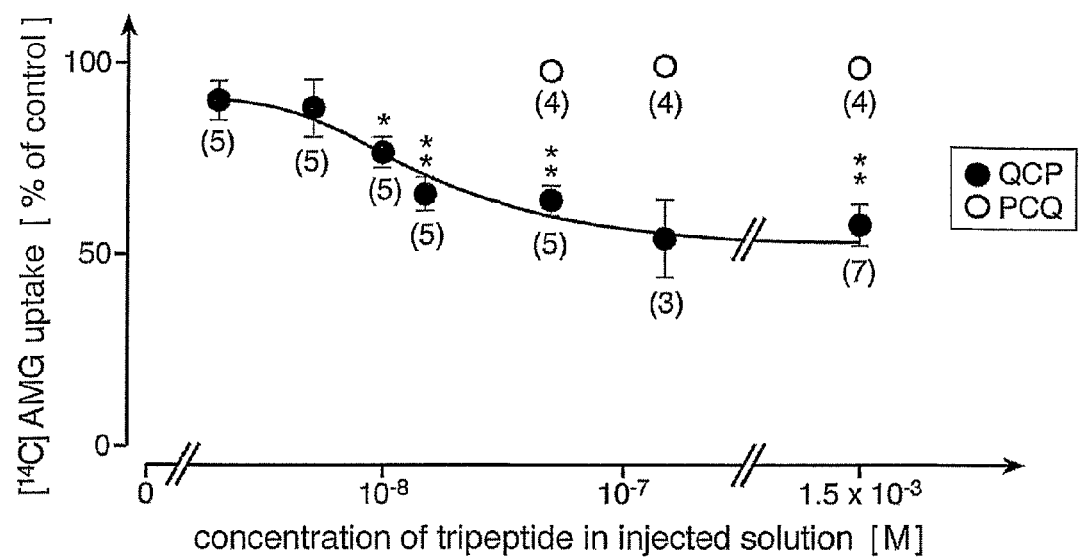

FIG. 5 High affinity inhibition of hSGLT1 expressed glucose transport by QCP.

Oocytes were injected with 2.5 ng SGLT1-cRNA, incubated for 3 days and 50 nl of KOri buffer (control) or 50 nl of KOri buffer containing the indicated peptide concentrations were injected. After 30 min uptake of 50 μM [$^{14}$C]AMG was measured. For each concentration of injected peptide 3-7 individual experiments with 7-10 non-injected control oocytes and 7-10 peptide-injected oocytes were performed. [$^{14}$C]AMG uptake is presented as percentage of uptake observed in control oocytes that were injected with buffer. Mean and standard deviations of the means of these experiments are presented. The numbers of independent experiments are indicated in brackets. *P<0.05, **P<0.01 for difference between buffer-injected oocytes and oocytes injected with peptide.

Figure 6:
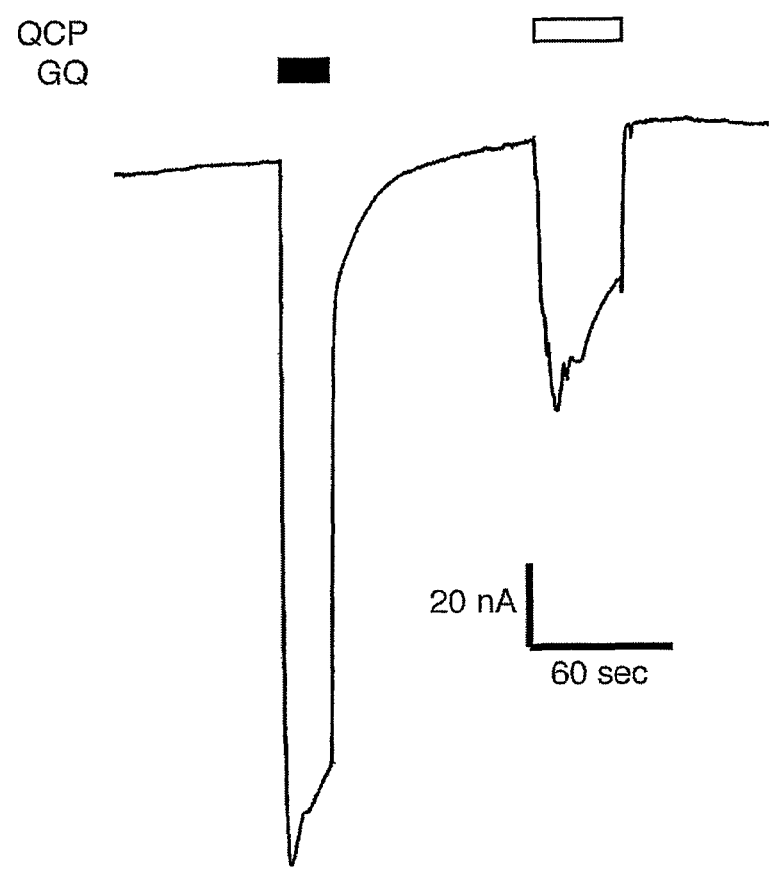

FIG. 6 Demonstration that the small intestinal peptide transporter hPEPT1 translocates QCP.

Oocytes were injected with 30 ng hPEP1-cRNA and incubated for 3 days in Ori buffer. For measurement of electrogenic peptide uptake by two-electrode voltage clamp, oocytes were superfused with acid Ori buffer (pH 6.5), clamped to −40 mV, and superfused with acid Ori buffer, acid Ori buffer containing 5 mM of the control peptide GQ or 5 mM of QCP. With both peptides significant inward currents were induced. A representative experiment out of 5 experiments using 3 different batches of oocytes is shown.

Figure 7:
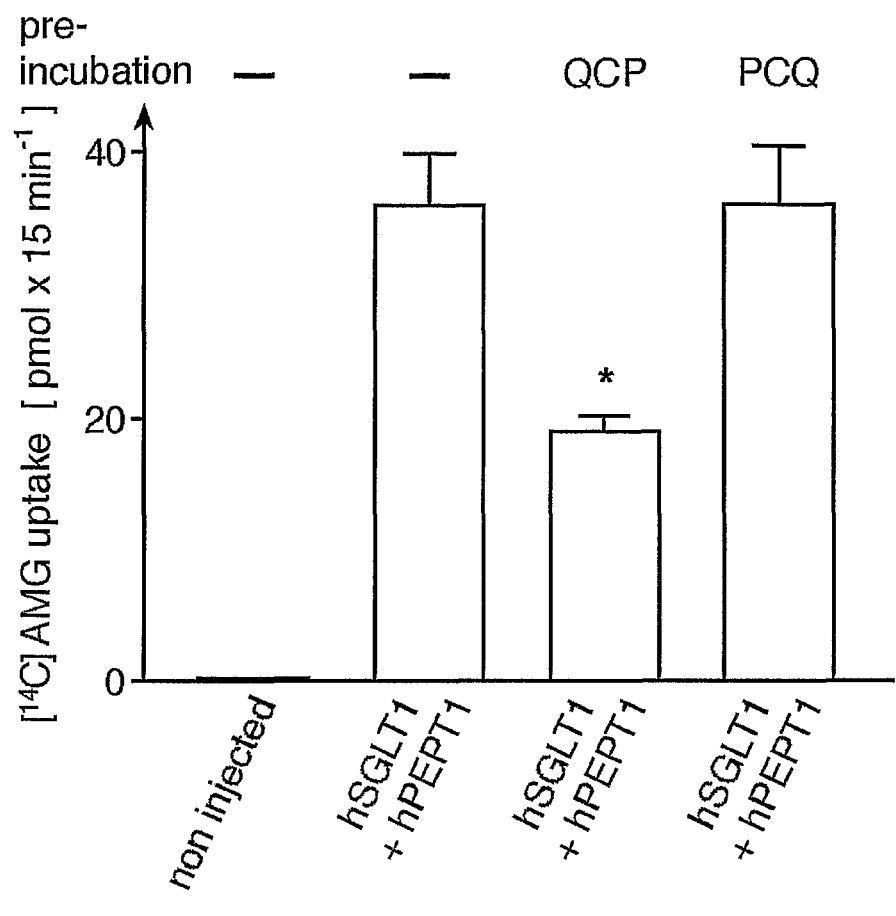

FIG. 7 Inhibition of expressed glucose transport in oocytes expressing hPEPT1 by addition of QCP to the medium.

Non-injected oocytes and oocytes injected with 2.5 ng hSGLT1 cRNA plus 10 ng hPEPT1 cRNA were incubated for 3 days in Ori buffer (pH. 7.5). The oocytes were incubated for 30 min with acid Ori buffer (pH 6.5), with acid Ori buffer containing 3 mM QCP, or with acid Ori buffer containing 5 mM PCQ. After washing with Ori buffer (pH 7.5), uptake of 50 μM [$^{14}$C]AMG was measured. A representative experiment out of 3 is indicated. **P<0.01 for difference to oocytes expressing hSSLT1 plus PEPT1.

Figure 8:
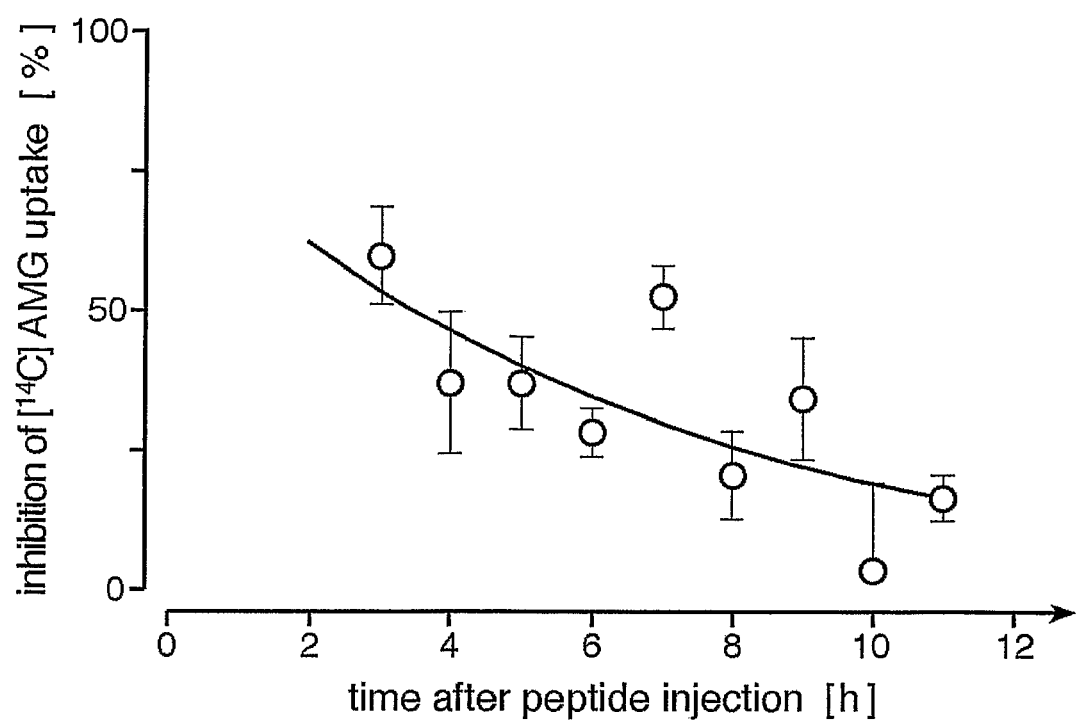

FIG. 8 Time course of inhibition of hSGLT1 expressed AMG uptake in oocytes after injection of 1 mM QCP.

Oocytes were injected with 2.5 ng hSGLT1-cRNA, incubated for 3 days and 50 nl of KOri buffer (control) or 50 nl of KOri buffer containing 3 mM QCP. After the indicated time periods uptake of 50 μM [$^{14}$C]AMG was measured. For each time point [$^{14}$C]AMG uptake was measured in 7-10 oocytes injected with buffer and in 7-10 oocytes injected QCP. For each time point mean values±standard deviations of the means were calculated considering the propagation of error. An exponential decay curve is fitted to the data.

Figure 9:
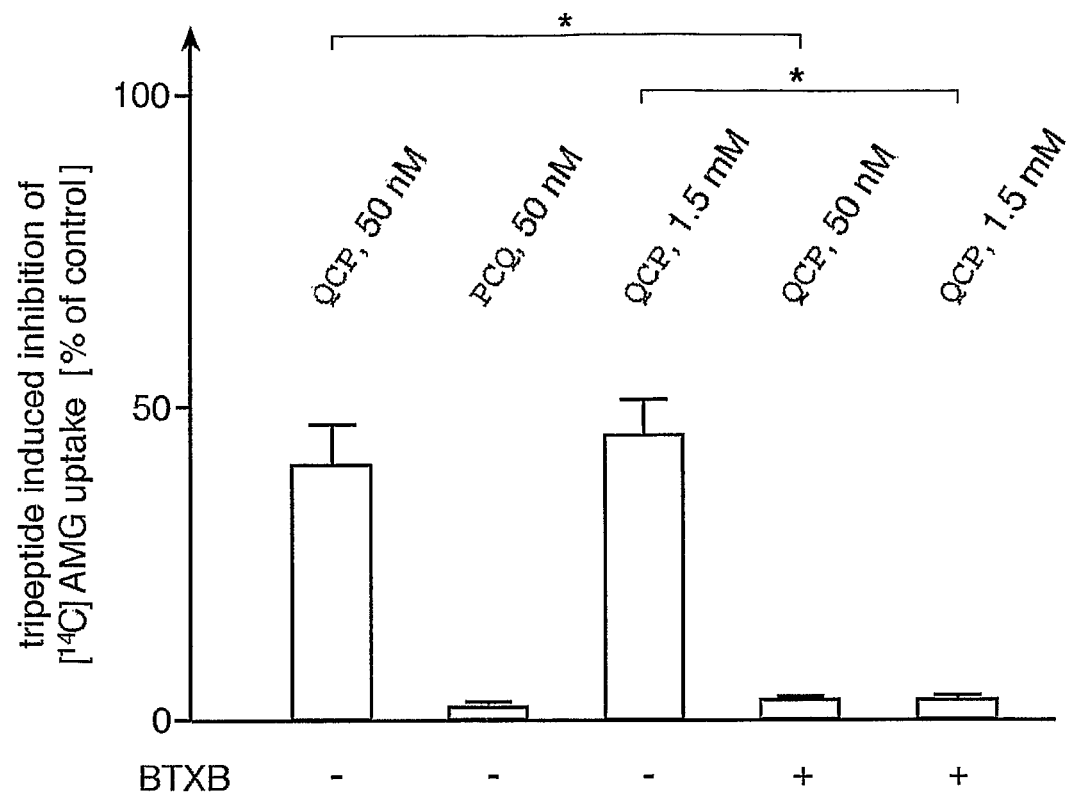

FIG. 9 Inhibition of hSGLT1 expressed [$^{14}$C]AMG uptake by injection of QCP in the absence and presence of botulinum toxin B.

Oocytes were injected with 2.5 ng SGLT1-cRNA and incubated for 3 days. 50 nl of KOri buffer (control for SGLT1 mediated AMG uptake in the absence of botulinum toxin B), 50 nl of KOri buffer containing 1.7 ng BTXB (control for SGLT mediated AMG uptake in the presence of BTXB), 50 nl KOri buffer plus 50 nM or 1.5 mM QCP, 50 nl KOri buffer plus 50 nM PCQ, or 50 nl KOri buffer plus 1.7 ng BTXB and either 50 nM or 1.5 mM QCP. After 30 min incubation at room temperature uptake of 50 μM [$^{14}$C]AMG was measured. The inhibition of AMG uptake by the addition of tripeptides in the absence or in the presence of BTXB is indicated. Mean values±standard deviations of the mean are shown that were derived from 7-10 oocytes without injection of peptides and 7-10 oocytes with injected peptides. *P<0.05 for difference between uptake rates measured in the presence QCP measured in the absence and presence of BTXB.

Figure 10:
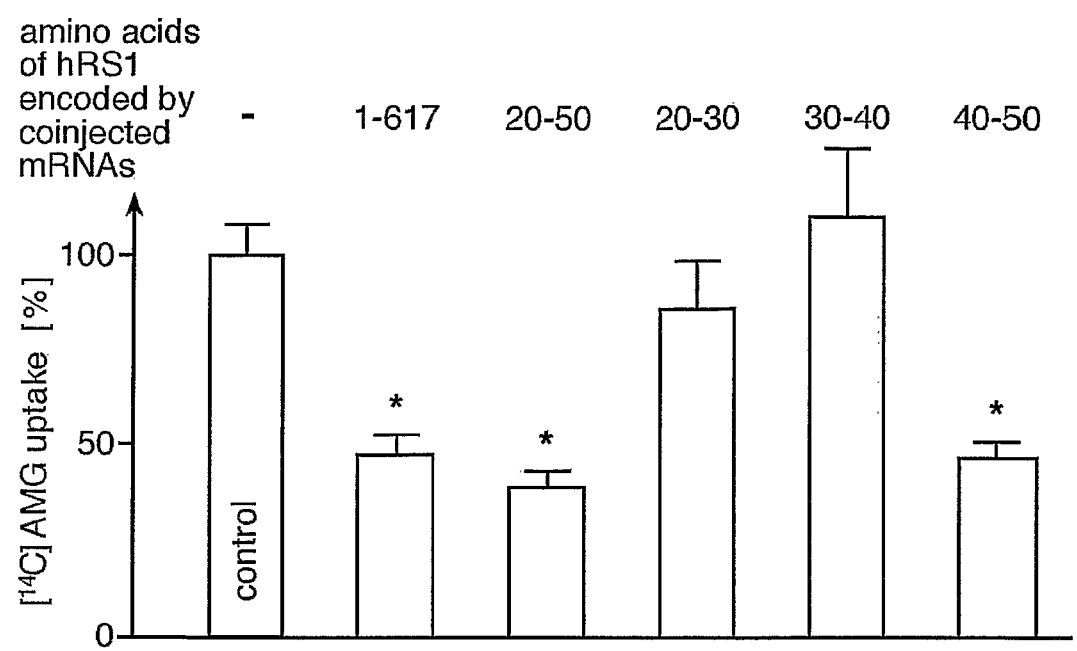

FIG. 10 Identification of a domain in the N-terminal part of hRS1 that inhibits glucose uptake expressed by hSGLT1.

In *Xenopus* oocytes hSGLT1 alone (control), hSGLT1 plus hRS1 (amino acids 1-617) or hSGLT1 plus fragments of hRS1 encoding the indicated amino acids of hRS1 were expressed by injection of the respective cRNAs. The experiment was performed and is presented as in FIG. 3.

Figure 11:
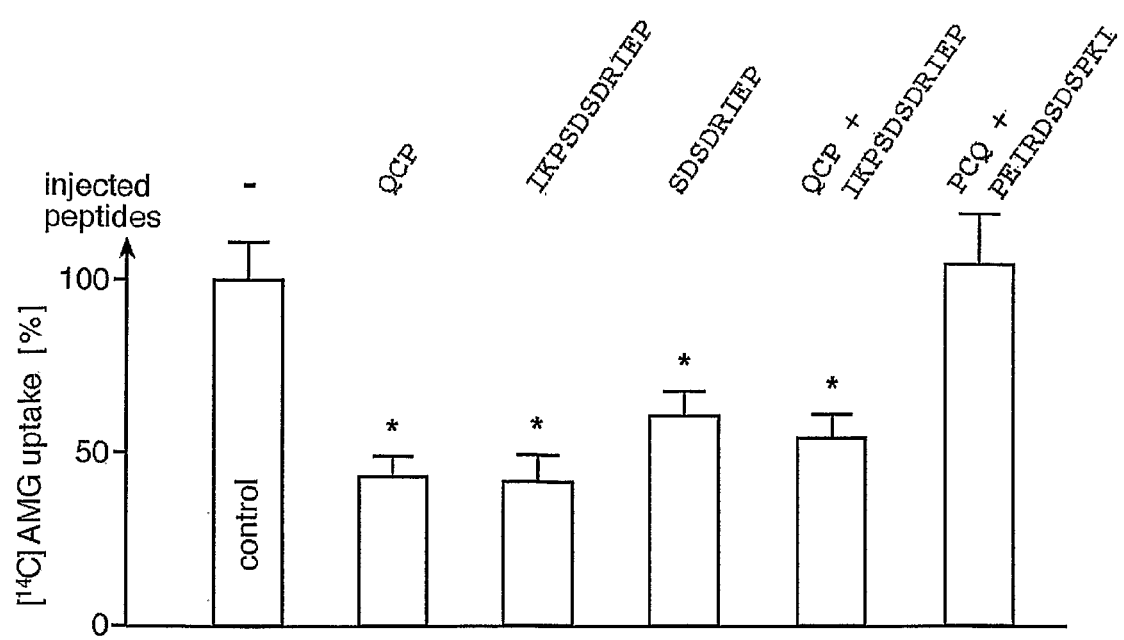

FIG. 11 Inhibition of hSGLT1expressed glucose transport activity by intracellular injection of a unodecapeptide or a octapeptide derived from the N-terminal part hRS1.

Oocytes expressing hSGLT1 were injected with 50nl KOri buffer containing 3 mM of the tripeptide QCP, 3mM the unodecapeptide IKPSDSDRIEP (SEQ ID NO: 10), 3mM of the octapeptide SDSDRIEP (SEQ ID NO: 9), 3mM QCP plus 3mM IKPSDSDRIEP (SEQ ID NO: 10), or 3mM of the reverse tripeptide plus 3mM of the reverse unodecapeptide. Experiment was performed and is presented as in FIG. 4. FIG. 11 also discloses "PEIRDSDSPKI" as SEQ ID NO: 30.

Figure 12:
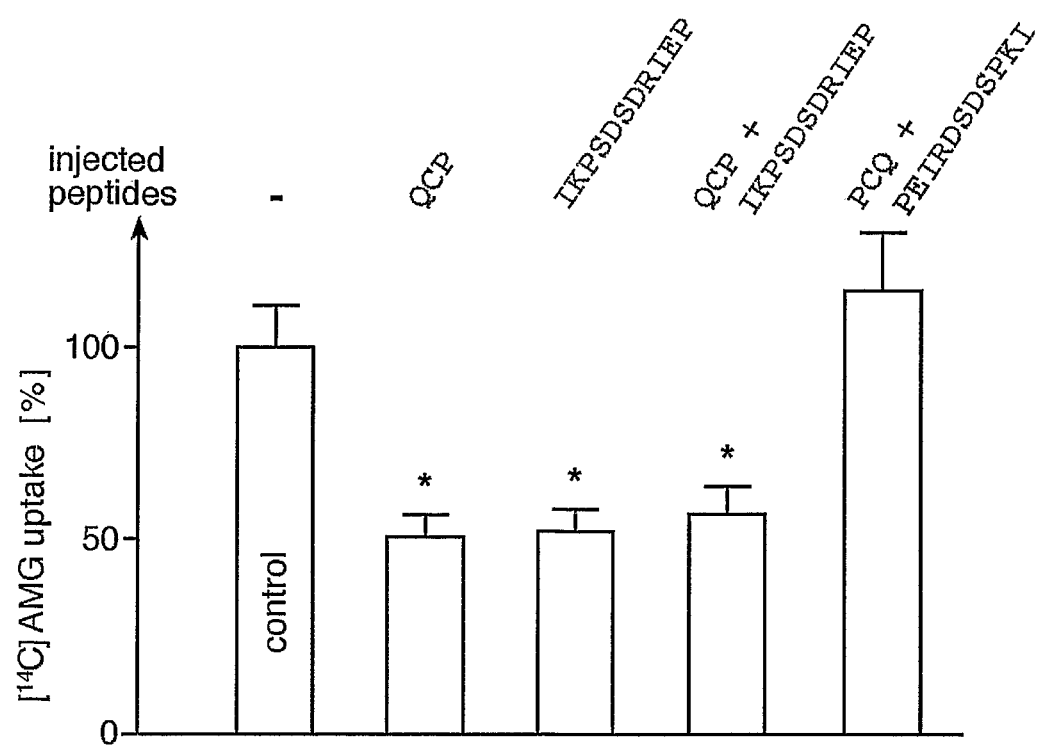

FIG. 12 Inhibition by QCP and IKPSDSDRIEP (SEQ ID NO: 10) of glucose transport expressed by rabbit SGLT1.

Oocytes expressing rbSGLT1 were injected with 50 nl containing 3 mM QCP or 3 mM IKPSDSDRIEP (SEQ ID NO. 10) or 3 mM QCP plus 3 mM IKPSDSDRIEP (SEQ ID NO: 10) or 3 mM of the reverse tripeptide plus 3 mM of the reverse unodecapeptide. The experiment was performed and is presented as in FIG. 4. FIG. 12 also discloses "PEIRDSDSPKI" as SEQ ID NO: 30.

Figure 13:
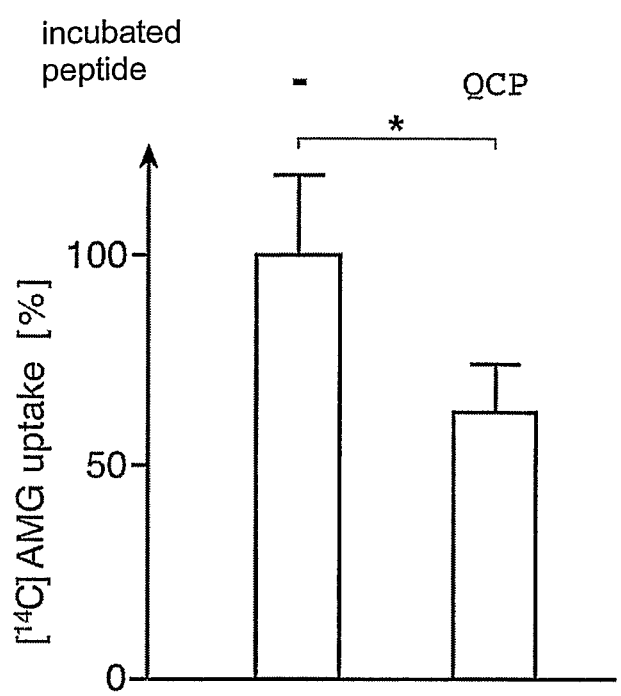

FIG. 13 Inhibition of SGLT1 in human epithelial cells by QCP.

SGLT1 mediated uptake was measured in the absence (−) or presence (QCP) of QCP by subtracting the uptake in the presence of phlorizin from the uptake without phlorizin. Mean values with standard deviation of 5 measurements are indicated. * indicates P<0.05 for difference, calculated by Student's t-test.

Figure 14:
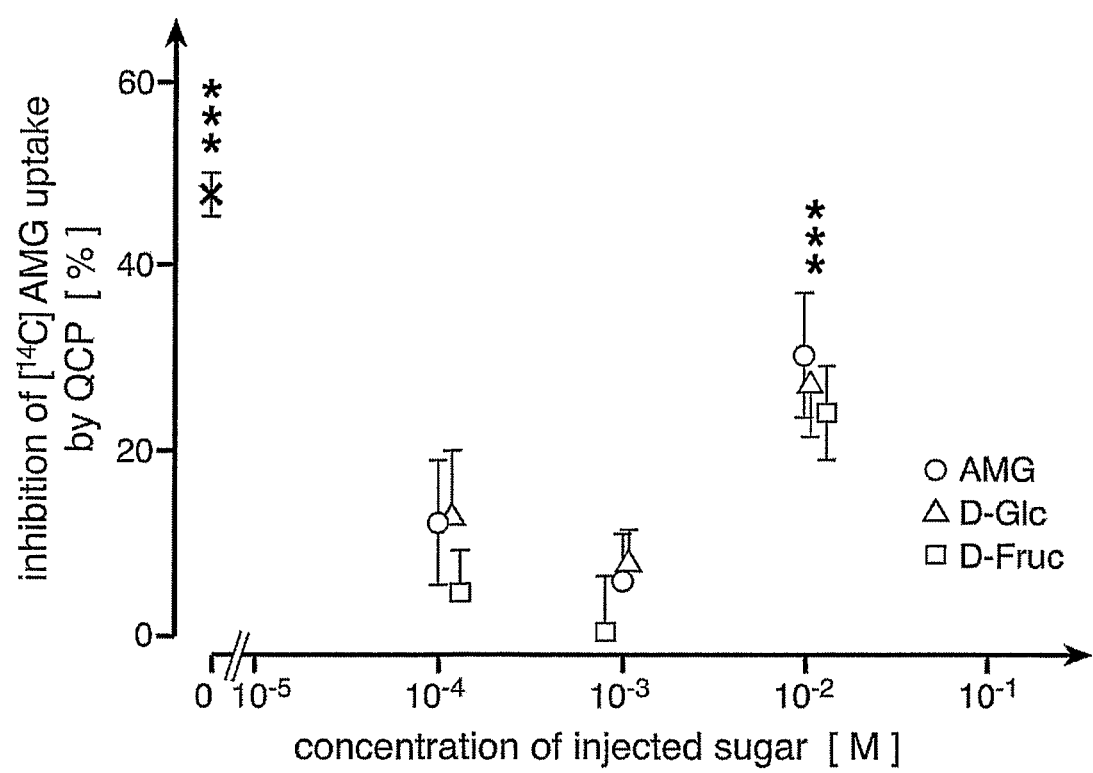

FIG. 14 Glucose dependence of inhibition of SGLT1 mediated AMG uptake by QCP.

Inhibition by QCP in the presence of different concentrations of intracellular monosaccharides was measured. Mean values with standard deviations from 25-30 measurements without QCP and 25-30 measurements with QCP from three different batches of oocytes are indicated. *** indicates P<0.001 for difference between AMG uptake in the presence of the indicated intracellular sugar concentration in the absence and presence of QCP.

Figure 15:
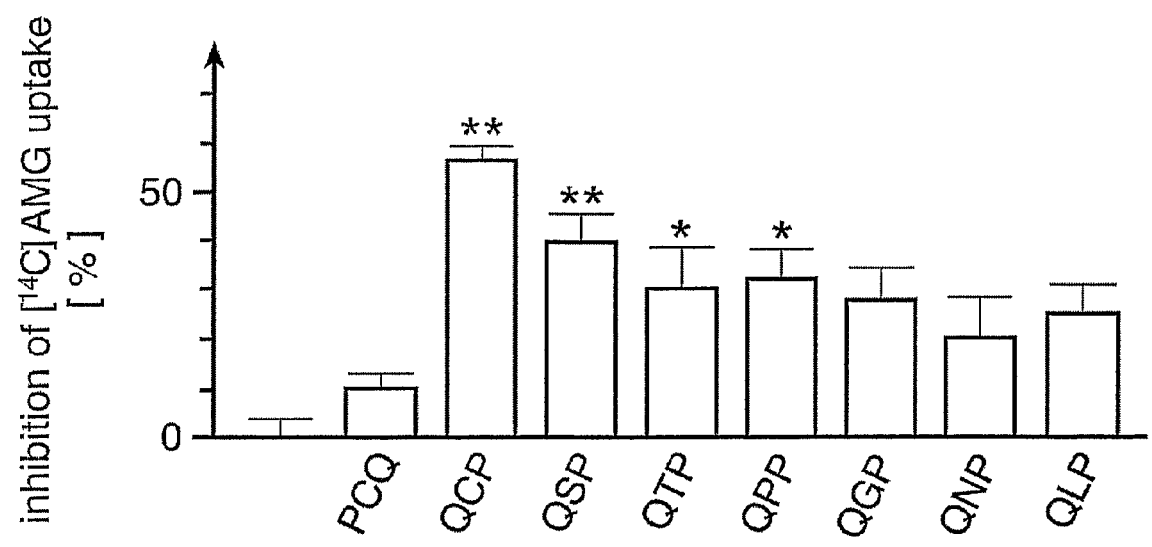

FIG. 15 Inhibition of hSGLT1 expressed glucose transport activity in oocytes by QCP and QCP derived tripeptides.

For each injected peptide 3 individual experiments with 7-10 buffer-injected control oocytes and 7-10 peptide injected oocytes were performed. Means and standard deviations of these experiments are presented. * indicates P<0.05, ** indicates P<0.01 for difference between buffer-injected oocytes and oocytes injected with peptide.

THE EXAMPLES ILLUSTRATE THE INVENTION

Example 1

General Methods (A) Materials

[$^{14}$C] labelled methyl-α-D-glucopyranoside (AMG) containing 5.7 GBq/mmole) and all other materials were obtained as described earlier (Lambotte (1996), DNA Cell Biol., 15, 769-777; Veyhl (2003), J. Membrane Biol., 196, 71-81.).

(B) cDNA Cloning and Preparation of cRNAs cDNAs of hRS1 fragments were cloned using the overlap-extension method as described earlier (Gorboulev (1999), Mol. Pharmacol., 56, 1254-1261; Lambotte (1996), DNA Cell Biol., 15, 769-777). cRNAs of hRS1 and of hRS1 fragments were synthesized in vitro as described (Veyhl (2003), J. Membrane Biol., 196, 71-81).

(C) Expression of Transporters and hRS1 or Fragments of hRS1 in *Xenopus* Oocytes.

Expression to human SGLT1 (hSGLT1), rabbit SGLT1 (rbSGLT1), human PEPT1 (hPEPT1) and co-expression of hSGLT1 or rbSGLT1 with hRS1 or hRS1 fragments were performed as described earlier (Veyhl (2003), J. Membrane Biol., 196, 71-81). cRNA of hPEPT1 (30 ng per oocyte), cRNAs of hSGLT or rbSGLT1 (2.5 ng per oocyte) plus cRNA of hRS1 or of hRS1 fragments (7.5 ng per oocyte) were injected into oocytes. The oocytes were incubated for three days at 16° C. in ORi buffer (in mM: 5 HEPES-Tris, pH 7.4, 100 NaCl, 3 KCl, 2 CaCl$_2$, and 1 MgCl$_2$). Then, the uptake of [$^{14}$C]AMG expressed by hSGLT1 was measured at pH 7.4 as described (Veyhl (2003), J. Membrane Biol., 196, 71-81). Transport by expressed hPEPT1 was measured using the two-electrode voltage clamp technique (Veyhl (2003), J. Membrane Biol., 196, 71-81). The oocytes were superfused with Ori buffer titrated to pH 6.5, the membrane potential of the oocytes was clamped to −40 mV, and inward current induced by superfusion with Ori buffer (pH 6.5) containing 5 mM of a control dipeptide or 5 mM of the tested tripeptide was measured.

(D) Expression and Purification of hRS1

Oocytes were injected with cRNA of hRS1 containing six histidine residues at the C-terminus. 3 days after expression, oocytes were homogenized and the nuclei and lipids removed by differential centrifugation as described (Valentin (2000), Biochim. Biophys. Acta, 1468, 367-380). Then, hRS1 was affinity-purified on nickel(II)-charged nitrilotriacetic acid-agarose from QIAGEN GmbH (Hilden, Germany) as described (Valentin (2000), Biochim. Biophys. Acta, 1468, 367-380). Purified hRS1 was dialysed against KOri buffer (in mM: 5 HEPES-Tris, pH 7.4, 100 KCl, 3 NaCl, 2 CaCl$_2$, and 1 MgCl$_2$).

(E) Inhibition of hSGLT1 Expressed [$^{14}$C]AMG Uptake by hRS1 Protein and Peptides of hRS1

Oocytes were injected with hSGLT1 cRNA (2.5 ng per oocyte) and incubated for 3 days in ORi buffer (16° C.). Thereafter, the oocytes were injected with 50 nl/oocyte of KOri buffer plus hRS1 protein or various concentrations of peptides derived from hRS1. Oocytes were incubated for 30 min or longer time periods at room temperature and uptake of [$^{14}$C]AMG was measured.

In a different experimental setup, oocytes were injected with SGLT1 cRNA (2.5 ng per oocyte) or with hSGLT1 cRNA (2.5 ng per oocyte) plus hPEPT1 cRNA (10 ng per oocyte) and the oocytes were incubated 3 days for expression. Thereafter the oocytes were incubated 30 min with Ori buffer adjusted to pH 6.5 or with Ori buffer adjusted to pH 6.5 containing 3 mM of the tested tripeptide. Thereafter oocytes were washed with Ori buffer (pH 7.4) and uptake of [$^{14}$C] AMG was measured.

(F) Measurements of [$^{14}$C]AMG Uptake

Uptake measurements were performed as described (Veyhl (2003), J. Membrane Biol., 196, 71-81). Oocytes were incubated for 15 min at room temperature in ORi buffer containing 50 µM [$^{14}$C]AMG without or with 100 µM of the SGLT1 inhibitor phlorizin. The uptake was blocked and oocytes were washed with ice cold Ori buffer containing 100 µM phlorizin. Radioactivity in the oocytes was measured by liquid scintillation counting.

Uptake measurements were performed in 7 to 10 individual oocytes and mean values±standard deviations of the means are indicated. Experiments were performed in triplicates or more often. Statistical significance of AMG uptake after coinjection of hRS1 derived cRNAs or after injection of hRS1 derived peptides was determined by Anova test and post hoc Tukey comparison.

(G) Immunostaining

For immunostaining, LLC-PK$_1$ cells were grown on coverslips to about 50% confluence. The cells were washed twice with washing buffer (5 mM 3-(N-morpholino)propane-sulfonic acid-NaOH, pH 7.4, 100 mM NaCl, 3 mM KCl, 2 mM CaCl$_2$, and 1 mM MgCl$_2$), fixed for 12 min with 4% (w/v) paraformaldehyde diluted in washing buffer, and washed twice again. Free aldehyde groups were quenched by 10 min incubation with washing buffer containing 40 mM glycine. For immunoreactions, washed cells were permeabilized by a 10-min incubation with washing buffer containing 0.25% (w/v) TritonX-114, and incubated over night at 4° C. with primary antibodies diluted in washing buffer. The dilutions of primary antibodies were as follows: rabbit-anti-RS1-Ab 1:50 (Valentin (2000), Biochim. Biophys. Acta, 1468, 367-380); QIS30 directed against SGLT1 1:400 (Kipp (2003), Am. J. Physiol., 285, C737-C749), sheep-anti-TGN46 1:125 (from Diagnostic International, Schriesheim, Germany). After incubation with primary antibodies, cells were washed 3 times with washing buffer and incubated for 1 h at room temperature with fluorochrome linked secondary antibodies (goat antibody against rabbit IgG linked to AlexaFluor 488 Molecular Probes, Leiden, Netherlands, and donkey anti-sheep IgG coupled to Cy2 from Dianova, Hamburg, Germany). Cells were washed 6 times with washing buffer, rinsed shortly with double-distilled water and embedded in Fluorescent-Mounting Medium from DAKO Diagnostika GmbH (Hamburg, Germany) containing 1 µl of 4',6'-diamidino-2-phenylindole (DAPI, Molecular Probes, Leiden, Netherlands) per specimen for staining of the nuclei.

The specificity of the antibodies was controlled as follows. The immunoreaction with affinity purified pRS1-ab was abolished after preabsorption with the antigen by incubating pRS1-ab for 60 min at 37° C. with 0.1 mg/ml of recombinant pRS1 protein. No antibody reaction with secondary antibodies was observed when the incubation with primary antibodies was omitted. In controls, no cross-reactivity of the used secondary antibodies with false primary antibodies used in the same experiment was detected.

Example 2

RS1 is a Brefeldin A-sensitive Coat Protein at the TGN

Colocalization experiments in human embryonic kidney 293 cells using specific antibodies against RS1 and the TGN marker protein TGN46 (Luzio (1990), Biochem. J., 270, 97-102; Banting and Ponnambalam (1997), Biochim. Biophys. Acta, 1355, 209-217) showed perfect colocalization of TGN46 and RS1 (data not shown). This indicated that RS1 is located at the TGN. brefeldin A is a fungal metabolite that has been extensively used to decipher vesicular transport processes in eukaryotic cells (Klaus (1992), J. Cell. Biol., 116, 1071-1080). The most striking effects of brefeldin A are the release of various coat proteins from the Golgi apparatus and morphological changes of intracellular tubulovesicular compartments that reflect changes in membrane traffic pathways. Targets of brefeldin A are guanosine nucleotide exchange factors (GEFs) that catalyse the conversion of inactive (ARF-GDP) into active ADP-ribosylation factors (ARF-GTP) (Helms J B and Rothman J E (1992) Nature 360, 352-354; Jackson C L and Casanova J E (2000) Cell Biology 10, 60-67). ARFs are Ras-like GTPases that are central to many vesicular transport processes in eucraryotic cells. They regulate the assembly of vesicle coat complexes on the TGN (Roth (1999), Cell, 97, 149-152). To determine whether RS1 belongs to the group of ARF dependent coat proteins at the TGN, subconfluent LLC-PK$_1$ cells were incubated for various time periods with 2 µg/ml BFA and immunostaining for SGLT1 and RS1 was performed (FIG. 1). After 1 min or 5 min incubation of subconfluent LLC-PK$_1$ cells with brefeldin A distinct morphology changes of the tubulovesicular compartments with SGLT1 immunoreactivity were observed. The relatively close packing of tubulovesicular compartments with SGLT1 observed in many cells became more dissociated and increasing numbers of single tubules with extensive ramification became apparent (FIG. 1 a-c). SGLT1 remained associated with the intracellular membranes. In contrast, the immunoreactivity of RS1 at the perinuclear compartment disappeared within several minutes after incubation of the LLC-PK$_1$ cells with brefeldin A. The data show that RS1 protein is released from the TGN by brefeldin A and suggest that RS1 is a GEF dependent coating protein at the TGN.

Example 3

Posttranscriptional Inhibition of the Expression of hSGLT1 by hRS1 is Due to an Effect on the Exocytotic Pathway Oocytes were injected with hSGLT1-cRNA and incubated for three days for expression. Then, 50 nl of KOri buffer was injected without addition, with 1.7 ng botulinustoxin B (BTXB), with 5 ng purified hRS1 protein, or with 5 ng of purified hRS1 plus 1.7 ng of BTXB. After 30 min incubation at room temperature uptake of 50 µM [$^{14}$C]AMG was measured (FIG. 2). In the absence of butolinustoxin, hRS1 inhibited hSGLT1 expressed AMG uptake by 50%. Under the employed experimental conditions the concentration of injected BTXB inhibited the expression of AMG uptake also by about 50%. In the presence of BTXB no inhibition of AMG uptake by injected hRS1 protein could be observed (FIG. 2). Because BTXB inhibits fusion of intracellular vesicles with the plasma membrane, the data suggest that the posttranscriptional inhibition of hSGLT1 by hRS1 is due to the inhibition of an exocytotic pathway. This interpretation was supported by experiments showing that inhibition of hSGLT1 expression by hRS1 protein in oocytes was independent of endocytotic pathways. Inhibition of hSGLT1 expressed AMG by injection of hRS1 protein was unchanged when endocytosis of hSGLT1 was inhibited by the inhibitors of endocytosis clorpromazin, imipramin or filipin (data not shown).

Example 4

A cRNA Fragment from the Middle Part of hRS1Encoding the Amino Acids QNEQCPQVS (SEQ ID NO: 17) Exhibits Post-transcriptional Inhibition of hSGLT1Mediated Glucose Uptake Non-injected oocytes, oocytes injected with hSGLT1-cRNA, oocytes injected with hSGLT1-cRNA plus hRS1-cRNA, or oocytes injected with hSGT1-cRNA plus cRNAs encoding fragments of hRS1 were incubated for three days and the uptake of 50 µM [14C]AMG was measured (FIG. 3). The uptake expressed by hSGLT1 was significantly by 50-70 % if hRS1 or fragments of hRS1 were co-expressed with hSGLT1. Inhibiton was obtained by a N-terminal and C-terminal cRNA fragments that oyerlap by 27 nucleotides (positions 1366-1392; Lambotte S et al., (1996) DNA Cell Biol. 15, 769-777). These nucleotides encode the mino acids QNEQCPQVS (SEQ ID NO: 17). Inhibition of [14C]AMG uptake expressed by hSGLT1 was also observed when a cRNA containing this overlapping part was co-expressed (nucleotides 1366-1392 of hRS1 expressing amino acids 407-415) with hSGLT1. The data indicate that glucose transport expressed by hSGLT1 is inhibited by a 27-nucleotide long cRNA fragments of hRS1 encoding the nonapeptide by QNEQCPQVS (SEQ ID NO: 17).

Example 5

Expression of hSGLT1 Mediated Glucose Transport is Inhibited by the Tripeptide QCP from the Middle Part of hRS1

To determine whether the observed inhibition of hSGLT1 by co-injection of hRS1-cRNA fragments occurs at the protein level, and to identify the minimal inhibitory peptide, hSGLT1 was expressed in oocytes, the indicated peptides were injected into the oocytes, and uptake measurements were started 30 min later. hSGLT1 was expressed by injection of 2.5 ng of hSGLT1-cRNA per oocyte and incubation of the oocytes was performed for 3 days. By injection of 50 nl/oocyte containing 1.5 mM of nonapeptide QNEQCPQVS (SEQ ID NO: 17), of the hexapeptides QNEQCP (SEQ ID NO: 18 l or QCPQVS (SEQ ID NO: 19), and of the tripeptide QCP, uptake of 50 pM [$^{14}$C]AMG was inhibited by 40-50% (FIG. 4). No inhibition was observed with the reverse nonapeptide SVQPCQENQ (SEQ ID NO: 29) and with the reversed tripeptide PCQ. The data indicate that glucose uptake by hSGLT1 can be inhibited from intracellular by the tripeptide QCP.

Example 6

Demonstration of High-affinity Inhibition of hSGLT1 by QCP

To determine the affinity of QCP to inhibit glucose uptake by hSGLT1, hSGLT1 was expressed by injection of SGLT1-cRNA into oocytes and an incubation of the injected oocytes for 3 days. Then, 50 nl Ori buffer per oocyte (control) or 50 nl Ori buffer containing various concentrations of the tripeptide QCP or the reverse tripeptide PCQ were injected. 30 min later, the uptake of 50 µM [$^{14}$C]AMG was measured (FIG. 5). 35-40% inhibition of hSGLT1 expressed AMG uptake was obtained after injection of 50 nl with a QCP concentration of 50 nM. Since the volume of an oocyte is about 1 µl, 35-40% inhibition of hSGLT1 expressed glucose uptake was obtained at an intracellular concentration of QCP below 5 nM. With the reverse tripeptide PCQ no inhibition of hSGLT1 was observed.

Example 7

QCP is Transported by the Human H$^+$-peptide Cotransporter hPEPT1

To determine whether QCP is transported by the human peptide transporter hPEPT1 that is expressed in the brush-border membrane of small intestinal enterocytes (Daniel and Kottra (2004), Pflugers Arch, 447, 610-618; Liang (1995), J Biol Chem, 270, 6456-6463) hPEPT1 was expressed in *Xenopus* oocytes, the oocyte was superfused with acid Ori buffer (pH 6.5), the membrane potential of the oocytes was clamped to −40 mV and the oocyte was superfused with acid Ori buffer (pH 6.5) containing 5 mM of well transported control dipeptide glycylglutamine (GC) or 5 mM of QCP. In oocytes expressing hPEPT1, both the control peptide GC and the dipeptide QCP induced significant inward currents (FIG. 6). In control oocytes that had not been injected with hPEP1-cRNA, no inward currents could be induced by GC or QCP (data not shown). The data indicate electrogenic transport of QCP by hPEPT1.

Example 8

QCP Added to the Extracellular Fluid can Inhibit hSGLT1 in Cells that Express hPEPT1

It was furthermore elucidated whether in human small intestine the expression of hSGLT1 can be inhibited by oral ingestion of QCP. In human small intestine both, hSGLT1 and hPEPT1 are located in the brush-border membrane of enterocytes (Wright and Turk (2004), Pflugers Arch, 447, 510-518; Daniel and Kottra (2004), Pflugers Arch, 447, 610-618). hSGLT1 was expressed alone or SGLT1 together with hPEPT1 in *Xenopus* oocytes, incubated the oocytes for 30 min acid Ori buffer (pH 6.5), with acid Ori buffer containing 3 mM QCP or inactive reverse peptide PCQ. Thereafter the oocytes were washed with neutral Ori buffer and the hSGLT1 expressed uptake of 50 µM [$^{14}$C]AMG was measured (FIG. 7). QCP had no effect in oocytes in which hSGLT1 but not hPEPT1 was expressed (data not shown). However, in oocytes expressing hSGLT1 plus hPEPT1, [$^{14}$C]AMG uptake was inhibited by about 50% when the oocytes had been incubated with QCP (FIG. 7). Incubation of oocytes expressing hSGLT1 plus hPEPT1 with PCQ had no effect on the expressed uptake of [$^{14}$C]AMG.

Example 9

QCP Inhibits the Expression of hSGLT1 for a Time Period of Several Hours hSGLT1 was expressed by injection of SGLT1-cRNA into oocytes and incubation of the injected oocytes for 3 days. Then 50 nl Ori buffer or 50 nl Ori buffer containing 3 mM QCP were injected per oocyte. 3-11 h after the injections uptake of 50 µM [$^{14}$C]AMG was measured. FIG. 8 shows that the hSGLT1 expressed uptake of AMG was inhibited 60% after 3 h, about 40% after 5 h and 20-30% after 10 h.

Example 10

Posttranscriptional Inhibition of the Expression of hSGLT1 by QCP can be Inhibited by Botulinum Toxin B To distinguish whether QCP inhibits expression of hSGLT1 by blocking an exocytotic pathway at the TGN or whether QCP stimulates endocytosis of SGLT1 containing vesicles at the plasma membrane, hSGLT1 was expressed in oocytes and measured the effect of injected QCP in the absence and presence of botulinum toxin B (BTXB) (FIG. 9). hSGLT1 was expressed, KOri buffer as control, KOri buffer containing QCP, KOri buffer containing the reversed control peptide PCQ, KOri buffer containing BTXB or KOri buffer containing BTXB plus QCP was injected. After 30 min incubation, uptake of 50 µM [$^{14}$C] AMG was measured. FIG. 9 shows that in the absence of BTXB AMG uptake was inhibited by QCP but not by the reversed control peptide PCQ as shown in FIGS. 4 and 5. However, no significant inhibition of AMG uptake by QCP could be observed in the presence of BTXB. Because BTXB inhibits exocytotic fusion of intracellular vesicles with the plasma membrane QCP acts probably on the exocytotic pathway of hSGLT1. The location of hRS1 at the TGN suggests that QCP inhibits SGLT1 expression at the TGN.

Example 11

QCP Inhibits the Small Intestinal D-glucose Reabsorption by SGLT1 In Vivo

Walls of small intestinal mucosa from mice are inserted into an Ussing chamber and the SGLT1 mediated transepitehila currents are measured that are induced by addition of 0.1 mM D-glucose to the mucosal side. The intestinal walls are pre-incubated for 60 min with buffer at pH 6.5 containing 0.1 mM D-glucose or with buffer at pH 6.5 containing 0.1 mM D-glucose plus 3 mM of QCP. After washing glucose-induced transepithelial currents are measured. The data will document that QCP inhibits transepithelial glucose flux in vivo.

Example 12

QCP Inhibits the Small Intestinal Reabsorption of Amino Acids Mediated by Sodium Dependent Amino Acid Transporters In Vivo Walls of small intestinal mucosa from mice are inserted into an Ussing chamber and transepitehial currents are measured that are induced by addition of 10 mM of various amino acids to the mucosal side. The intestinal walls are incubated for 60 min with buffer at pH 6.5 containing 0.1 mM D-glucose or with buffer at pH 6.5 containing 0.1 mM D-glucose plus 3 mM of QCP. After washing, amino acid induced transepithelial currents without and with pretreatment with QCP are compared. The data would document that QCP inhibits transepithelial flux of amino acids in vivo.

Example 13

The Peptides IKPSDSDRIEP (SEQ ID NO: 10) and SDSDRIEP (SEQ ID NO: 9) from the N-terminal Part of hRS1Exhibit Post-transcriptional inhibition of hSGLT1Mediated Glucose Uptake In Oocytes of Xenopus laevis inhibition of expressed glucose transport was also observed when hSGLT1cRNA was injected with cRNAs encoding various N-terminal fragments of hRS1 (data not shown). FIG. 10 presents an experiment showing that an N-terminal fragment of hRS1encoding an unodecapeptide inhibits the expression of hSGLT1. Coexpression of hRS1cRNA encoding amino acids 40-50 of hRS1 (IKPSDSDRIEP) (SEQ ID NO: 10) resulted in a significant inhibition of hSGLT1 expressed of glucose uptake by more than 50%. The same level of inhibition was obtained when hSGLT1 was coexpressed with total hRS1.

It was tested, whether glucose transport expressed by hSGLT1in oocytes could be also inhibited by injection of the unodecapeptide IKPSDSDRIEP (SEQ ID NO: 10) and the octapeptide SDSDRIEP (SEQ ID NO: 9). After hSGLT1cRNA injection into oocytes and incubation for 3days, 50 nl/oocyte of KOri buffer without peptides or of KOri buffer containing 3mM QCP, 3mM IKPSDSDRIEP (SEQ ID NO: 10), 3 mM SDSDRIEP (SEQ ID NO: 9),3 mM QCP plus 3mM IKPSDSDRIEP (SEQ ID NO: 10) or 3 mM of the reverse tripeptide PCQ plus 3 mM of the reverse peptide PEIRDSDSPKI (SEQ ID NO: 30) were injected. After injection of peptides the oocytes were incubated for 30min and the uptake of 50 µM [$^{14}$C]AMG was measured (FIG. 11). With the unodecapeptide IKPSDSDRIEP (SEQ ID NO: 10) and the octapeptide SDSDRIEP (SEQ ID NO: 9), about 50% inhibition of glucose uptake was observed as with QCP. The data show that two peptides of hRS1are capable to inhibit hSGLT1. Since coinjection of both peptides QCP and IKPSDSDRIEP (SEQ ID NO: 10) did not lead to a lower uptake as the injection of each individual peptide, both peptides are supposed to act on the same intracellular regulation process.

Example 14

Inhibitory Peptides QCP and IKPSDSDRIEP (SEQ ID NO: 10) Derived from hRS1 Exhibit Species Independent Inhibition of SGLT1

To develop drugs on the basis of the identified peptides animal models are required. Since the peptides QCP and IKPSDSDRIEP (SEQ ID NO: 10) are derived from human RS1and are not conserved in RS1proteins of other species it was tested whether these peptides are capable to inhibit SGLT1in rabbits that could be used as an animal model for drug development. Rabbit SGLT1 (rbSGLT1) was expressed in oocytes by injection of rbSGLT1cRNA, the oocytes were incubated for 3days, and 50 nl KOri buffer/oocyte containing 3 mM QCP, 3 mM IKPSDSDRIEP (SEQ ID NO: 10), 3 mM QCP plus 3 mM IKPSDSDRIEP (SEQ ID NO: 10), or 3 mM of the reverse tripeptide PCQ plus 3 mM of the reverse peptide PEIRDSDSPKI (SEQ ID NO: 30) were injected, the oocytes were incubated for 30 min, and the uptake of 50 µM [$^{14}$C]AMG was measured (FIG. 12). Both peptides showed the same effect on glucose uptake expressed by rbSGLT1compared to glucose uptake expressed by hSGLT1 (FIG. 11). Injection of both peptides together revealed the same inhibition as injection of each peptide alone. No inhibition of rbSGLT1expressed glucose uptake was observed when both reverse peptides were injected.

Example 15

Inhibition of Nutrient Transporters in Small Intestine Lead to Reduction of Body Weight Mice are fed with standard chow (Altromin C1000 containing 32% polysaccharides, 5.5% disaccharides, 19% protein, 6% fiber, 4% fat, obtained from Altromin GmbH Lage, Germany) or sugar low diet (modified Altromin C 1000 containing 10% polysaccharides, no disaccharides, 19% protein, 6% fiber, increased amount of fat so that the energy content of both diets was identical) and the supplied drinking water is acidified to pH 6.0 and contains 10 mM QCP. The body weight development with and without peptide treatment is compared over 2 months. In addition intestinal motility is compared by measuring the passage time as described in Chen, 2001 (The Journal of Neurosciences, 21, 6348-6361). The data should document that body weight is reduced after feeding with QCP. In corresponding experiments, rabbits are to be employed.

Example 16

Inhibition of SGLT1 in Human Epithelial Cells by QCP

CaCo-2 cells were grown 13 days after seeding as described (Müller, J. et al. (2005) Biochem. Pharmacol. 70, 1851-1860). 3 days after seeding cells reached confluence. Cells were detached by incubation in PBS (pH. 7.4) containing 2 mM EDTA. They were washed two times by incubation with PBS that was adjusted to pH 6.5 and contained 10 mM AMG, and centrifugation at 1000×g. Cells were incubated for 30 min with PBS (pH 6.5) containing 10 mM AMG (control)

or PBS (pH 6.5) containing 10 mM AMG plus 1 mM QCP. Thereafter the cells were washed three times with PBS (pH 7.5) and AMG uptake was measured by incubation for 2.5 min in PBS (pH 7.5) containing 10 μM [$^{14}$C]AMG without or with 1 mM phlorizin. SGLT1 mediated uptake was measured by subtracting the uptake in the presence of phlorizin from the uptake without phlorizin. The data indicate that QCP inhibits AMG uptake by SGLT1 in human epithelial cells in the presence of a high intracellular concentration of glucose (see FIG. 13).

Example 17

Glucose Dependence of Inhibition of SGLT1 Mediated AMG Uptake by QCP hSGLT1 was expressed in oocytes by cRNA injection and incubation for 3 days as in FIG. 3/Example 1. Per oocyte 25 nl Ori buffer (injected sugar 0 M), 25 nl Ori buffer containing 2 mM (injected sugar $10^{-4}$ M), 20 mM (injected sugar $10^{-3}$ M) or 200 mM (injected sugar $10^{-2}$ M) of AMG (○), D-glucose (Δ) or D-fructose (□) were injected. In addition 25 nl Ori buffer or 25 nl Ori buffer containing 3 mM QCP were injected. The oocytes were incubated for 30 min and uptake of 50 μM [$^{14}$C]AMG was measured. Inhibition by QCP in the presence of different concentrations of intracellular monosaccharides was measured. The data indicate that QCP inhibits hSGLT1 at low or high concentrations of intracellular monosaccharides (see FIG. 14).

Example 18

Inhibition of hSGLT1 Expressed Glucose Transport Activity in Oocytes by QCP and QCP Derived Tripeptides Oocytes were injected with 2.5 ng hSGLT1-cRNA, incubated for 3 days and 50 nl of buffer (control) or 50 nl of buffer containing 1.5 mM of the indicated peptides (resulting in approximately 75 pmoles of peptides per oocyte) were injected. For each injected peptide, 3 individual experiments with 7-10 buffer-injected control oocytes and 7-10 peptide injected oocytes were performed. The uptake measurements were performed with 50 μM [$^{14}$C]AMG. The corresponding results are shown in FIG. 15.

The present invention refers to the following nucleotide and amino acid sequences:
SEQ ID No. 1:
Nucleotide sequence encoding for human RS1 (hRS1) (regulatory solute carrier protein, family 1, member 1 (*Homo sapiens*)).

```
atgagcagcctgccgaccagcgatggctttaaccatccggcgcgcagcagcggccagagcccggatgtgggcaac ccgatgagcctggcgcgcagcgtgagcgcgagcgtgtgcccgattaaaccgagcgatagcgatcgcattgaaccg aaagcggtgaaagcgctgaaagcgagcgcggaatttcagctgaacagcgaaaaaaaagaacatctgagcctgcag gatctgagcgatcatgcgagcagcgcggatcatgcgccgaccgatcagagcccggcgatgccgatgcagaacagc agcgaagaaattaccgtggcgggcaacctggaaaaaagcgcggaacgcagcacccagggcctgaaatttcatctg catacccgccaggaagcgagcctgagcgtgaccagcacccgcatgcatgaaccgcagatgtttctgggcgaaaaa gattggcatccggaaaaccagaacctgagccaggtgagcgatccgcagcagcatgaagaaccgggcaacgaacag tatgaagtggcgcagcagaaagcgagccatgatcaggaatatctgtgcaacattggcgatctggaactgccggaa gaacgccagcagaaccagcataaaattgtggatctggaagcgaccatgaaaggcaacggcctgccgcagaacgtg gatccgccgagcgcgaaaaaaagcattccgagcagcgaatgcagcggctgcagcaacagcgaaacctttatggaa attgataccgcgcagcagagcctggtgaccctgctgaacagcaccggccgccagaacgcgaacgtgaaaaacatt ggcgcgctggatctgaccctggataacccgctgatggaagtggaaaccagcaaatgcaacccgagcagcgaaatt ctgaacgatagcattagcacccaggatctgcagccgccggaaaccaacgtggaaattccgggcaccaacaaagaa tatggccattatagcagcccgagcctgtgcggcagctgccagccgagcgtggaaagcgcggaagaaagctgcccg agcattaccgcggcgctgaaagaactgcatgaactgctggtggtgagcagcaaaccggcgagcgaaaacaccagc gaagaagtgatttgccagagcgaaaccattgcggaaggccagaccagcattaaagatctgagcgaacgctggacc cagaacgaacatctgacccagaacgaacagtgcccgcaggtgagctttcatcaggcgattagcgtgagcgtggaa accgaaaaactgaccggcaccagcagcgataccggccgcgaagcggtggaaaacgtgaactttcgcagcctgggc gatggcctgagcaccgataaagaaggcgtgccgaaaagccgcgaaagcattaacaaaaaccgcagcgtgaccgtg accagcgcgaaaaccagcaaccagctgcattgcaccctgggcgtggaaattagcccgaaactgctggcgggcgaa gaagatgcgctgaaccagaccagcgaacagaccaaaagcctgagcagcaactttattctggtgaaagatctgggc cagggcattcagaacagcgtgaccgatcgcccggaaaccccgcgaaaacgtgtgcccggatgcgagccgcccgctg ctggaatatgaaccgccgaccagccatccgagcagcagcccggcgattctgccgccgctgattttccggcgacc gatattgatcgcattctgcgcgcgggctttaccctgcaggaagcgctgggcgcgctgcatcgcgtgggcggcaac gcggatctggcgctgctggtgctgctggcgaaaaacattgtggtgccgacc
```

SEQ ID No. 2:
Amino acid sequence of human RS1 (hRS1) (regulatory solute carrier protein, family 1, member 1 (*Homo sapiens*)).

```
MSSLPTSDGFNHPARSSGQSPDVGNPMSLARSVSASVCPIKPSDSDRIEPKAVKALKASAEFQLNSEKKEHLSLQ

DLSDHASSADHAPTDQSPAMPMQNSSEEITVAGNLEKSAERSTQGLKFHLHTRQEASLSVTSTRMHEPQMFLGEK

DWHPENQNLSQVSDPQQHEEPGNEQYEVAQQKASHDQEYLCNIGDLELPEERQQNQHKIVDLEATMKGNGLPQNV

DPPSAKKSIPSSECSGCSNSETFMEIDTAQQSLVTLLNSTGRQNANVKNIGALDLTLDNPLMEVETSKCNPSSEI

LNDSISTQDLQPPETNVEIPGTNKEYGHYSSPSLCGSCQPSVESAEESCPSITAALKELHELLVVSSKPASENTS

EEVICQSETIAEGQTSIKDLSERWTQNEHLTQNEQCPQVSFHQAISVSVETEKLTGTSSDTGREAVENVNFRSLG

DGLSTDKEGVPKSRESINKNRSVTVTSAKTSNQLHCTLGVEISPKLLAGEEDALNQTSEQTKSLSSNFILVKDLG

QGIQNSVTDRPETRENVCPDASRPLLEYEPPTSHPSSSPAILPPLIFPATDIDRILRAGFTLQEALGALHRVGGN

ADLALLVLLAKNIVVPT
```

SEQ ID No. 3:
Nucleotide sequence encoding for pig RS1 (pRS1) (sodium-glucose cotransporter regulatory chain RS1-pig (*Sus scrofa domestica*).

```
atgagcagcctgccgaccagcgatggctttaaccatcaggcgcatccgagcggccagcgcccggaaattggcagc ccgccgagcctggcgcatagcgtgagcgcgagcgtgtgcccgtttaaaccgagcgatccggatagcattgaaccg aaagcggtgaaagcggtgaaagcgctgaaagcgagcgcggaatttcagattacctttgaacgcaaagaacagctg ccgctgcaggatccgagcgattgcgcgagcagcgcggataacgcgccggcgaaccagaccccggcgattccgctg cagaacagcctggaagaagcgattgtggcggataacctggaaaaaagcgcggaaggcagcacccagggcctgaaa agccatctgcatacccgccaggaagcgagcctgagcgtgaccaccacccgcatgcaggaaccgcagcgcctgatt ggcgaaaaaggctggcatccggaatatcaggatccgagccaggtgaacggcctgcagcagcatgaagaaccgcgc aacgaacagcatgaagtggtgcagcagaacgcgccgcatgatccggaacatctgtgcaacaccggcgatctggaa ctgctgggcgaacgccagcagaaccagccgaaaagcgtgggcctggaaaccgcggtgcgcggcgatcgcccgcag caggatgtggatctgccgggcaccgaaaaaaacattctgccgtatggctgctttggctgcagcagcagcgaaacc tttatggaaattgataccgtggaacagagcctggtggcggtgctgaacagcgcgggcggccagaacaccagcgtg cgcaacattagcgcgagcgatctgaccgtggataacccgctgatggaagtggaaaccctgaaatgcaacccgagc agcgaatttctgagcaacccgaccagcacccagaacctgcagctgccggaaagcagcgtggaaatgagcggcacc aacaaagaatatggcaaccatccgagcagcctgagcctgtgcggcacctgccagccgagcgtggaaagcgcggaa gaaagctgcagcagcattaccgcggcgctgaaagaactgcatgaactgctggtgattagcagcaaaccggcgctg gaaaacaccagcgaagaagtgacctgccgcagcgaaattgtgaccgaaggccagaccgatgtgaaagatctgagc gaacgctggacccagagcgaacatctgaccgcggcgcagaacgaacagtgcagccaggtgagctttatcaggcg accagcgtgagcgtgaaaaccgaagaactgaccgataccagcaccgatgcgggcaccgaagatgtggaaaacatt accagcagcggcccgggcgatggcctgctggtggataaagaaaacgtgccgcgcagccgcgaaagcgtgaacgaa agcagcctggtgaccctggatagcgcgaaaaccagcaaccagccgcattgcaccctgggcgtggaaattagcccg ggcctgctggcgggcgaagaaggcgcgctgaaccagaccagcgaacagaccgaaagcctgagcagcagctttatt ctggtgaaagatctgggccagggcacccagaacccggtgaccaaccgcccggaaacccgcgaaaacgtgtgcccg gaagcggcgggcctgcgccaggaatttgaaccgccgaccagccatccgagcagcagcccgagctttctggcgccg ctgattttccggcggcggatattgatcgcattctgcgcgcgggctttacccctgcaggaagcgctgggcgcgctg catcgcgtgggcggcaacgcggatctggcgctgctggtgctgctggcgaaaaacat
tgtggtgccgacc
```

SEQ ID No. 4:
Amino acid sequence of pig RS1 (pRS1) (sodium-glucose cotransporter regulatory chain RS1-pig (*Sus scrofa domestica*).

MSSLPTSDGFNHQAHPSGQRPEIGSPPSLAHSVSASVCPFKPSDPDSIEPKAVKAVKALKASAEFQITFERKEQL

PLQDPSDCASSADNAPANQTPAIPLQNSLEEAIVADNLEKSAEGSTQGLKSHLHTRQEASLSVTTTRMQEPQRLI

GEKGWHPEYQDPSQVNGLQQHEEPRNEQHEVVQQNAPHDPEHLCNTGDLELLGERQQNQPKSVGLETAVRGDRPQ

QDVDLPGTEKNILPYGCFGCSSSETFMEIDTVEQSLVAVLNSAGGQNTSVRNISASDLTVDNPLMEVETLKCNPS

SEFLSNPTSTQNLQLPESSVEMSGTNKEYGNHPSSLSLCGTCQPSVESAEESCSSITAALKELHELLVISSKPAL

ENTSEEVTCRSEIVTEGQTDVKDLSERWTQSEHLTAAQNEQCSQVSFYQATSVSVKTEELTDTSTDAGTEDVENI

TSSGPGDGLLVDKENVPRSRESVNESSLVTLDSAKTSNQPHCTLGVEISPGLLAGEEGALNQTSEQTESLSSSFI

LVKDLGQGTQNPVTNRPETRENVCPEAAGLRQEFEPPTSHPSSSPSFLAPLIFPAADIDRILRAGFTLQEALGAL

HRVGGNADLALLVLLAKNIVVPT

20

SEQ ID No. 5:
Nucleotide sequence encoding for mouse RS1 (mRS1) (regulatory subunit of SGLT1 (*Mus musculus*)).

atgagcagcctgccgaccagcgatggctttgatcatccggcgccgagcggccagagcccggaagtgggcagcccg accagcctggcgcgcagcgtgagcgcgagcgcgtgcgcgattaaaccgggcgatccgaacagcattgaaagcctg gcgatgcaggcgaccaaagcgagcgcggaatttcagaccaacagcaaaaaaaccgatccgccgccgctgcaggtg ctgccggatctggcgagcagcgcggaacagagcctggcgatgccgtttcataaaagcagcaaagaagcggtggtg gcgggcaacctggaaaaaagcgtggaaaaaggcacccagggcctgcgcgtgtatctgcatacccgccaggatgcg agcctgaccctgaccaccaccggcatgcgcgaaccgcagattttgcggaagaaaaagctggcatccggaaaac cagaccccgagcccggtgaacggcctgcagcagcatcgcgaaaccggcagcgtgcagcgcgaagcgggccagcag agcgtgccgcaggatcagggctgcctgtgcgatgcggaagatctggaactgcatgaagaagtggtgagcctggaa gcgctgcgcaaaggcgaactgcagcgccatgcgcatctgccgagcgcggaaaaaggcctgccggcgagcggcctg tgcagctgcccgtgcagcgaagcgctgatggaagtggataccgcggaacagagcctggtggcgatgtgcagcagc accggccgccaggatgcggtgattaaaagcccgagcgtggcgcatctggcgagcgataacccgaccatggaagtg gaaaccctgcagagcaacccgagctgcgaaccggtggaacatagcattctgacccgcgaactgcagctgccggaa gataacgtggatatgagcaccatggataacaaagatgataacagcagcagcctgctgagcggccatggccagccg agcgtggaaagcgcggaagaattttgcagcagcgtgaccgtggcgctgaaagaactgcatgaactgctggtgatt agctgcaaaccggcgagcgaagaaagcccggaacatgtgacctgccagagcgaaattggcgcggaaagccagccg agcgtgagcgatctgagcggccgccgcgtgcagagcgtgcatctgaccccgagcgatcagtatagccagggcagc tgccatcaggcgaccagcgaaagcggcaaaaccgaaattgtgggcaccgcgccgtgcgcggcggtggaagatgaa gcgagcaccagctttgaaggcctgggcgatggcctgagcccggatcgcgaagatgtgcgccgcagcaccgaaagc gcgcgcaaaagctgcagcgtggcgattaccagcgcgaaactgagcgaacagctgccgtgcaccctgggcgtggaa attgcgccggaactggcggcgagcgaaggcgcgcatagccagccgagcgaacatgtgcataacccgggcccggat cgcccggaaaccagcagcgtgtgcccgggcgcgggcctgccgcgcagcggcctggatcagccgccgacccagagc ctgagcaccccgagcgtgctgccgccgtttatttttccggcggcggatgtggatcgcattctgggcgcgggctttt accctgcaggaagcgctgggcgcgctgcatcgcgtgggcggcaacgcggatctggcgctgctggtgctgctggcg aaaaacattgtggtgccgacc SEQ ID No. 6:
  Amino acid sequence of mouse RS1 (mRS1) (regulatory subunit of SGLT1 (*Mus musculus*)).

MSSLPTSDGFDHPAPSGQSPEVGSPTSLARSVSASACAIKPGDPNSIESLAMQATKASAEFQTNSKKTDPPPLQV

LPDLASSAEQSLAMPFHKSSKEAVVAGNLEKSVEKGTQGLRVYLHTRQDASLTLTTTGMREPQIFAEEKSWHPEN

QTPSPVNGLQQHRETGSVQREAGQQSVPQDQGCLCDAEDLELHEEVVSLEALRKGELQRHAHLPSAEKGLPASGL

CSCPCSEALMEVDTAEQSLVAMCSSTGRQDAVIKSPSVAHLASDNPTMEVETLQSNPSCEPVEHSILTRELQLPE

DNVDMSTMDNKDDNSSSLLSGHGQPSVESAEEFCSSVTVALKELHELLVISCKPASEESPEHVTCQSEIGAESQP

SVSDLSGRRVQSVHLTPSDQYSQGSCHQATSESGKTEIVGTAPCAAVEDEASTSFEGLGDGLSPDREDVRRSTES

ARKSCSVAITSAKLSEQLPCTLGVEIAPELAASEGAHSQPSEHVHNPGPDRPETSSVCPGAGLPRSGLDQPPTQS

LSTPSVLPPFIFPAADVDRILGAGFTLQEALGALHRVGGNADLALLVLLAKNIVVPT

SEQ ID No. 7:
  Nucleotide sequence encoding for rabbit RS1 (rbRS1) (regulatory subunit of sodium-D-glucose cotransporter (*Oryctolagus cuniculus*)).

atgagcagcagcccgccgctggatggcagcgatcatccggcgcatagcagcggccagagcccggaagcgggcaac ccgaccagcctggcgcgcagcgtgagcgcgagcgtgtgcccggtgaaaccggataacccggatagcaccgaaccg gaagcggtgaccgcgctggaagcgagcgatggctttcagattaacagcaaacagaccgatcgcctgccgctgcag ggccatagcccgtgcgcggcggcggcggcgccgagcagcgcgatgccgctgcgccatagcagcgaagcggcgggc gtggcggatagcctggaagcgagcgcggaacgccgcacccagggcctgcgctttcatctgcatacccgccaggaa gtgaacctgagcattaccaccacccgcatgcatgaaccgcagatgtttgcgggcgaagaaggctggcatccggaa aaccagaacccgagccaggtgaacgatctgcagcagcatcaggaaccggaaaacgcgcgccatgaagcgggcccg cgcgatgcgccgagcgataccggcgatctggaactgccgggcgaacgccagcagaaacatgaagtggcggatcgc gaagcgaccatgcgcggcggccgcctgcagcaggatgcgggcctgccggatccgggcaaaggcgcgctgccgagc ggccattgcggccgcccggatagcgaaaccctgatggaagtggatgcggcggaacagagcctggtggcggtgctg agcagcagcgtgggcaacggcagcgcgagcggcctgaccctgggcaacccgctgatggaagtggaactgccgacc tgcagcccgagcagcgaaattctgaacggcagcattccgattcaggatctgcagccgccggaaggcagcgtggaa atgccgggcaccgatcgcgcgtatggcggccgcgcgagcagcagcagcgtgtgcggcagcagccagccgccggcg gaaagcgcggaagaaagctgcagcagcattaccaccgcgctgaaagaactgcatgaactgctggtgattagcagc aaaccggcgagcgaagcggcgtatgaagaagtgacctgccagagcgaaggcaccgcgtggggccagacccgcgtg aacccgagcgaacgctggaccgaaagcgaacgccgcacccaggatgaagatcgcccgcaggtgagccatgcgatt ccggaatgcgtgaaaaccgaaaaactgaccgatgcgagcccggatacccgcattgaagatggcgaaaacgcgacc tttcagggcccgggcggcggcctgagcaccgatcatggcgcgccgcgcagccgcggcagcgtgcatgaaagccgc agcgtgaccgtgaccagcgcggaaaccagcaaccagagccatcgcaccctgggcgtggaaattagcccgcgcctg ctgaccggcgaaggcgatgcgctgagccagacctgcgaacagaccaaaagcctgctggtgaaagatctgggccag ggcacccagaacccggcgccggatcgcccggcgacccgcgaagatgtgtgccgcgatgcggcgcccgagcctg gaagtggaagcgccgccgagccatagcagcggcccgtgcattctgccgccgctgggctttccggcggcggatatt gatcgcattctgcgcgcgggctttacccctgcaggaagcgctgggcgcgctgcatcgcgtgggcggcaacgcggat ctggcgctgctggtgctgctggcgaaaaacattgtggtgccgacc SEQ ID No. 8:
Amino acid sequence of rabbit RS1 (rbRS1) (regulatory subunit of sodium-D-glucose cotransporter (*Oryctolagus cuniculus*)).

MSSSPPLDGSDHPAHSSGQSPEAGNPTSLARSVSASVCPVKPDNPDSTEPEAVTALEASDGFQINSKQTDRLPLQ

GHSPCAAAAAPSSAMPLRHSSEAAGVADSLEASAERRTQGLRFHLHTRQEVNLSITTTRMHEPQMFAGEEGWHPE

NQNPSQVNDLQQHQEPENARHEAGPRDAPSDTGDLELPGERQQKHEVADREATMRGGRLQQDAGLPDPGKGALPS

GHCGRPDSETLMEVDAAEQSLVAVLSSSVGNGSASGLTLGNPLMEVELPTCSPSSEILNGSIPIQDLQPPEGSVE

MPGTDRAYGGRASSSSVCGSSQPPAESAEESCSSITTALKELHELLVISSKPASEAAYEEVTCQSEGTAWGQTRV

NPSERWTESERRTQDEDRPQVSHAIPECVKTEKLTDASPDTRIEDGENATFQGPGGGLSTDHGAPRSRGSVHESR

SVTVTSAETSNQSHRTLGVEISPRLLTGEGDALSQTCEQTKSLLVKDLGQGTQNPAPDRPATREDVCRDAARPSL

EVEAPPSHSSGPCILPPLGFPAADIDRILRAGFTLQEALGALHRVGGNADLALLVLLAKNIVVPT

---

The invention claimed is:

1. A method for the treatment of obesity, hypercholesterolemia, diabetes or hyperglycaemia, comprising administering to a patient in need of such treatment a therapeutically effective amount of a peptide consisting of an amino acid sequence selected from the group consisting of:

(a) Q-C-P;
(b) Q-N-E-Q-C-P (SEQ ID NO: 18);
(c) Q-C-P-Q-V-S (SEQ ID NO: 19);
(d) Q-N-E-Q-C-P-Q-V-S (SEQ ID NO: 17);
(e) Q-S-P;
(f) Q-P-P;
(g) Q-T-P.

2. The method of claim 1, wherein said peptide is Q-C-P, Q-S-P, Q-P-P or Q-T-P.

3. The method of claim 1, wherein said peptide is administered to a human patient.

4. The method of claim 1, wherein said peptide is administered in a concentration of $2 \times 10^{-9}$ M to 5 M.

5. The method of claim 1, wherein said peptide is administered orally, rectally, topically, intranasally, intrapulmonary, vaginally, intravesically, subcutaneously, intravenously or cutaneously.

6. The method of claim 1, wherein said peptide is administered orally.

7. The method of claim 1, wherein said peptide is administered with a pharmaceutically acceptable carrier.

8. The method of claim 7, wherein said pharmaceutically acceptable carrier releases said peptide within the small intestine, renal proximal tubules, colon, rectum or bladder.

9. The method of claim 8, wherein said pharmaceutically acceptable carrier releases said peptide within the small intestine.

10. The method of claim 7, wherein said pharmaceutically acceptable carrier comprises a gastric-juice resistant tablet.

11. The method of claim 1, wherein said peptide interacts with a receptor, transporter and/or channel selected from the group consisting of receptors, transporters and/or channels for sugars, amino acids, peptides, neurotransmitters, vitamins, organic ions, inorganic ions, zwitterions, urea, water, protons and drugs.

* * * * *

SEQUENCE LISTING

<160> NUMBER OF SEQ ID NOS: 30

<210> SEQ ID NO 1
<211> LENGTH: 1851
<212> TYPE: DNA
<213> ORGANISM: Homo sapiens
<220> FEATURE:
<221> NAME/KEY: CDS
<222> LOCATION: (1)..(1851)

<400> SEQUENCE: 1

```
atg agc agc ctg ccg acc agc gat ggc ttt aac cat ccg gcg cgc agc        48
Met Ser Ser Leu Pro Thr Ser Asp Gly Phe Asn His Pro Ala Arg Ser
1               5                   10                  15 agc ggc cag agc ccg gat gtg ggc aac ccg atg agc ctg gcg cgc agc        96
Ser Gly Gln Ser Pro Asp Val Gly Asn Pro Met Ser Leu Ala Arg Ser
            20                  25                  30 gtg agc gcg agc gtg tgc ccg att aaa ccg agc gat agc gat cgc att       144
Val Ser Ala Ser Val Cys Pro Ile Lys Pro Ser Asp Ser Asp Arg Ile
        35                  40                  45 gaa ccg aaa gcg gtg aaa gcg ctg aaa gcg agc gcg gaa ttt cag ctg       192
Glu Pro Lys Ala Val Lys Ala Leu Lys Ala Ser Ala Glu Phe Gln Leu
    50                  55                  60 aac agc gaa aaa aaa gaa cat ctg agc ctg cag gat ctg agc gat cat       240
Asn Ser Glu Lys Lys Glu His Leu Ser Leu Gln Asp Leu Ser Asp His
65                  70                  75                  80 gcg agc agc gcg gat cat gcg ccg acc gat cag agc ccg gcg atg ccg       288
Ala Ser Ser Ala Asp His Ala Pro Thr Asp Gln Ser Pro Ala Met Pro
                85                  90                  95 atg cag aac agc agc gaa gaa att acc gtg gcg ggc aac ctg gaa aaa       336
Met Gln Asn Ser Ser Glu Glu Ile Thr Val Ala Gly Asn Leu Glu Lys
            100                 105                 110 agc gcg gaa cgc agc acc cag ggc ctg aaa ttt cat ctg cat acc cgc       384
Ser Ala Glu Arg Ser Thr Gln Gly Leu Lys Phe His Leu His Thr Arg
        115                 120                 125 cag gaa gcg agc ctg agc gtg acc agc acc cgc atg cat gaa ccg cag       432
Gln Glu Ala Ser Leu Ser Val Thr Ser Thr Arg Met His Glu Pro Gln
    130                 135                 140 atg ttt ctg ggc gaa aaa gat tgg cat ccg gaa aac cag aac ctg agc       480
Met Phe Leu Gly Glu Lys Asp Trp His Pro Glu Asn Gln Asn Leu Ser
145                 150                 155                 160 cag gtg agc gat ccg cag cag cat gaa gaa ccg ggc aac gaa cag tat       528
Gln Val Ser Asp Pro Gln Gln His Glu Glu Pro Gly Asn Glu Gln Tyr
```

-continued

|  |  |  | 165 |  |  |  | 170 |  |  |  | 175 |  |  |  |
|---|---|---|---|---|---|---|---|---|---|---|---|---|---|---|
| gaa | gtg | gcg | cag | cag | aaa | gcg | agc | cat | gat | cag | gaa | tat | ctg | tgc | aac | 576 |
| Glu | Val | Ala | Gln | Gln | Lys | Ala | Ser | His | Asp | Gln | Glu | Tyr | Leu | Cys | Asn |  |
|  |  |  | 180 |  |  |  | 185 |  |  |  | 190 |  |  |  | att ggc gat ctg gaa ctg ccg gaa gaa cgc cag cag aac cag cat aaa   624
Ile Gly Asp Leu Glu Leu Pro Glu Glu Arg Gln Gln Asn Gln His Lys
        195                 200                 205 att gtg gat ctg gaa gcg acc atg aaa ggc aac ggc ctg ccg cag aac   672
Ile Val Asp Leu Glu Ala Thr Met Lys Gly Asn Gly Leu Pro Gln Asn
210                 215                 220 gtg gat ccg ccg agc gcg aaa aaa agc att ccg agc agc gaa tgc agc   720
Val Asp Pro Pro Ser Ala Lys Lys Ser Ile Pro Ser Ser Glu Cys Ser
225                 230                 235                 240 ggc tgc agc aac agc gaa acc ttt atg gaa att gat acc gcg cag cag   768
Gly Cys Ser Asn Ser Glu Thr Phe Met Glu Ile Asp Thr Ala Gln Gln
                245                 250                 255 agc ctg gtg acc ctg ctg aac agc acc ggc cgc cag aac gcg aac gtg   816
Ser Leu Val Thr Leu Leu Asn Ser Thr Gly Arg Gln Asn Ala Asn Val
        260                 265                 270 aaa aac att ggc gcg ctg gat ctg acc ctg gat aac ccg ctg atg gaa   864
Lys Asn Ile Gly Ala Leu Asp Leu Thr Leu Asp Asn Pro Leu Met Glu
        275                 280                 285 gtg gaa acc agc aaa tgc aac ccg agc agc gaa att ctg aac gat agc   912
Val Glu Thr Ser Lys Cys Asn Pro Ser Ser Glu Ile Leu Asn Asp Ser
290                 295                 300 att agc acc cag gat ctg cag ccg ccg gaa acc aac gtg gaa att ccg   960
Ile Ser Thr Gln Asp Leu Gln Pro Pro Glu Thr Asn Val Glu Ile Pro
305                 310                 315                 320 ggc acc aac aaa gaa tat ggc cat tat agc agc ccg agc ctg tgc ggc  1008
Gly Thr Asn Lys Glu Tyr Gly His Tyr Ser Ser Pro Ser Leu Cys Gly
                325                 330                 335 agc tgc cag ccg agc gtg gaa agc gcg gaa gaa agc tgc ccg agc att  1056
Ser Cys Gln Pro Ser Val Glu Ser Ala Glu Glu Ser Cys Pro Ser Ile
            340                 345                 350 acc gcg gcg ctg aaa gaa ctg cat gaa ctg ctg gtg gtg agc agc aaa  1104
Thr Ala Ala Leu Lys Glu Leu His Glu Leu Leu Val Val Ser Ser Lys
        355                 360                 365 ccg gcg agc gaa aac acc agc gaa gaa gtg att tgc cag agc gaa acc  1152
Pro Ala Ser Glu Asn Thr Ser Glu Glu Val Ile Cys Gln Ser Glu Thr
370                 375                 380 att gcg gaa ggc cag acc agc att aaa gat ctg agc gaa cgc tgg acc  1200
Ile Ala Glu Gly Gln Thr Ser Ile Lys Asp Leu Ser Glu Arg Trp Thr
385                 390                 395                 400 cag aac gaa cat ctg acc cag aac gaa cag tgc ccg cag gtg agc ttt  1248
Gln Asn Glu His Leu Thr Gln Asn Glu Gln Cys Pro Gln Val Ser Phe
                405                 410                 415 cat cag gcg att agc gtg agc gtg gaa acc gaa aaa ctg acc ggc acc  1296
His Gln Ala Ile Ser Val Ser Val Glu Thr Glu Lys Leu Thr Gly Thr
            420                 425                 430 agc agc gat acc ggc cgc gaa gcg gtg gaa aac gtg aac ttt cgc agc  1344
Ser Ser Asp Thr Gly Arg Glu Ala Val Glu Asn Val Asn Phe Arg Ser
        435                 440                 445 ctg ggc gat ggc ctg agc acc gat aaa gaa ggc gtg ccg aaa agc cgc  1392
Leu Gly Asp Gly Leu Ser Thr Asp Lys Glu Gly Val Pro Lys Ser Arg
450                 455                 460 gaa agc att aac aaa aac cgc agc gtg acc gtg acc agc gcg aaa acc  1440
Glu Ser Ile Asn Lys Asn Arg Ser Val Thr Val Thr Ser Ala Lys Thr
465                 470                 475                 480 agc aac cag ctg cat tgc acc ctg ggc gtg gaa att agc ccg aaa ctg  1488

```
Ser Asn Gln Leu His Cys Thr Leu Gly Val Glu Ile Ser Pro Lys Leu
            485                 490                 495 ctg gcg ggc gaa gaa gat gcg ctg aac cag acc agc gaa cag acc aaa   1536
Leu Ala Gly Glu Glu Asp Ala Leu Asn Gln Thr Ser Glu Gln Thr Lys
        500                 505                 510 agc ctg agc agc aac ttt att ctg gtg aaa gat ctg ggc cag ggc att   1584
Ser Leu Ser Ser Asn Phe Ile Leu Val Lys Asp Leu Gly Gln Gly Ile
            515                 520                 525 cag aac agc gtg acc gat cgc ccg gaa acc cgc gaa aac gtg tgc ccg   1632
Gln Asn Ser Val Thr Asp Arg Pro Glu Thr Arg Glu Asn Val Cys Pro
        530                 535                 540 gat gcg agc cgc ccg ctg ctg gaa tat gaa ccg ccg acc agc cat ccg   1680
Asp Ala Ser Arg Pro Leu Leu Glu Tyr Glu Pro Pro Thr Ser His Pro
545                 550                 555                 560 agc agc agc ccg gcg att ctg ccg ccg ctg att ttt ccg gcg acc gat   1728
Ser Ser Ser Pro Ala Ile Leu Pro Pro Leu Ile Phe Pro Ala Thr Asp
            565                 570                 575 att gat cgc att ctg cgc gcg ggc ttt acc ctg cag gaa gcg ctg ggc   1776
Ile Asp Arg Ile Leu Arg Ala Gly Phe Thr Leu Gln Glu Ala Leu Gly
        580                 585                 590 gcg ctg cat cgc gtg ggc ggc aac gcg gat ctg gcg ctg ctg gtg ctg   1824
Ala Leu His Arg Val Gly Gly Asn Ala Asp Leu Ala Leu Leu Val Leu
            595                 600                 605 ctg gcg aaa aac att gtg gtg ccg acc                               1851
Leu Ala Lys Asn Ile Val Val Pro Thr
610                 615

<210> SEQ ID NO 2
<211> LENGTH: 617
<212> TYPE: PRT
<213> ORGANISM: Homo sapiens

<400> SEQUENCE: 2

Met Ser Ser Leu Pro Thr Ser Asp Gly Phe Asn His Pro Ala Arg Ser
1               5                   10                  15

Ser Gly Gln Ser Pro Asp Val Gly Asn Pro Met Ser Leu Ala Arg Ser
            20                  25                  30

Val Ser Ala Ser Val Cys Pro Ile Lys Pro Ser Asp Ser Asp Arg Ile
        35                  40                  45

Glu Pro Lys Ala Val Lys Ala Leu Lys Ala Ser Ala Glu Phe Gln Leu
    50                  55                  60

Asn Ser Glu Lys Lys Glu His Leu Ser Leu Gln Asp Leu Ser Asp His
65                  70                  75                  80

Ala Ser Ser Ala Asp His Ala Pro Thr Asp Gln Ser Pro Ala Met Pro
                85                  90                  95

Met Gln Asn Ser Ser Glu Glu Ile Thr Val Ala Gly Asn Leu Glu Lys
            100                 105                 110

Ser Ala Glu Arg Ser Thr Gln Gly Leu Lys Phe His Leu His Thr Arg
        115                 120                 125

Gln Glu Ala Ser Leu Ser Val Thr Ser Thr Arg Met His Glu Pro Gln
    130                 135                 140

Met Phe Leu Gly Glu Lys Asp Trp His Pro Glu Asn Gln Asn Leu Ser
145                 150                 155                 160

Gln Val Ser Asp Pro Gln Gln His Glu Glu Pro Gly Asn Glu Gln Tyr
                165                 170                 175

Glu Val Ala Gln Gln Lys Ala Ser His Asp Gln Glu Tyr Leu Cys Asn
            180                 185                 190
```

-continued

```
Ile Gly Asp Leu Glu Leu Pro Glu Arg Gln Gln Asn Gln His Lys
        195                 200                 205
Ile Val Asp Leu Glu Ala Thr Met Lys Gly Asn Gly Leu Pro Gln Asn
210                 215                 220
Val Asp Pro Pro Ser Ala Lys Lys Ser Ile Pro Ser Ser Glu Cys Ser
225                 230                 235                 240
Gly Cys Ser Asn Ser Glu Thr Phe Met Glu Ile Asp Thr Ala Gln Gln
                245                 250                 255
Ser Leu Val Thr Leu Leu Asn Ser Thr Gly Arg Gln Asn Ala Asn Val
            260                 265                 270
Lys Asn Ile Gly Ala Leu Asp Leu Thr Leu Asp Asn Pro Leu Met Glu
        275                 280                 285
Val Glu Thr Ser Lys Cys Asn Pro Ser Ser Glu Ile Leu Asn Asp Ser
    290                 295                 300
Ile Ser Thr Gln Asp Leu Gln Pro Pro Glu Thr Asn Val Glu Ile Pro
305                 310                 315                 320
Gly Thr Asn Lys Glu Tyr Gly His Tyr Ser Ser Pro Ser Leu Cys Gly
                325                 330                 335
Ser Cys Gln Pro Ser Val Glu Ser Ala Glu Glu Ser Cys Pro Ser Ile
            340                 345                 350
Thr Ala Ala Leu Lys Glu Leu His Glu Leu Leu Val Val Ser Ser Lys
        355                 360                 365
Pro Ala Ser Glu Asn Thr Ser Glu Glu Val Ile Cys Gln Ser Glu Thr
    370                 375                 380
Ile Ala Glu Gly Gln Thr Ser Ile Lys Asp Leu Ser Glu Arg Trp Thr
385                 390                 395                 400
Gln Asn Glu His Leu Thr Gln Asn Glu Gln Cys Pro Gln Val Ser Phe
                405                 410                 415
His Gln Ala Ile Ser Val Ser Val Thr Glu Lys Leu Thr Gly Thr
            420                 425                 430
Ser Ser Asp Thr Gly Arg Glu Ala Val Glu Asn Val Asn Phe Arg Ser
        435                 440                 445
Leu Gly Asp Gly Leu Ser Thr Asp Lys Glu Gly Val Pro Lys Ser Arg
    450                 455                 460
Glu Ser Ile Asn Lys Asn Arg Ser Val Thr Val Thr Ser Ala Lys Thr
465                 470                 475                 480
Ser Asn Gln Leu His Cys Thr Leu Gly Val Glu Ile Ser Pro Lys Leu
                485                 490                 495
Leu Ala Gly Glu Glu Asp Ala Leu Asn Gln Thr Ser Glu Gln Thr Lys
            500                 505                 510
Ser Leu Ser Ser Asn Phe Ile Leu Val Lys Asp Leu Gly Gln Gly Ile
        515                 520                 525
Gln Asn Ser Val Thr Asp Arg Pro Glu Thr Arg Glu Asn Val Cys Pro
    530                 535                 540
Asp Ala Ser Arg Pro Leu Leu Glu Tyr Glu Pro Pro Thr Ser His Pro
545                 550                 555                 560
Ser Ser Ser Pro Ala Ile Leu Pro Pro Leu Ile Phe Pro Ala Thr Asp
                565                 570                 575
Ile Asp Arg Ile Leu Arg Ala Gly Phe Thr Leu Gln Glu Ala Leu Gly
            580                 585                 590
Ala Leu His Arg Val Gly Gly Asn Ala Asp Leu Ala Leu Leu Val Leu
        595                 600                 605
Leu Ala Lys Asn Ile Val Val Pro Thr
```

<210> SEQ ID NO 3
<211> LENGTH: 1869
<212> TYPE: DNA
<213> ORGANISM: Sus scrofa
<220> FEATURE:
<221> NAME/KEY: CDS
<222> LOCATION: (1)..(1869)

<400> SEQUENCE: 3

| | | | | | | | | | | | | | | | | |
|---|---|---|---|---|---|---|---|---|---|---|---|---|---|---|---|---|
| atg | agc | agc | ctg | ccg | acc | agc | gat | ggc | ttt | aac | cat | cag | gcg | cat | ccg | 48 |
| Met | Ser | Ser | Leu | Pro | Thr | Ser | Asp | Gly | Phe | Asn | His | Gln | Ala | His | Pro | |
| 1 | | | | 5 | | | | | 10 | | | | | 15 | | |
| agc | ggc | cag | cgc | ccg | gaa | att | ggc | agc | ccg | agc | ctg | gcg | cat | agc | | 96 |
| Ser | Gly | Gln | Arg | Pro | Glu | Ile | Gly | Ser | Pro | Ser | Leu | Ala | His | Ser | | |
| | | | 20 | | | | | 25 | | | | | 30 | | | |
| gtg | agc | gcg | agc | gtg | tgc | ccg | ttt | aaa | ccg | agc | gat | ccg | gat | agc | att | 144 |
| Val | Ser | Ala | Ser | Val | Cys | Pro | Phe | Lys | Pro | Ser | Asp | Pro | Asp | Ser | Ile | |
| | | 35 | | | | | 40 | | | | | 45 | | | | |
| gaa | ccg | aaa | gcg | gtg | aaa | gcg | gtg | aaa | gcg | ctg | aaa | gcg | agc | gcg | gaa | 192 |
| Glu | Pro | Lys | Ala | Val | Lys | Ala | Val | Lys | Ala | Leu | Lys | Ala | Ser | Ala | Glu | |
| 50 | | | | | 55 | | | | | 60 | | | | | | |
| ttt | cag | att | acc | ttt | gaa | cgc | aaa | gaa | cag | ctg | ccg | ctg | cag | gat | ccg | 240 |
| Phe | Gln | Ile | Thr | Phe | Glu | Arg | Lys | Glu | Gln | Leu | Pro | Leu | Gln | Asp | Pro | |
| 65 | | | | | 70 | | | | | 75 | | | | | 80 | |
| agc | gat | tgc | gcg | agc | agc | gcg | gat | aac | gcg | ccg | gcg | aac | cag | acc | ccg | 288 |
| Ser | Asp | Cys | Ala | Ser | Ser | Ala | Asp | Asn | Ala | Pro | Ala | Asn | Gln | Thr | Pro | |
| | | | | 85 | | | | | 90 | | | | | 95 | | |
| gcg | att | ccg | ctg | cag | aac | agc | ctg | gaa | gaa | gcg | att | gtg | gcg | gat | aac | 336 |
| Ala | Ile | Pro | Leu | Gln | Asn | Ser | Leu | Glu | Glu | Ala | Ile | Val | Ala | Asp | Asn | |
| | | | 100 | | | | | 105 | | | | | 110 | | | |
| ctg | gaa | aaa | agc | gcg | gaa | ggc | agc | acc | cag | ggc | ctg | aaa | agc | cat | ctg | 384 |
| Leu | Glu | Lys | Ser | Ala | Glu | Gly | Ser | Thr | Gln | Gly | Leu | Lys | Ser | His | Leu | |
| | | 115 | | | | | 120 | | | | | 125 | | | | |
| cat | acc | cgc | cag | gaa | gcg | agc | ctg | agc | gtg | acc | acc | cgc | atg | cag | | 432 |
| His | Thr | Arg | Gln | Glu | Ala | Ser | Leu | Ser | Val | Thr | Thr | Arg | Met | Gln | | |
| | 130 | | | | | 135 | | | | | 140 | | | | | |
| gaa | ccg | cag | cgc | ctg | att | ggc | gaa | aaa | ggc | tgg | cat | ccg | gaa | tat | cag | 480 |
| Glu | Pro | Gln | Arg | Leu | Ile | Gly | Glu | Lys | Gly | Trp | His | Pro | Glu | Tyr | Gln | |
| 145 | | | | | 150 | | | | | 155 | | | | | 160 | |
| gat | ccg | agc | cag | gtg | aac | ggc | ctg | cag | cag | cat | gaa | gaa | ccg | cgc | aac | 528 |
| Asp | Pro | Ser | Gln | Val | Asn | Gly | Leu | Gln | Gln | His | Glu | Glu | Pro | Arg | Asn | |
| | | | | 165 | | | | | 170 | | | | | 175 | | |
| gaa | cag | cat | gaa | gtg | gtg | cag | cag | aac | gcg | ccg | cat | gat | ccg | gaa | cat | 576 |
| Glu | Gln | His | Glu | Val | Val | Gln | Gln | Asn | Ala | Pro | His | Asp | Pro | Glu | His | |
| | | | 180 | | | | | 185 | | | | | 190 | | | |
| ctg | tgc | aac | acc | ggc | gat | ctg | gaa | ctg | ctg | ggc | gaa | cgc | cag | cag | aac | 624 |
| Leu | Cys | Asn | Thr | Gly | Asp | Leu | Glu | Leu | Leu | Gly | Glu | Arg | Gln | Gln | Asn | |
| | | 195 | | | | | 200 | | | | | 205 | | | | |
| cag | ccg | aaa | agc | gtg | ggc | ctg | gaa | acc | gcg | gtg | cgc | ggc | gat | cgc | ccg | 672 |
| Gln | Pro | Lys | Ser | Val | Gly | Leu | Glu | Thr | Ala | Val | Arg | Gly | Asp | Arg | Pro | |
| | 210 | | | | | 215 | | | | | 220 | | | | | |
| cag | cag | gat | gtg | gat | ctg | ccg | ggc | acc | gaa | aaa | aac | att | ctg | ccg | tat | 720 |
| Gln | Gln | Asp | Val | Asp | Leu | Pro | Gly | Thr | Glu | Lys | Asn | Ile | Leu | Pro | Tyr | |
| 225 | | | | | 230 | | | | | 235 | | | | | 240 | |
| ggc | tgc | ttt | ggc | tgc | agc | agc | agc | gaa | acc | ttt | atg | gaa | att | gat | acc | 768 |
| Gly | Cys | Phe | Gly | Cys | Ser | Ser | Ser | Glu | Thr | Phe | Met | Glu | Ile | Asp | Thr | |
| | | | | 245 | | | | | 250 | | | | | 255 | | |
| gtg | gaa | cag | agc | ctg | gtg | gcg | gtg | ctg | aac | agc | gcg | ggc | ggc | cag | aac | 816 |
| Val | Glu | Gln | Ser | Leu | Val | Ala | Val | Leu | Asn | Ser | Ala | Gly | Gly | Gln | Asn | |

-continued

| | | | | | | | | | | | | | | | | |
|---|---|---|---|---|---|---|---|---|---|---|---|---|---|---|---|---|
| | | 260 | | | | 265 | | | | | 270 | | | | | |
| acc | agc | gtg | cgc | aac | att | agc | gcg | agc | gat | ctg | acc | gtg | gat | aac | ccg | 864 |
| Thr | Ser | Val | Arg | Asn | Ile | Ser | Ala | Ser | Asp | Leu | Thr | Val | Asp | Asn | Pro | |
| | | 275 | | | | | 280 | | | | | 285 | | | | |
| ctg | atg | gaa | gtg | gaa | acc | ctg | aaa | tgc | aac | ccg | agc | agc | gaa | ttt | ctg | 912 |
| Leu | Met | Glu | Val | Glu | Thr | Leu | Lys | Cys | Asn | Pro | Ser | Ser | Glu | Phe | Leu | |
| | 290 | | | | | 295 | | | | | 300 | | | | | |
| agc | aac | ccg | acc | agc | acc | cag | aac | ctg | cag | ctg | ccg | gaa | agc | agc | gtg | 960 |
| Ser | Asn | Pro | Thr | Ser | Thr | Gln | Asn | Leu | Gln | Leu | Pro | Glu | Ser | Ser | Val | |
| 305 | | | | | 310 | | | | | 315 | | | | | 320 | |
| gaa | atg | agc | ggc | acc | aac | aaa | gaa | tat | ggc | aac | cat | ccg | agc | agc | ctg | 1008 |
| Glu | Met | Ser | Gly | Thr | Asn | Lys | Glu | Tyr | Gly | Asn | His | Pro | Ser | Ser | Leu | |
| | | | 325 | | | | | 330 | | | | | 335 | | | |
| agc | ctg | tgc | ggc | acc | tgc | cag | ccg | agc | gtg | gaa | agc | gcg | gaa | gaa | agc | 1056 |
| Ser | Leu | Cys | Gly | Thr | Cys | Gln | Pro | Ser | Val | Glu | Ser | Ala | Glu | Glu | Ser | |
| | | | 340 | | | | | 345 | | | | | 350 | | | |
| tgc | agc | agc | att | acc | gcg | gcg | ctg | aaa | gaa | ctg | cat | gaa | ctg | ctg | gtg | 1104 |
| Cys | Ser | Ser | Ile | Thr | Ala | Ala | Leu | Lys | Glu | Leu | His | Glu | Leu | Leu | Val | |
| | | 355 | | | | | 360 | | | | | 365 | | | | |
| att | agc | agc | aaa | ccg | gcg | ctg | gaa | aac | acc | agc | gaa | gaa | gtg | acc | tgc | 1152 |
| Ile | Ser | Ser | Lys | Pro | Ala | Leu | Glu | Asn | Thr | Ser | Glu | Glu | Val | Thr | Cys | |
| | 370 | | | | | 375 | | | | | 380 | | | | | |
| cgc | agc | gaa | att | gtg | acc | gaa | ggc | cag | acc | gat | gtg | aaa | gat | ctg | agc | 1200 |
| Arg | Ser | Glu | Ile | Val | Thr | Glu | Gly | Gln | Thr | Asp | Val | Lys | Asp | Leu | Ser | |
| 385 | | | | | 390 | | | | | 395 | | | | | 400 | |
| gaa | cgc | tgg | acc | cag | agc | gaa | cat | ctg | acc | gcg | gcg | cag | aac | gaa | cag | 1248 |
| Glu | Arg | Trp | Thr | Gln | Ser | Glu | His | Leu | Thr | Ala | Ala | Gln | Asn | Glu | Gln | |
| | | | 405 | | | | | 410 | | | | | 415 | | | |
| tgc | agc | cag | gtg | agc | ttt | tat | cag | gcg | acc | agc | gtg | agc | gtg | aaa | acc | 1296 |
| Cys | Ser | Gln | Val | Ser | Phe | Tyr | Gln | Ala | Thr | Ser | Val | Ser | Val | Lys | Thr | |
| | | | 420 | | | | | 425 | | | | | 430 | | | |
| gaa | gaa | ctg | acc | gat | acc | agc | acc | gat | gcg | ggc | acc | gaa | gat | gtg | gaa | 1344 |
| Glu | Glu | Leu | Thr | Asp | Thr | Ser | Thr | Asp | Ala | Gly | Thr | Glu | Asp | Val | Glu | |
| | | 435 | | | | | 440 | | | | | 445 | | | | |
| aac | att | acc | agc | agc | ggc | ccg | ggc | gat | ggc | ctg | ctg | gtg | gat | aaa | gaa | 1392 |
| Asn | Ile | Thr | Ser | Ser | Gly | Pro | Gly | Asp | Gly | Leu | Leu | Val | Asp | Lys | Glu | |
| | 450 | | | | | 455 | | | | | 460 | | | | | |
| aac | gtg | ccg | cgc | agc | cgc | gaa | agc | gtg | aac | gaa | agc | agc | ctg | gtg | acc | 1440 |
| Asn | Val | Pro | Arg | Ser | Arg | Glu | Ser | Val | Asn | Glu | Ser | Ser | Leu | Val | Thr | |
| 465 | | | | | 470 | | | | | 475 | | | | | 480 | |
| ctg | gat | agc | gcg | aaa | acc | agc | aac | cag | ccg | cat | tgc | acc | ctg | ggc | gtg | 1488 |
| Leu | Asp | Ser | Ala | Lys | Thr | Ser | Asn | Gln | Pro | His | Cys | Thr | Leu | Gly | Val | |
| | | | 485 | | | | | 490 | | | | | 495 | | | |
| gaa | att | agc | ccg | ggc | ctg | ctg | gcg | ggc | gaa | gaa | ggc | gcg | ctg | aac | cag | 1536 |
| Glu | Ile | Ser | Pro | Gly | Leu | Leu | Ala | Gly | Glu | Glu | Gly | Ala | Leu | Asn | Gln | |
| | | | 500 | | | | | 505 | | | | | 510 | | | |
| acc | agc | gaa | cag | acc | gaa | agc | ctg | agc | agc | agc | ttt | att | ctg | gtg | aaa | 1584 |
| Thr | Ser | Glu | Gln | Thr | Glu | Ser | Leu | Ser | Ser | Ser | Phe | Ile | Leu | Val | Lys | |
| | | 515 | | | | | 520 | | | | | 525 | | | | |
| gat | ctg | ggc | cag | ggc | acc | cag | aac | ccg | gtg | acc | aac | cgc | ccg | gaa | acc | 1632 |
| Asp | Leu | Gly | Gln | Gly | Thr | Gln | Asn | Pro | Val | Thr | Asn | Arg | Pro | Glu | Thr | |
| | 530 | | | | | 535 | | | | | 540 | | | | | |
| cgc | gaa | aac | gtg | tgc | ccg | gaa | gcg | gcg | ggc | ctg | cgc | cag | gaa | ttt | gaa | 1680 |
| Arg | Glu | Asn | Val | Cys | Pro | Glu | Ala | Ala | Gly | Leu | Arg | Gln | Glu | Phe | Glu | |
| 545 | | | | | 550 | | | | | 555 | | | | | 560 | |
| ccg | ccg | acc | agc | cat | ccg | agc | agc | agc | ccg | agc | ttt | ctg | gcg | ccg | ctg | 1728 |
| Pro | Pro | Thr | Ser | His | Pro | Ser | Ser | Ser | Pro | Ser | Phe | Leu | Ala | Pro | Leu | |
| | | | 565 | | | | | 570 | | | | | 575 | | | |
| att | ttt | ccg | gcg | gcg | gat | att | gat | cgc | att | ctg | cgc | gcg | ggc | ttt | acc | 1776 |

```
Ile Phe Pro Ala Ala Asp Ile Asp Arg Ile Leu Arg Ala Gly Phe Thr
            580                 585                 590 ctg cag gaa gcg ctg ggc gcg ctg cat cgc gtg ggc ggc aac gcg gat    1824
Leu Gln Glu Ala Leu Gly Ala Leu His Arg Val Gly Gly Asn Ala Asp
        595                 600                 605 ctg gcg ctg ctg gtg ctg ctg gcg aaa aac att gtg gtg ccg acc        1869
Leu Ala Leu Leu Val Leu Leu Ala Lys Asn Ile Val Val Pro Thr
    610                 615                 620

<210> SEQ ID NO 4
<211> LENGTH: 623
<212> TYPE: PRT
<213> ORGANISM: Sus scrofa

<400> SEQUENCE: 4

Met Ser Ser Leu Pro Thr Ser Asp Gly Phe Asn His Gln Ala His Pro
1               5                   10                  15

Ser Gly Gln Arg Pro Glu Ile Gly Ser Pro Ser Leu Ala His Ser
            20                  25                  30

Val Ser Ala Ser Val Cys Pro Phe Lys Pro Ser Asp Pro Asp Ser Ile
        35                  40                  45

Glu Pro Lys Ala Val Lys Ala Val Lys Ala Leu Lys Ala Ser Ala Glu
    50                  55                  60

Phe Gln Ile Thr Phe Glu Arg Lys Glu Gln Leu Pro Leu Gln Asp Pro
65                  70                  75                  80

Ser Asp Cys Ala Ser Ser Ala Asp Asn Ala Pro Ala Asn Gln Thr Pro
                85                  90                  95

Ala Ile Pro Leu Gln Asn Ser Leu Glu Ala Ile Val Ala Asp Asn
            100                 105                 110

Leu Glu Lys Ser Ala Glu Gly Ser Thr Gln Gly Leu Lys Ser His Leu
        115                 120                 125

His Thr Arg Gln Glu Ala Ser Leu Ser Val Thr Thr Thr Arg Met Gln
    130                 135                 140

Glu Pro Gln Arg Leu Ile Gly Glu Lys Gly Trp His Pro Glu Tyr Gln
145                 150                 155                 160

Asp Pro Ser Gln Val Asn Gly Leu Gln Gln His Glu Glu Pro Arg Asn
                165                 170                 175

Glu Gln His Glu Val Val Gln Gln Asn Ala Pro His Asp Pro Glu His
            180                 185                 190

Leu Cys Asn Thr Gly Asp Leu Glu Leu Leu Gly Glu Arg Gln Gln Asn
        195                 200                 205

Gln Pro Lys Ser Val Gly Leu Glu Thr Ala Val Arg Gly Asp Arg Pro
    210                 215                 220

Gln Gln Asp Val Asp Leu Pro Gly Thr Glu Lys Asn Ile Leu Pro Tyr
225                 230                 235                 240

Gly Cys Phe Gly Cys Ser Ser Ser Glu Thr Phe Met Glu Ile Asp Thr
                245                 250                 255

Val Glu Gln Ser Leu Val Ala Val Leu Asn Ser Ala Gly Gly Gln Asn
            260                 265                 270

Thr Ser Val Arg Asn Ile Ser Ala Ser Asp Leu Thr Val Asp Asn Pro
        275                 280                 285

Leu Met Glu Val Glu Thr Leu Lys Cys Asn Pro Ser Ser Glu Phe Leu
    290                 295                 300

Ser Asn Pro Thr Ser Thr Gln Asn Leu Gln Leu Pro Glu Ser Ser Val
305                 310                 315                 320
```

```
Glu Met Ser Gly Thr Asn Lys Glu Tyr Gly Asn His Pro Ser Ser Leu
            325                 330                 335

Ser Leu Cys Gly Thr Cys Gln Pro Ser Val Glu Ser Ala Glu Glu Ser
        340                 345                 350

Cys Ser Ser Ile Thr Ala Ala Leu Lys Glu Leu His Glu Leu Leu Val
            355                 360                 365

Ile Ser Ser Lys Pro Ala Leu Glu Asn Thr Ser Glu Glu Val Thr Cys
    370                 375                 380

Arg Ser Glu Ile Val Thr Glu Gly Gln Thr Asp Val Lys Asp Leu Ser
385                 390                 395                 400

Glu Arg Trp Thr Gln Ser Glu His Leu Thr Ala Ala Gln Asn Glu Gln
                405                 410                 415

Cys Ser Gln Val Ser Phe Tyr Gln Ala Thr Ser Val Ser Val Lys Thr
            420                 425                 430

Glu Glu Leu Thr Asp Thr Ser Thr Asp Ala Gly Thr Glu Asp Val Glu
        435                 440                 445

Asn Ile Thr Ser Ser Gly Pro Gly Asp Gly Leu Leu Val Asp Lys Glu
    450                 455                 460

Asn Val Pro Arg Ser Arg Glu Ser Val Asn Glu Ser Ser Leu Val Thr
465                 470                 475                 480

Leu Asp Ser Ala Lys Thr Ser Asn Gln Pro His Cys Thr Leu Gly Val
                485                 490                 495

Glu Ile Ser Pro Gly Leu Leu Ala Gly Glu Gly Ala Leu Asn Gln
            500                 505                 510

Thr Ser Glu Gln Thr Glu Ser Leu Ser Ser Phe Ile Leu Val Lys
        515                 520                 525

Asp Leu Gly Gln Gly Thr Gln Asn Pro Val Thr Asn Arg Pro Glu Thr
    530                 535                 540

Arg Glu Asn Val Cys Pro Glu Ala Ala Gly Leu Arg Gln Glu Phe Glu
545                 550                 555                 560

Pro Pro Thr Ser His Pro Ser Ser Pro Ser Phe Leu Ala Pro Leu
                565                 570                 575

Ile Phe Pro Ala Ala Asp Ile Asp Arg Ile Leu Arg Ala Gly Phe Thr
            580                 585                 590

Leu Gln Glu Ala Leu Gly Ala Leu His Arg Val Gly Gly Asn Ala Asp
        595                 600                 605

Leu Ala Leu Leu Val Leu Leu Ala Lys Asn Ile Val Val Pro Thr
    610                 615                 620

<210> SEQ ID NO 5
<211> LENGTH: 1746
<212> TYPE: DNA
<213> ORGANISM: Mus musculus
<220> FEATURE:
<221> NAME/KEY: CDS
<222> LOCATION: (1)..(1746)

<400> SEQUENCE: 5 atg agc agc ctg ccg acc agc gat ggc ttt gat cat ccg gcg ccg agc      48
Met Ser Ser Leu Pro Thr Ser Asp Gly Phe Asp His Pro Ala Pro Ser
1               5                   10                  15 ggc cag agc ccg gaa gtg ggc agc ccg acc agc ctg gcg cgc agc gtg      96
Gly Gln Ser Pro Glu Val Gly Ser Pro Thr Ser Leu Ala Arg Ser Val
            20                  25                  30 agc gcg agc gcg tgc gcg att aaa ccg ggc gat ccg aac agc att gaa     144
Ser Ala Ser Ala Cys Ala Ile Lys Pro Gly Asp Pro Asn Ser Ile Glu
        35                  40                  45
```

```
agc ctg gcg atg cag gcg acc aaa gcg agc gcg gaa ttt cag acc aac    192
Ser Leu Ala Met Gln Ala Thr Lys Ala Ser Ala Glu Phe Gln Thr Asn
    50                  55                  60 agc aaa aaa acc gat ccg ccg ccg ctg cag gtg ctg ccg gat ctg gcg    240
Ser Lys Lys Thr Asp Pro Pro Pro Leu Gln Val Leu Pro Asp Leu Ala
65                  70                  75                  80 agc agc gcg gaa cag agc ctg gcg atg ccg ttt cat aaa agc agc aaa    288
Ser Ser Ala Glu Gln Ser Leu Ala Met Pro Phe His Lys Ser Ser Lys
                85                  90                  95 gaa gcg gtg gtg gcg ggc aac ctg gaa aaa agc gtg gaa aaa ggc acc    336
Glu Ala Val Val Ala Gly Asn Leu Glu Lys Ser Val Glu Lys Gly Thr
            100                 105                 110 cag ggc ctg cgc gtg tat ctg cat acc cgc cag gat gcg agc ctg acc    384
Gln Gly Leu Arg Val Tyr Leu His Thr Arg Gln Asp Ala Ser Leu Thr
        115                 120                 125 ctg acc acc acc ggc atg cgc gaa ccg cag att ttt gcg gaa gaa aaa    432
Leu Thr Thr Thr Gly Met Arg Glu Pro Gln Ile Phe Ala Glu Glu Lys
    130                 135                 140 agc tgg cat ccg gaa aac cag acc ccg agc ccg gtg aac ggc ctg cag    480
Ser Trp His Pro Glu Asn Gln Thr Pro Ser Pro Val Asn Gly Leu Gln
145                 150                 155                 160 cag cat cgc gaa acc ggc agc gtg cag cgc gaa gcg ggc cag cag agc    528
Gln His Arg Glu Thr Gly Ser Val Gln Arg Glu Ala Gly Gln Gln Ser
                165                 170                 175 gtg ccg cag gat cag ggc tgc ctg tgc gat gcg gaa gat ctg gaa ctg    576
Val Pro Gln Asp Gln Gly Cys Leu Cys Asp Ala Glu Asp Leu Glu Leu
            180                 185                 190 cat gaa gaa gtg gtg agc ctg gaa gcg ctg cgc aaa ggc gaa ctg cag    624
His Glu Glu Val Val Ser Leu Glu Ala Leu Arg Lys Gly Glu Leu Gln
        195                 200                 205 cgc cat gcg cat ctg ccg agc gcg gaa aaa ggc ctg ccg gcg agc ggc    672
Arg His Ala His Leu Pro Ser Ala Glu Lys Gly Leu Pro Ala Ser Gly
    210                 215                 220 ctg tgc agc tgc ccg tgc agc gaa gcg ctg atg gaa gtg gat acc gcg    720
Leu Cys Ser Cys Pro Cys Ser Glu Ala Leu Met Glu Val Asp Thr Ala
225                 230                 235                 240 gaa cag agc ctg gtg gcg atg tgc agc agc acc ggc cgc cag gat gcg    768
Glu Gln Ser Leu Val Ala Met Cys Ser Ser Thr Gly Arg Gln Asp Ala
                245                 250                 255 gtg att aaa agc ccg agc gtg gcg cat ctg gcg agc gat aac ccg acc    816
Val Ile Lys Ser Pro Ser Val Ala His Leu Ala Ser Asp Asn Pro Thr
            260                 265                 270 atg gaa gtg gaa acc ctg cag agc aac ccg agc tgc gaa ccg gtg gaa    864
Met Glu Val Glu Thr Leu Gln Ser Asn Pro Ser Cys Glu Pro Val Glu
        275                 280                 285 cat agc att ctg acc cgc gaa ctg cag ctg ccg gaa gat aac gtg gat    912
His Ser Ile Leu Thr Arg Glu Leu Gln Leu Pro Glu Asp Asn Val Asp
    290                 295                 300 atg agc acc atg gat aac aaa gat gat aac agc agc agc ctg ctg agc    960
Met Ser Thr Met Asp Asn Lys Asp Asp Asn Ser Ser Ser Leu Leu Ser
305                 310                 315                 320 ggc cat ggc cag ccg agc gtg gaa agc gcg gaa gaa ttt tgc agc agc    1008
Gly His Gly Gln Pro Ser Val Glu Ser Ala Glu Glu Phe Cys Ser Ser
                325                 330                 335 gtg acc gtg gcg ctg aaa gaa ctg cat gaa ctg ctg gtg att agc tgc    1056
Val Thr Val Ala Leu Lys Glu Leu His Glu Leu Leu Val Ile Ser Cys
            340                 345                 350 aaa ccg gcg agc gaa gaa agc ccg gaa cat gtg acc tgc cag agc gaa    1104
Lys Pro Ala Ser Glu Glu Ser Pro Glu His Val Thr Cys Gln Ser Glu
```

```
                     355                 360                 365
att ggc gcg gaa agc cag ccg agc gtg agc gat ctg agc ggc cgc cgc      1152
Ile Gly Ala Glu Ser Gln Pro Ser Val Ser Asp Leu Ser Gly Arg Arg
370                 375                 380 gtg cag agc gtg cat ctg acc ccg agc gat cag tat agc cag ggc agc      1200
Val Gln Ser Val His Leu Thr Pro Ser Asp Gln Tyr Ser Gln Gly Ser
385                 390                 395                 400 tgc cat cag gcg acc agc gaa agc ggc aaa acc gaa att gtg ggc acc      1248
Cys His Gln Ala Thr Ser Glu Ser Gly Lys Thr Glu Ile Val Gly Thr
                405                 410                 415 gcg ccg tgc gcg gcg gtg gaa gat gaa gcg agc acc agc ttt gaa ggc      1296
Ala Pro Cys Ala Ala Val Glu Asp Glu Ala Ser Thr Ser Phe Glu Gly
            420                 425                 430 ctg ggc gat ggc ctg agc ccg gat cgc gaa gat gtg cgc cgc agc acc      1344
Leu Gly Asp Gly Leu Ser Pro Asp Arg Glu Asp Val Arg Arg Ser Thr
        435                 440                 445 gaa agc gcg cgc aaa agc tgc agc gtg gcg att acc agc gcg aaa ctg      1392
Glu Ser Ala Arg Lys Ser Cys Ser Val Ala Ile Thr Ser Ala Lys Leu
450                 455                 460 agc gaa cag ctg ccg tgc acc ctg ggc gtg gaa att gcg ccg gaa ctg      1440
Ser Glu Gln Leu Pro Cys Thr Leu Gly Val Glu Ile Ala Pro Glu Leu
465                 470                 475                 480 gcg gcg agc gaa ggc gcg cat agc cag ccg agc gaa cat gtg cat aac      1488
Ala Ala Ser Glu Gly Ala His Ser Gln Pro Ser Glu His Val His Asn
                485                 490                 495 ccg ggc ccg gat cgc ccg gaa acc agc agc gtg tgc ccg ggc gcg ggc      1536
Pro Gly Pro Asp Arg Pro Glu Thr Ser Ser Val Cys Pro Gly Ala Gly
            500                 505                 510 ctg ccg cgc agc ggc ctg gat cag ccg ccg acc cag agc ctg agc acc      1584
Leu Pro Arg Ser Gly Leu Asp Gln Pro Pro Thr Gln Ser Leu Ser Thr
        515                 520                 525 ccg agc gtg ctg ccg ccg ttt att ttt ccg gcg gcg gat gtg gat cgc      1632
Pro Ser Val Leu Pro Pro Phe Ile Phe Pro Ala Ala Asp Val Asp Arg
    530                 535                 540 att ctg ggc gcg ggc ttt acc ctg cag gaa gcg ctg ggc gcg ctg cat      1680
Ile Leu Gly Ala Gly Phe Thr Leu Gln Glu Ala Leu Gly Ala Leu His
545                 550                 555                 560 cgc gtg ggc ggc aac gcg gat ctg gcg ctg ctg gtg ctg ctg gcg aaa      1728
Arg Val Gly Gly Asn Ala Asp Leu Ala Leu Leu Val Leu Leu Ala Lys
                565                 570                 575 aac att gtg gtg ccg acc                                              1746
Asn Ile Val Val Pro Thr
            580
```

<210> SEQ ID NO 6
<211> LENGTH: 582
<212> TYPE: PRT
<213> ORGANISM: Mus musculus

<400> SEQUENCE: 6

```
Met Ser Ser Leu Pro Thr Ser Asp Gly Phe Asp His Pro Ala Pro Ser
1               5                   10                  15

Gly Gln Ser Pro Glu Val Gly Ser Pro Thr Ser Leu Ala Arg Ser Val
            20                  25                  30

Ser Ala Ser Ala Cys Ala Ile Lys Pro Gly Asp Pro Asn Ser Ile Glu
        35                  40                  45

Ser Leu Ala Met Gln Ala Thr Lys Ala Ser Ala Glu Phe Gln Thr Asn
    50                  55                  60

Ser Lys Lys Thr Asp Pro Pro Leu Gln Val Leu Pro Asp Leu Ala
```

-continued

```
                65                  70                  75                  80
            Ser Ser Ala Glu Gln Ser Leu Ala Met Pro Phe His Lys Ser Ser Lys
                            85                  90                  95
            Glu Ala Val Val Ala Gly Asn Leu Glu Lys Ser Val Glu Lys Gly Thr
                           100                 105                 110
            Gln Gly Leu Arg Val Tyr Leu His Thr Arg Gln Asp Ala Ser Leu Thr
                           115                 120                 125
            Leu Thr Thr Thr Gly Met Arg Glu Pro Gln Ile Phe Ala Glu Glu Lys
                           130                 135                 140
            Ser Trp His Pro Glu Asn Gln Thr Pro Ser Pro Val Asn Gly Leu Gln
            145                 150                 155                 160
            Gln His Arg Glu Thr Gly Ser Val Gln Arg Glu Ala Gly Gln Gln Ser
                           165                 170                 175
            Val Pro Gln Asp Gln Gly Cys Leu Cys Asp Ala Glu Asp Leu Glu Leu
                           180                 185                 190
            His Glu Glu Val Val Ser Leu Glu Ala Leu Arg Lys Gly Glu Leu Gln
                           195                 200                 205
            Arg His Ala His Leu Pro Ser Ala Glu Lys Gly Leu Pro Ala Ser Gly
                           210                 215                 220
            Leu Cys Ser Cys Pro Cys Ser Glu Ala Leu Met Glu Val Asp Thr Ala
            225                 230                 235                 240
            Glu Gln Ser Leu Val Ala Met Cys Ser Ser Thr Gly Arg Gln Asp Ala
                           245                 250                 255
            Val Ile Lys Ser Pro Ser Val Ala His Leu Ala Ser Asp Asn Pro Thr
                           260                 265                 270
            Met Glu Val Glu Thr Leu Gln Ser Asn Pro Ser Cys Glu Pro Val Glu
                           275                 280                 285
            His Ser Ile Leu Thr Arg Glu Leu Gln Leu Pro Glu Asp Asn Val Asp
                           290                 295                 300
            Met Ser Thr Met Asp Asn Lys Asp Asn Ser Ser Ser Leu Leu Ser
            305                 310                 315                 320
            Gly His Gly Gln Pro Ser Val Glu Ser Ala Glu Glu Phe Cys Ser Ser
                           325                 330                 335
            Val Thr Val Ala Leu Lys Glu Leu His Glu Leu Leu Val Ile Ser Cys
                           340                 345                 350
            Lys Pro Ala Ser Glu Glu Ser Pro Glu His Val Thr Cys Gln Ser Glu
                           355                 360                 365
            Ile Gly Ala Glu Ser Gln Pro Ser Val Ser Asp Leu Ser Gly Arg Arg
                           370                 375                 380
            Val Gln Ser Val His Leu Thr Pro Ser Asp Gln Tyr Ser Gln Gly Ser
            385                 390                 395                 400
            Cys His Gln Ala Thr Ser Glu Ser Gly Lys Thr Glu Ile Val Gly Thr
                           405                 410                 415
            Ala Pro Cys Ala Ala Val Glu Asp Glu Ala Ser Thr Ser Phe Glu Gly
                           420                 425                 430
            Leu Gly Asp Gly Leu Ser Pro Asp Arg Glu Asp Val Arg Arg Ser Thr
                           435                 440                 445
            Glu Ser Ala Arg Lys Ser Cys Ser Val Ala Ile Thr Ser Ala Lys Leu
                           450                 455                 460
            Ser Glu Gln Leu Pro Cys Thr Leu Gly Val Glu Ile Ala Pro Glu Leu
            465                 470                 475                 480
            Ala Ala Ser Glu Gly Ala His Ser Gln Pro Ser Glu His Val His Asn
                           485                 490                 495
```

```
                Pro Gly Pro Asp Arg Pro Glu Thr Ser Ser Val Cys Pro Gly Ala Gly
                            500                 505                 510

Leu Pro Arg Ser Gly Leu Asp Gln Pro Pro Thr Gln Ser Leu Ser Thr
                    515                 520                 525

Pro Ser Val Leu Pro Pro Phe Ile Phe Pro Ala Ala Asp Val Asp Arg
                    530                 535                 540

Ile Leu Gly Ala Gly Phe Thr Leu Gln Glu Ala Leu Gly Ala Leu His
                545                 550                 555                 560

Arg Val Gly Gly Asn Ala Asp Leu Ala Leu Leu Val Leu Leu Ala Lys
                                565                 570                 575

Asn Ile Val Val Pro Thr
                            580

<210> SEQ ID NO 7
<211> LENGTH: 1770
<212> TYPE: DNA
<213> ORGANISM: Oryctolagus cuniculus
<220> FEATURE:
<221> NAME/KEY: CDS
<222> LOCATION: (1)..(1770)

<400> SEQUENCE: 7 atg agc agc agc ccg ccg ctg gat ggc agc gat cat ccg gcg cat agc        48
Met Ser Ser Ser Pro Pro Leu Asp Gly Ser Asp His Pro Ala His Ser
1               5                   10                  15 agc ggc cag agc ccg gaa gcg ggc aac ccg acc agc ctg gcg cgc agc        96
Ser Gly Gln Ser Pro Glu Ala Gly Asn Pro Thr Ser Leu Ala Arg Ser
            20                  25                  30 gtg agc gcg agc gtg tgc ccg gtg aaa ccg gat aac ccg gat agc acc       144
Val Ser Ala Ser Val Cys Pro Val Lys Pro Asp Asn Pro Asp Ser Thr
        35                  40                  45 gaa ccg gaa gcg gtg acc gcg ctg gaa gcg agc gat ggc ttt cag att       192
Glu Pro Glu Ala Val Thr Ala Leu Glu Ala Ser Asp Gly Phe Gln Ile
    50                  55                  60 aac agc aaa cag acc gat cgc ctg ccg ctg cag ggc cat agc ccg tgc       240
Asn Ser Lys Gln Thr Asp Arg Leu Pro Leu Gln Gly His Ser Pro Cys
65                  70                  75                  80 gcg gcg gcg gcg gcg ccg agc agc gcg atg ccg ctg cgc cat agc agc       288
Ala Ala Ala Ala Ala Pro Ser Ser Ala Met Pro Leu Arg His Ser Ser
                85                  90                  95 gaa gcg gcg ggc gtg gcg gat agc ctg gaa gcg agc gcg gaa cgc cgc       336
Glu Ala Ala Gly Val Ala Asp Ser Leu Glu Ala Ser Ala Glu Arg Arg
            100                 105                 110 acc cag ggc ctg cgc ttt cat ctg cat acc cgc cag gaa gtg aac ctg       384
Thr Gln Gly Leu Arg Phe His Leu His Thr Arg Gln Glu Val Asn Leu
        115                 120                 125 agc att acc acc acc cgc atg cat gaa ccg cag atg ttt gcg ggc gaa       432
Ser Ile Thr Thr Thr Arg Met His Glu Pro Gln Met Phe Ala Gly Glu
    130                 135                 140 gaa ggc tgg cat ccg gaa aac cag aac ccg agc cag gtg aac gat ctg       480
Glu Gly Trp His Pro Glu Asn Gln Asn Pro Ser Gln Val Asn Asp Leu
145                 150                 155                 160 cag cag cat cag gaa ccg gaa aac gcg cgc cat gaa gcg ggc ccg cgc       528
Gln Gln His Gln Glu Pro Glu Asn Ala Arg His Glu Ala Gly Pro Arg
                165                 170                 175 gat gcg ccg agc gat acc ggc gat ctg gaa ctg ccg ggc gaa cgc cag       576
Asp Ala Pro Ser Asp Thr Gly Asp Leu Glu Leu Pro Gly Glu Arg Gln
            180                 185                 190 cag aaa cat gaa gtg gcg gat cgc gaa gcg acc atg cgc ggc ggc cgc       624
```

```
              Gln Lys His Glu Val Ala Asp Arg Glu Ala Thr Met Arg Gly Gly Arg
                  195                 200                 205 ctg cag cag gat gcg ggc ctg ccg gat ccg ggc aaa ggc gcg ctg ccg          672
Leu Gln Gln Asp Ala Gly Leu Pro Asp Pro Gly Lys Gly Ala Leu Pro
210                 215                 220 agc ggc cat tgc ggc cgc ccg gat agc gaa acc ctg atg gaa gtg gat          720
Ser Gly His Cys Gly Arg Pro Asp Ser Glu Thr Leu Met Glu Val Asp
225                 230                 235                 240 gcg gcg gaa cag agc ctg gtg gcg gtg ctg agc agc agc gtg ggc aac          768
Ala Ala Glu Gln Ser Leu Val Ala Val Leu Ser Ser Ser Val Gly Asn
                245                 250                 255 ggc agc gcg agc ggc ctg acc ctg ggc aac ccg ctg atg gaa gtg gaa          816
Gly Ser Ala Ser Gly Leu Thr Leu Gly Asn Pro Leu Met Glu Val Glu
            260                 265                 270 ctg ccg acc tgc agc ccg agc agc gaa att ctg aac ggc agc att ccg          864
Leu Pro Thr Cys Ser Pro Ser Ser Glu Ile Leu Asn Gly Ser Ile Pro
        275                 280                 285 att cag gat ctg cag ccg ccg gaa ggc agc gtg gaa atg ccg ggc acc          912
Ile Gln Asp Leu Gln Pro Pro Glu Gly Ser Val Glu Met Pro Gly Thr
    290                 295                 300 gat cgc gcg tat ggc ggc cgc gcg agc agc agc gtg tgc ggc agc              960
Asp Arg Ala Tyr Gly Gly Arg Ala Ser Ser Ser Val Cys Gly Ser
305                 310                 315                 320 agc cag ccg ccg gcg gaa agc gcg gaa gaa agc tgc agc agc att acc         1008
Ser Gln Pro Pro Ala Glu Ser Ala Glu Glu Ser Cys Ser Ser Ile Thr
                325                 330                 335 acc gcg ctg aaa gaa ctg cat gaa ctg ctg gtg att agc agc aaa ccg         1056
Thr Ala Leu Lys Glu Leu His Glu Leu Leu Val Ile Ser Ser Lys Pro
            340                 345                 350 gcg agc gaa gcg gcg tat gaa gaa gtg acc tgc cag agc gaa ggc acc         1104
Ala Ser Glu Ala Ala Tyr Glu Glu Val Thr Cys Gln Ser Glu Gly Thr
        355                 360                 365 gcg tgg ggc cag acc cgc gtg aac ccg agc gaa cgc tgg acc gaa agc         1152
Ala Trp Gly Gln Thr Arg Val Asn Pro Ser Glu Arg Trp Thr Glu Ser
    370                 375                 380 gaa cgc cgc acc cag gat gaa gat cgc ccg cag gtg agc cat gcg att         1200
Glu Arg Arg Thr Gln Asp Glu Asp Arg Pro Gln Val Ser His Ala Ile
385                 390                 395                 400 ccg gaa tgc gtg aaa acc gaa aaa ctg acc gat gcg agc ccg gat acc         1248
Pro Glu Cys Val Lys Thr Glu Lys Leu Thr Asp Ala Ser Pro Asp Thr
                405                 410                 415 cgc att gaa gat ggc gaa aac gcg acc ttt cag ggc ccg ggc ggc ggc         1296
Arg Ile Glu Asp Gly Glu Asn Ala Thr Phe Gln Gly Pro Gly Gly Gly
            420                 425                 430 ctg agc acc gat cat ggc gcg ccg cgc agc cgc ggc agc gtg cat gaa         1344
Leu Ser Thr Asp His Gly Ala Pro Arg Ser Arg Gly Ser Val His Glu
        435                 440                 445 agc cgc agc gtg acc gtg acc agc gcg gaa acc agc aac cag agc cat         1392
Ser Arg Ser Val Thr Val Thr Ser Ala Glu Thr Ser Asn Gln Ser His
    450                 455                 460 cgc acc ctg ggc gtg gaa att agc ccg cgc ctg ctg acc ggc gaa ggc         1440
Arg Thr Leu Gly Val Glu Ile Ser Pro Arg Leu Leu Thr Gly Glu Gly
465                 470                 475                 480 gat gcg ctg agc cag acc tgc gaa cag acc aaa agc ctg ctg gtg aaa         1488
Asp Ala Leu Ser Gln Thr Cys Glu Gln Thr Lys Ser Leu Leu Val Lys
                485                 490                 495 gat ctg ggc cag ggc acc cag aac ccg gcg ccg gat cgc ccg gcg acc         1536
Asp Leu Gly Gln Gly Thr Gln Asn Pro Ala Pro Asp Arg Pro Ala Thr
            500                 505                 510
```

| | | | | | | | | | | | | | | | |
|---|---|---|---|---|---|---|---|---|---|---|---|---|---|---|---|
| cgc | gaa | gat | gtg | tgc | cgc | gat | gcg | gcg | cgc | ccg | agc | ctg | gaa | gtg | gaa |
| Arg | Glu | Asp | Val | Cys | Arg | Asp | Ala | Ala | Arg | Pro | Ser | Leu | Glu | Val | Glu |
| | 515 | | | | | 520 | | | | | 525 | | | | |

1584

| | | | | | | | | | | | | | | |
|---|---|---|---|---|---|---|---|---|---|---|---|---|---|---|
| gcg | ccg | ccg | agc | cat | agc | agc | ggc | ccg | tgc | att | ctg | ccg | ccg | ctg | ggc |
| Ala | Pro | Pro | Ser | His | Ser | Ser | Gly | Pro | Cys | Ile | Leu | Pro | Pro | Leu | Gly |
| | 530 | | | | | 535 | | | | | 540 | | | | |

1632

| | | | | | | | | | | | | | | | |
|---|---|---|---|---|---|---|---|---|---|---|---|---|---|---|---|
| ttt | ccg | gcg | gcg | gat | att | gat | cgc | att | ctg | cgc | gcg | ggc | ttt | acc | ctg |
| Phe | Pro | Ala | Ala | Asp | Ile | Asp | Arg | Ile | Leu | Arg | Ala | Gly | Phe | Thr | Leu |
| 545 | | | | | 550 | | | | | 555 | | | | | 560 |

1680

| | | | | | | | | | | | | | | | |
|---|---|---|---|---|---|---|---|---|---|---|---|---|---|---|---|
| cag | gaa | gcg | ctg | ggc | gcg | ctg | cat | cgc | gtg | ggc | ggc | aac | gcg | gat | ctg |
| Gln | Glu | Ala | Leu | Gly | Ala | Leu | His | Arg | Val | Gly | Gly | Asn | Ala | Asp | Leu |
| | | | | 565 | | | | | 570 | | | | | 575 | |

1728

| | | | | | | | | | | | | |
|---|---|---|---|---|---|---|---|---|---|---|---|---|
| gcg | ctg | ctg | gtg | ctg | ctg | gcg | aaa | aac | att | gtg | gtg | ccg | acc |
| Ala | Leu | Leu | Val | Leu | Leu | Ala | Lys | Asn | Ile | Val | Val | Pro | Thr |
| | | | 580 | | | | | 585 | | | | 590 | |

1770

<210> SEQ ID NO 8
<211> LENGTH: 590
<212> TYPE: PRT
<213> ORGANISM: Oryctolagus cuniculus

<400> SEQUENCE: 8

Met Ser Ser Ser Pro Pro Leu Asp Gly Ser Asp His Pro Ala His Ser
1               5                   10                  15

Ser Gly Gln Ser Pro Glu Ala Gly Asn Pro Thr Ser Leu Ala Arg Ser
            20                  25                  30

Val Ser Ala Ser Val Cys Pro Val Lys Pro Asp Asn Pro Asp Ser Thr
        35                  40                  45

Glu Pro Glu Ala Val Thr Ala Leu Glu Ala Ser Asp Gly Phe Gln Ile
    50                  55                  60

Asn Ser Lys Gln Thr Asp Arg Leu Pro Leu Gln Gly His Ser Pro Cys
65                  70                  75                  80

Ala Ala Ala Ala Ala Pro Ser Ser Ala Met Pro Leu Arg His Ser Ser
                85                  90                  95

Glu Ala Ala Gly Val Ala Asp Ser Leu Glu Ala Ser Ala Glu Arg Arg
            100                 105                 110

Thr Gln Gly Leu Arg Phe His Leu His Thr Arg Gln Glu Val Asn Leu
        115                 120                 125

Ser Ile Thr Thr Thr Arg Met His Glu Pro Gln Met Phe Ala Gly Glu
    130                 135                 140

Glu Gly Trp His Pro Glu Asn Gln Asn Pro Ser Gln Val Asn Asp Leu
145                 150                 155                 160

Gln Gln His Gln Glu Pro Glu Asn Ala Arg His Glu Ala Gly Pro Arg
                165                 170                 175

Asp Ala Pro Ser Asp Thr Gly Asp Leu Glu Leu Pro Gly Glu Arg Gln
            180                 185                 190

Gln Lys His Glu Val Ala Asp Arg Glu Ala Thr Met Arg Gly Arg
        195                 200                 205

Leu Gln Gln Asp Ala Gly Leu Pro Asp Pro Gly Lys Gly Ala Leu Pro
    210                 215                 220

Ser Gly His Cys Gly Arg Pro Asp Ser Glu Thr Leu Met Glu Val Asp
225                 230                 235                 240

Ala Ala Glu Gln Ser Leu Val Ala Val Leu Ser Ser Val Gly Asn
                245                 250                 255

Gly Ser Ala Ser Gly Leu Thr Leu Gly Asn Pro Leu Met Glu Val Glu
            260                 265                 270

-continued

```
Leu Pro Thr Cys Ser Pro Ser Glu Ile Leu Asn Gly Ser Ile Pro
            275                 280                 285

Ile Gln Asp Leu Gln Pro Pro Glu Gly Ser Val Glu Met Pro Gly Thr
290                 295                 300

Asp Arg Ala Tyr Gly Gly Arg Ala Ser Ser Ser Val Cys Gly Ser
305                 310                 315                 320

Ser Gln Pro Pro Ala Glu Ser Ala Glu Glu Ser Cys Ser Ser Ile Thr
            325                 330                 335

Thr Ala Leu Lys Glu Leu His Glu Leu Val Ile Ser Ser Lys Pro
            340                 345                 350

Ala Ser Glu Ala Ala Tyr Glu Val Thr Cys Gln Ser Glu Gly Thr
            355                 360                 365

Ala Trp Gly Gln Thr Arg Val Asn Pro Ser Glu Arg Trp Thr Glu Ser
370                 375                 380

Glu Arg Arg Thr Gln Asp Glu Asp Arg Pro Gln Val Ser His Ala Ile
385                 390                 395                 400

Pro Glu Cys Val Lys Thr Glu Lys Leu Thr Asp Ala Ser Pro Asp Thr
                    405                 410                 415

Arg Ile Glu Asp Gly Glu Asn Ala Thr Phe Gln Gly Pro Gly Gly Gly
                    420                 425                 430

Leu Ser Thr Asp His Gly Ala Pro Arg Ser Arg Gly Ser Val His Glu
            435                 440                 445

Ser Arg Ser Val Thr Val Thr Ser Ala Glu Thr Ser Asn Gln Ser His
            450                 455                 460

Arg Thr Leu Gly Val Glu Ile Ser Pro Arg Leu Leu Thr Gly Glu Gly
465                 470                 475                 480

Asp Ala Leu Ser Gln Thr Cys Glu Gln Thr Lys Ser Leu Leu Val Lys
                    485                 490                 495

Asp Leu Gly Gln Gly Thr Gln Asn Pro Ala Pro Asp Arg Pro Ala Thr
                    500                 505                 510

Arg Glu Asp Val Cys Arg Asp Ala Ala Arg Pro Ser Leu Glu Val Glu
            515                 520                 525

Ala Pro Pro Ser His Ser Ser Gly Pro Cys Ile Leu Pro Pro Leu Gly
            530                 535                 540

Phe Pro Ala Ala Asp Ile Asp Arg Ile Leu Arg Ala Gly Phe Thr Leu
545                 550                 555                 560

Gln Glu Ala Leu Gly Ala Leu His Arg Val Gly Gly Asn Ala Asp Leu
                    565                 570                 575

Ala Leu Leu Val Leu Leu Ala Lys Asn Ile Val Val Pro Thr
            580                 585                 590

<210> SEQ ID NO 9
<211> LENGTH: 8
<212> TYPE: PRT
<213> ORGANISM: Homo sapiens

<400> SEQUENCE: 9

Ser Asp Ser Asp Arg Ile Glu Pro
1               5

<210> SEQ ID NO 10
<211> LENGTH: 11
<212> TYPE: PRT
<213> ORGANISM: Homo sapiens

<400> SEQUENCE: 10
```

```
Ile Lys Pro Ser Asp Ser Asp Arg Ile Glu Pro
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Cys Pro Gln Cys Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Cys Pro Gln Cys Pro Gln Cys Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<223> OTHER INFORMATION: see specification as filed for detailed
      description of substitutions and preferred embodiments

<400> SEQUENCE: 13

Gln Cys Pro Xaa Gln Cys Pro
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<223> OTHER INFORMATION: see specification as filed for detailed
      description of substitutions and preferred embodiments

<400> SEQUENCE: 14

Xaa Gln Cys Pro Xaa Gln Cys Pro Xaa
```

```
1               5
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Pro Glu Ile Arg Asp Ser Asp Ser
1               5
```

<210> SEQ ID NO 16
<211> LENGTH: 10
<212> TYPE: PRT
<213> ORGANISM: Homo sapiens

<400> SEQUENCE: 16

```
Gln Asn Glu Gln Cys Pro Gln Val Ser Phe
1               5                   10
```

<210> SEQ ID NO 17
<211> LENGTH: 9
<212> TYPE: PRT
<213> ORGANISM: Homo sapiens

<400> SEQUENCE: 17

```
Gln Asn Glu Gln Cys Pro Gln Val Ser
1               5
```

<210> SEQ ID NO 18
<211> LENGTH: 6
<212> TYPE: PRT
<213> ORGANISM: Homo sapiens

<400> SEQUENCE: 18

```
Gln Asn Glu Gln Cys Pro
1               5
```

<210> SEQ ID NO 19
<211> LENGTH: 6
<212> TYPE: PRT
<213> ORGANISM: Homo sapiens

<400> SEQUENCE: 19

```
Gln Cys Pro Gln Val Ser
1               5
```

<210> SEQ ID NO 20
<211> LENGTH: 6
<212> TYPE: PRT
<213> ORGANISM: Homo sapiens

<400> SEQUENCE: 20

```
Ser Ser Gly Gln Ser Pro
1               5
```

<210> SEQ ID NO 21
<211> LENGTH: 6
<212> TYPE: PRT
<213> ORGANISM: Homo sapiens

<400> SEQUENCE: 21

```
Gln Ser Pro Asp Val Gly
1               5

<210> SEQ ID NO 22
<211> LENGTH: 9
<212> TYPE: PRT
<213> ORGANISM: Homo sapiens

<400> SEQUENCE: 22

Ser Ser Gly Gln Ser Pro Asp Val Gly
1               5

<210> SEQ ID NO 23
<211> LENGTH: 6
<212> TYPE: PRT
<213> ORGANISM: Homo sapiens

<400> SEQUENCE: 23

Pro Thr Asp Gln Ser Pro
1               5

<210> SEQ ID NO 24
<211> LENGTH: 6
<212> TYPE: PRT
<213> ORGANISM: Homo sapiens

<400> SEQUENCE: 24

Gln Ser Pro Ala Met Pro
1               5

<210> SEQ ID NO 25
<211> LENGTH: 9
<212> TYPE: PRT
<213> ORGANISM: Homo sapiens

<400> SEQUENCE: 25

Pro Thr Asp Gln Ser Pro Ala Met Pro
1               5

<210> SEQ ID NO 26
<211> LENGTH: 6
<212> TYPE: PRT
<213> ORGANISM: Homo sapiens

<400> SEQUENCE: 26

Gln Asp Leu Gln Pro Pro
1               5

<210> SEQ ID NO 27
<211> LENGTH: 6
<212> TYPE: PRT
<213> ORGANISM: Homo sapiens

<400> SEQUENCE: 27

Gln Pro Pro Glu Thr Asn
1               5

<210> SEQ ID NO 28
<211> LENGTH: 9
<212> TYPE: PRT
<213> ORGANISM: Homo sapiens

<400> SEQUENCE: 28

Gln Asp Leu Gln Pro Pro Glu Thr Asn
1               5
```

```
<210> SEQ ID NO 29
<211> LENGTH: 9
<212> TYPE: PRT
<213> ORGANISM: Homo sapiens

<400> SEQUENCE: 29

Ser Val Gln Pro Cys Gln Glu Asn Gln
1               5

<210> SEQ ID NO 30
<211> LENGTH: 11
<212> TYPE: PRT
<213> ORGANISM: Homo sapiens

<400> SEQUENCE: 30

Pro Glu Ile Arg Asp Ser Asp Ser Pro Lys Ile
1               5                   10
```